(12) United States Patent
Rue et al.

(10) Patent No.: US 8,710,192 B2
(45) Date of Patent: Apr. 29, 2014

(54) PCSK9 ANTAGONISTS

(75) Inventors: Sarah Rue, San Diego, CA (US); Steve B. Cohen, San Diego, CA (US); Jun Li, San Diego, CA (US); David Yowe, Belmont, MA (US)

(73) Assignees: IRM LLC, Hamilton (BM); Novartis AG, Basel (CH)

( * ) Notice: Subject to any disclaimer, the term of this patent is extended or adjusted under 35 U.S.C. 154(b) by 297 days.

(21) Appl. No.: 12/965,743

(22) Filed: Dec. 10, 2010

(65) Prior Publication Data

US 2011/0142849 A1 Jun. 16, 2011

Related U.S. Application Data

(60) Provisional application No. 61/285,942, filed on Dec. 11, 2009.

(51) Int. Cl.
C07K 16/40 (2006.01)
C07K 16/00 (2006.01)
A61K 39/395 (2006.01)

(52) U.S. Cl.
USPC ............. 530/388.26; 530/388.1; 530/387.1; 424/146.1; 424/135.1; 424/141.1

(58) Field of Classification Search
None
See application file for complete search history.

(56) References Cited

U.S. PATENT DOCUMENTS

| | | | |
|---|---|---|---|
| 3,983,140 | A | 9/1976 | Endo |
| 4,444,784 | A | 4/1984 | Hoffman |
| 5,006,530 | A | 4/1991 | Angerbauer |
| 5,177,080 | A | 1/1993 | Angerbauer |
| 5,260,440 | A | 11/1993 | Hirai et al. |
| 5,273,995 | A | 12/1993 | Roth |
| 8,030,457 | B2 | 10/2011 | Jackson et al. |
| 8,062,640 | B2 | 11/2011 | Sleeman et al. |
| 8,080,243 | B2 | 12/2011 | Liang et al. |
| 2009/0232795 | A1 | 9/2009 | Condra et al. |
| 2009/0246192 | A1 | 10/2009 | Condra et al. |
| 2011/0230392 | A1 | 9/2011 | Chiang et al. |

FOREIGN PATENT DOCUMENTS

| | | |
|---|---|---|
| EP | 33538 | 8/1981 |
| WO | WO0157081 | 8/2001 |
| WO | WO2008057457 | 5/2008 |
| WO | WO2008057458 | 5/2008 |
| WO | WO2008057459 | 5/2008 |
| WO | WO2009026558 | 2/2009 |
| WO | WO2009100297 | 8/2009 |
| WO | WO2010009513 | 3/2010 |
| WO | WO2010068526 | 6/2010 |
| WO | WO2010077854 | 7/2010 |

OTHER PUBLICATIONS

Rudikoff et al. (Proc Natl Acad Sci USA 1982 vol. 79 p. 1979.*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881.*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Lederman et al. (Molecular Immunology 28: 1171-1181, 1991.*
Li et al. (PNAS 77: 3211-3214, 1980.*
Houghten et al. (New Approaches to Immunization, Vaccines 86, Cold Spring Harbor Laboratory, p. 21-25, 1986).*
Duff, et al., "Antibody-mediated disruption of the interaction between PCSK9 and the low-density lipoprotein receptor", The Biochemical Journal, May 1, 2009, pp. 577-584, vol. 419, No. 3.
Ni, et al., "A PCSK9 C-terminal Domain Binding Fab Inhibits PCSK9 Internalization and Restores LDL-uptake", Circulation, Nov. 1, 2009, p. S477, vol. 120, No. 18, Suppl. 2, Lippincott Williams & Williams, US.
Li, et al., "Recent patents on PCSK9: a new target for treating hypercholesterolemia", Recent Patents on DNA & Gene Sequences, Nov. 2009, pp. 201-212, vol. 3, No. 3.
Ni, et al., "A proprotein convertase subtilisin-like/kexin type 9 (PCSK9) C-terminal domain antibody antigen-binding fragment inhibits PCSK9 internalization and restores low density lipoprotein uptake", The Journal of Biolgoical Chemistry, Apr. 23, 2010, pp. 12882-12891, vol. 285, No. 17.
PCT/US2010/059959 International Search Report and Written Opinion dated Feb. 10, 2011.

* cited by examiner

*Primary Examiner* — Sharon Wen

(74) *Attorney, Agent, or Firm* — Timothy L. Smith; Genomics Institute of the Novartis Research Foundation

(57) ABSTRACT

The present invention provides antibody antagonists against proprotein convertase subtilisin/kexin type 9a ("PCSK9") and methods of using such antibodies.

20 Claims, 18 Drawing Sheets

*Figure 1*

Variable region sequences of parent mouse mAb LFU720

LFU720 Heavy Chain Variable Region

EVQLQQSGAELMKPGASVKLSCTASGFNIKDMYMSWVRQRPEQGLEWIGRIDPAN GHTNYDPKFQAKATITTDTSSKTAYLHLSSLTSEDTAVYYCARSYYYYAMDYWGQ GTSVTVSS

LFU720 Light (kappa) Chain Variable Region

QIVLTQSPAIMSASPGEKVTMTCSASSSVSYMHWYQQKPGSSPRLWIYLTFNLA SGVPARFSGSGSGTSYSLSISSMEAEDAATYYCLQWSSDPPTFGSGTKLEIK

*Figure 2*

Variable region sequences of Ab NVP-LGT209 pJG04 (Vh) +pJG10 (Vk)

pJG04 Vh

QVQLVQSGAEVKKPGASVKVSCKASGYTFSTMYMSWVRQAPGQGLEWMG**RIDPA
NEHTNYAQKFQGRVTMTRDTSISTAYMELSRLTSDDTAVYYCARSYYYYNMDY**W
GQGTLVTVSS pJG10 Vk

QIVLTQSPATLSVSPGERATLSCRASQSVSYMHWYQQKPGQAPRLLIYGVFRRATGI
PDRFSGSGSGTDFTLTIGRLEPEDFAVYYCLQWSSDPPTFGQGTKLEIK

*Figure 3*

Variable region sequences of Ab NVP-LGT210 pJG04 (Vh) +pJG01 (Vk)

pJG04 Vh

QVQLVQSGAEVKKPGASVKVSCKASGYTFSTMYMSWVRQAPGQGLEWMG**RIDPA
NEHTNYAQKFQGRVTMTRDTSISTAYMELSRLTSDDTAVYYCARSYYYYNMDY**W
GQGTLVTVSS pJG01 Vk

EIVMTQSPATLSVSPGERATLSCRASQSVSYMHWYQQKPGQAPRLLIYGVFRRATG
IPDRFSGSGSGTDFTLTIGRLEPEDFAVYYCLQWSSDPPTFGQGTKLEIK

*Figure 4*

Variable region sequences of Ab NVP-LGT211 pSR74 (Vh) +pJG10 (Vk)

pSR074 Vh

QVQLVQSGAEVKKPGASVKVSCKASGYTFSTMYMSWVRQAPGQGLEWMG**RIDPA
NEHTNYAQKFQGRVTMTRDTSISTAYMELSRLTSDDTAVYYCARSYYYYAMDY**W
GQGTLVTVSS pJG10 Vk

QIVLTQSPATLSVSPGERATLSCRASQSVSYMHWYQQKPGQAPRLLIYGVFRRATGI
PDRFSGSGSGTDFTLTIGRLEPEDFAVYYCLQWSSDPPTFGQGTKLEIK

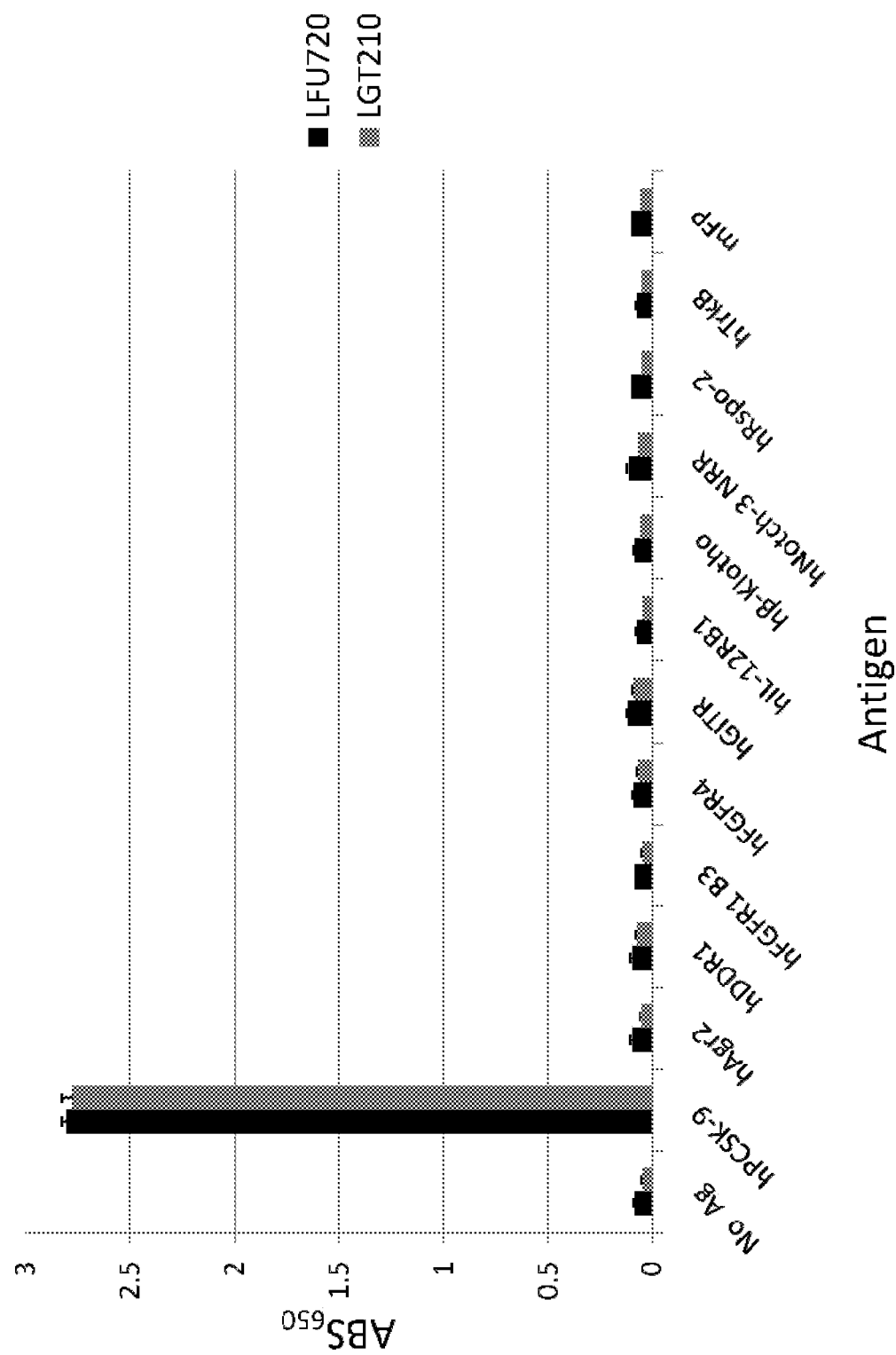

*Figure 11*
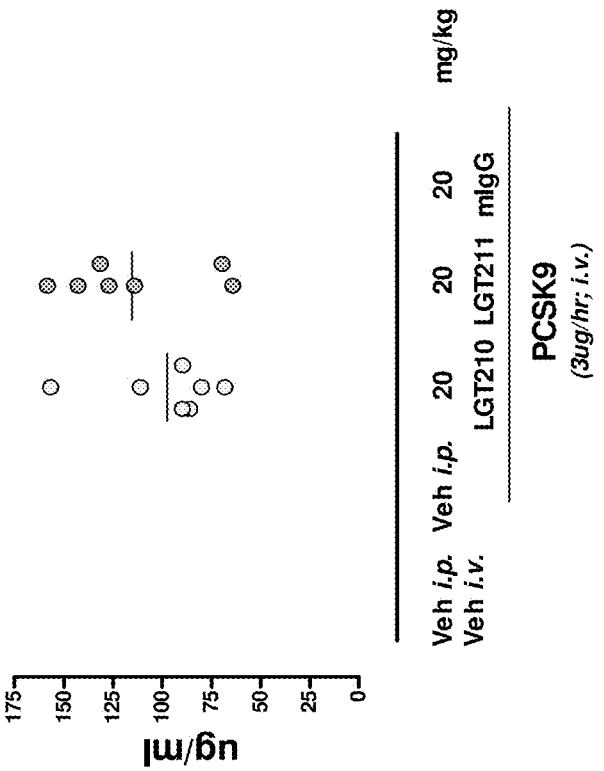
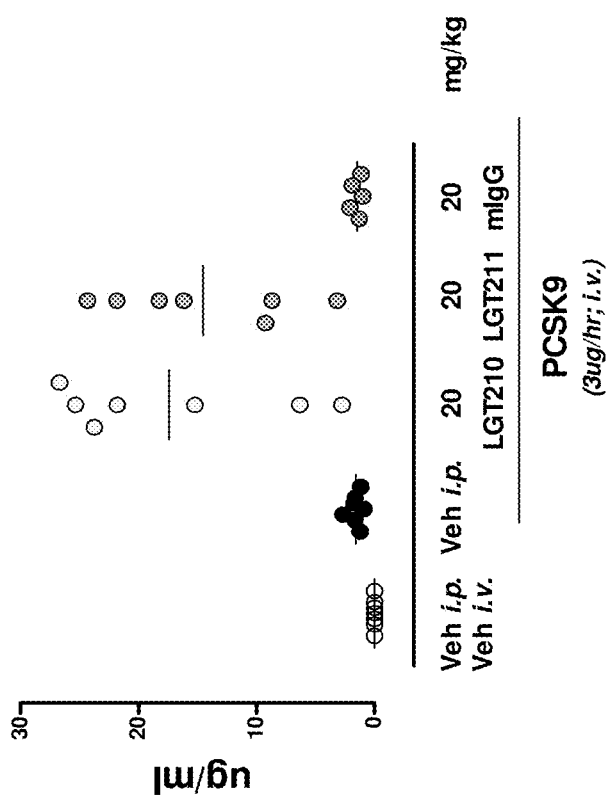

US 8,710,192 B2

PCSK9 ANTAGONISTS

CROSS-REFERENCE TO RELATED PATENT APPLICATIONS

The present invention claims benefit of priority to U.S. Provisional Patent Application No. 61/285,942, filed Dec. 11, 2009, which is incorporated by reference for all purposes.

FIELD OF THE INVENTION

The present invention relates to antibody antagonists against PCSK9.

BACKGROUND OF THE INVENTION

The low-density lipoprotein receptor (LDL-R) prevents atherosclerosis and hypercholesterolemia through the clearance of the low-density lipoproteins (LDL) in the bloodstream. LDL-R is regulated at the posttranslational level by proprotein convertase subtilisin/kexin type 9a ("PCSK9"). Recently, the knockout of PCSK9 was reported in mice. These mice showed an approximate 50% reduction in the plasma cholesterol levels and showed enhanced sensitivity to statins in reducing plasma cholesterol (Rashid S, et al (2005) *Proc Natl Acad Sci* 102:5374-5379. Human genetic data also support the role of PCSK9 in LDL homeostasis. Two mutations were recently identified that are presumably "loss-of-function" mutations in PCSK9. The individuals with these mutations have an approximately 40% reduction in the plasma levels of LDL-C which translates into an approximate 50-90% decrease in coronary heart disease. Taken together, these studies indicate that an inhibitor of PCSK9 would be beneficial for lowering plasma concentrations of LDL-C and other disease conditions mediated by PCSK9 and could be co-administered, e.g., with a second agent useful for lowering cholesterol for increased efficacy.

BRIEF SUMMARY OF THE INVENTION

The present invention provides antibodies that bind to and antagonize the function of proprotein convertase subtilisin/kexin type 9 (PCSK9) (e.g., SEQ ID NO:47), and methods for using such antibodies, e.g., to treat disease conditions mediated by PCSK9.

In one aspect, the invention provides antibodies and antigen binding molecules that bind to proprotein convertase subtilisin/kexin type 9 (PCSK9). In some embodiments, the antibody:

a) does not block PCSK9 binding to the low density lipoprotein receptor (LDLR) and
b) inhibits PCSK9-mediated degradation of LDLR.

In some embodiments, the antibody or antigen binding molecule binds to at least one amino acid within residue positions 680-692 of human PCSK9. For example, in some embodiments, the antibody or antigen binding molecule binds to an epitope of PCSK9 within the amino acid sequence RSRHLAQASQELQ (SEQ ID NO:49).

In some embodiments, the antibody or antigen binding molecule binds to human PCSK9 with an equilibrium dissociation constant (KD) of about 500 pM or less. For example, in some embodiments, the antibody or antigen binding molecule binds to human PCSK9 with an equilibrium dissociation constant (KD) of about 400 pM, 300 pM, 250 pM, 200 pM, 190 pM, 180 pM, 170 pM, 160 pM, 150 pM, 140 pM, or less.

In some embodiments, the antibody or antigen binding molecule has an in vivo half-life of at least about 7 days. In some embodiments the antibody or antigen binding molecule has an in vivo half-life of at least about 3, 4, 5, 6, 7, 8, 9, 10 days. In some embodiments, the antibody or antigen binding molecule has an in vivo cholesterol lowering effect of at least about 2 weeks, for example, 2, 3, 4 weeks or longer. Preferably, the in vivo half-life is determined in a human subject.

In some embodiments, the antibody comprises
(a) a heavy chain variable region comprising a human heavy chain V-segment, a heavy chain complementarity determining region 3 (CDR3), and a heavy chain framework region 4 (FR4), and
(b) a light chain variable region comprising a human light chain V segment, a light chain CDR3, and a light chain FR4, wherein
i) the heavy chain CDR3 comprises the amino acid sequence SYYYY(A/N)MD(A/F/S/V/Y) (SEQ ID NO:14); and
ii) the light chain CDR3 variable region comprises the amino acid sequence LQWSSDPPT (SEQ ID NO:26).

In some embodiments, the antibody comprises
(a) a heavy chain variable region comprising a human heavy chain V-segment, a heavy chain complementarity determining region 3 (CDR3), and a heavy chain framework region 4 (FR4), and
(b) a light chain variable region comprising a human light chain V segment, a light chain CDR3, and a light chain FR4, wherein
i) the heavy chain CDR3 comprises the amino acid sequence SYYYYNMDY (SEQ ID NO:12); and
ii) the light chain CDR3 variable region comprises the amino acid sequence LQWSSDPPT (SEQ ID NO:26).

In some embodiments, the antibody comprises
(a) a heavy chain variable region comprising a human heavy chain V-segment, a heavy chain complementarity determining region 3 (CDR3), and a heavy chain framework region 4 (FR4), and
(b) a light chain variable region comprising a human light chain V segment, a light chain CDR3, and a light chain FR4, wherein
i) the heavy chain CDR3 comprises the amino acid sequence SYYYYAMDY (SEQ ID NO:13); and
ii) the light chain CDR3 variable region comprises the amino acid sequence LQWSSDPPT (SEQ ID NO:26).

In some embodiments, the heavy chain CDR3 comprises the amino acid sequence selected from the group consisting of SEQ ID NO:12 and SEQ ID NO:13; and the light chain CDR3 comprises the amino acid sequence of SEQ ID NO:26.

In some embodiments, the heavy chain V-segment has at least 85%, 88%, 89%, 90% 91%, 92%, 93%, 94%, 95%, 96%, 97%, 98% or 99% sequence identity to SEQ ID NO:28, and wherein the light chain V segment has at least 85%, 88%, 89%, 90% 91%, 92%, 93%, 94%, 95%, 96%, 97%, 98% or 99% sequence identity to SEQ ID NO:31.

In some embodiments, the heavy chain V-segment has at least 85%, 88%, 89%, 90% 91%, 92%, 93%, 94%, 95%, 96%, 97%, 98% or 99% sequence identity to SEQ ID NO:27, and wherein the light chain V segment has at least 85%, 88%, 89%, 90% 91%, 92%, 93%, 94%, 95%, 96%, 97%, 98% or 99% sequence identity to the amino acid selected from the group consisting of SEQ ID NO:29 and SEQ ID NO:30.

In some embodiments, the heavy chain FR4 is a human germline FR4. In some embodiments, the heavy chain FR4 is SEQ ID NO:35.

In some embodiments, the light chain FR4 is a human germline FR4. In some embodiments, the light chain FR4 is SEQ ID NO:39.

In some embodiments, the heavy chain V-segment and the light chain V-segment each comprise a complementarity determining region 1 (CDR1) and a complementarity determining region 2 (CDR2); wherein:
 i) the CDR1 of the heavy chain V-segment comprises the amino acid sequence of SEQ ID NO:8;
 ii) the CDR2 of the heavy chain V-segment comprises the amino acid sequence of SEQ ID NO:11;
 iii) the CDR1 of the light chain V-segment comprises the amino acid sequence of SEQ ID NO:22; and
 iv) the CDR2 of the light chain V-segment comprises the amino acid sequence of SEQ ID NO:25.

In some embodiments, the heavy chain V-segment and the light chain V-segment each comprise a complementarity determining region 1 (CDR1) and a complementarity determining region 2 (CDR2); wherein:
 i) the CDR1 of the heavy chain V-segment comprises the amino acid sequence of SEQ ID NO:7;
 ii) the CDR2 of the heavy chain V-segment comprises the amino acid sequence of SEQ ID NO:10;
 iii) the CDR1 of the light chain V-segment comprises the amino acid sequence of SEQ ID NO:21; and
 iv) the CDR2 of the light chain V-segment comprises the amino acid sequence of SEQ ID NO:24.

In some embodiments,
 i) the CDR1 of the heavy chain V-segment comprises SEQ ID NO:7;
 ii) the CDR2 of the heavy chain V-segment comprises SEQ ID NO:10;
 iii) the heavy chain CDR3 comprises the amino acid sequence selected from the group consisting of SEQ ID NO:12 and SEQ ID NO:13;
 iv) the CDR1 of the light chain V-segment comprises SEQ ID NO:21;
 v) the CDR2 of the light chain V-segment comprises SEQ ID NO:24; and
 vi) the light chain CDR3 comprises SEQ ID NO:26.

In some embodiments, the heavy chain variable region has at least 85%, 88%, 89%, 90% 91%, 92%, 93%, 94%, 95%, 96%, 97%, 98% or 99% amino acid sequence identity to the variable region of SEQ ID NO:40 and the light chain variable region has at least 90% amino acid sequence identity to the variable region of SEQ ID NO:41.

In some embodiments, the antibody comprises a heavy chain comprising SEQ ID NO:40 and a light chain comprising SEQ ID NO:41.

In some embodiments, the heavy chain variable region has at least 85%, 88%, 89%, 90% 91%, 92%, 93%, 94%, 95%, 96%, 97%, 98% or 99% amino acid sequence identity to the variable region selected from the group consisting of SEQ ID NO:2 and SEQ ID NO:4 and the light chain variable region has at least 85%, 88%, 89%, 90% 91%, 92%, 93%, 94%, 95%, 96%, 97%, 98% or 99% amino acid sequence identity to the variable region selected from the group consisting of SEQ ID NO:16 and SEQ ID NO:18.

In some embodiments, the heavy chain variable region comprises the amino acid sequence selected from the group consisting of SEQ ID NO:2 and SEQ ID NO:4 and the light chain variable region comprises the amino acid sequence selected from the group consisting of SEQ ID NO:16 and SEQ ID NO:18.

In some embodiments, the antibody is an IgG. In some embodiments, the antibody is an IgG1. In some embodiments, the antibody has a heavy chain sharing at least 85%, 88%, 89%, 90% 91%, 92%, 93%, 94%, 95%, 96%, 97%, 98% or 99% sequence identity to an amino acid selected from the group consisting of SEQ ID NO:3 and SEQ ID NO:5. In some embodiments, the antibody has a light chain sharing at least 85%, 88%, 89%, 90% 91%, 92%, 93%, 94%, 95%, 96%, 97%, 98% or 99% sequence identity to an amino acid selected from the group consisting of SEQ ID NO:17 and SEQ ID NO:19.

In some embodiments, the antibody is a FAb' fragment. In some embodiments, the antibody is a single chain antibody (scFv). In some embodiments, the antibody comprises human constant regions. In some embodiments, the antibody comprises a human IgG1 constant region. In some embodiments, the human IgG1 constant region is mutated to have reduced binding affinity for an effector ligand such as Fc receptor (FcR), e.g., Fc gamma R1, on a cell or the C1 component of complement. See, e.g., U.S. Pat. No. 5,624,821. In some embodiments, amino acid residues L234 and L235 of the IgG1 constant region are substituted to Ala234 and Ala235. The numbering of the residues in the heavy chain constant region is that of the EU index (see, Kabat, et al., (1983) "Sequences of Proteins of Immunological Interest," U.S. Dept. Health and Human Services).

In some embodiments, the antibody is linked to a carrier protein, for example, albumin.

In some embodiments, the antibody is PEGylated.

In a related aspect, the invention provides antibodies that bind to PCSK9, wherein the antibody comprises a heavy chain variable region and a light chain variable region, wherein the heavy chain variable region and the light chain variable region each comprise the following three complementarity determining regions (CDRs): CDR1, CDR2 and CDR3; wherein:
 i) the CDR1 of the heavy chain variable region comprises the amino acid sequence of SEQ ID NO:8;
 ii) the CDR2 of the heavy chain variable region comprises the amino acid sequence of SEQ ID NO:11;
 iii) the CDR3 of the heavy chain variable region comprises the amino acid sequence of SEQ ID NO:14;
 iv) the CDR1 of the light chain variable region comprises the amino acid sequence of SEQ ID NO:22;
 v) the CDR2 of the light chain variable region comprises the amino acid sequence of SEQ ID NO:25;
 vi) the CDR3 of the light chain variable region comprises the amino acid sequence of SEQ ID NO:26.

In some embodiments,
 i) the CDR1 of the heavy chain variable region comprises the amino acid sequence selected from the group consisting of SEQ ID NO:6 and SEQ ID NO:7;
 ii) the CDR2 of the heavy chain variable region comprises the amino acid sequence selected from the group consisting of SEQ ID NO:9 and SEQ ID NO:10;
 iii) the CDR3 of the heavy chain variable region comprises the amino acid sequence selected from the group consisting of SEQ ID NO:12 and SEQ ID NO:13;
 iv) the CDR1 of the light chain variable region comprises the amino acid sequence selected from the group consisting of SEQ ID NO:20 and SEQ ID NO:21;
 v) the CDR2 of the light chain variable region comprises the amino acid sequence selected from the group consisting of SEQ ID NO:23 and SEQ ID NO:24;
 vi) the CDR3 of the light chain variable region comprises the amino acid sequence of SEQ ID NO:26.

In a related aspect, the invention provides antibodies that bind to PCSK9, wherein the antibody comprises a heavy chain variable region and a light chain variable region, wherein the heavy chain variable region and the light chain variable region each comprise the following three complementarity determining regions (CDRs): CDR1, CDR2 and CDR3; wherein:

i) the CDR1 of the heavy chain variable region comprises the amino acid sequence of SEQ ID NO:6;
ii) the CDR2 of the heavy chain variable region comprises the amino acid sequence of SEQ ID NO:9;
iii) the CDR3 of the heavy chain variable region comprises the amino acid sequence of SEQ ID NO:13;
iv) the CDR1 of the light chain variable region comprises the amino acid sequence of SEQ ID NO:20;
v) the CDR2 of the light chain variable region comprises the amino acid sequence of SEQ ID NO:23;
vi) the CDR3 of the light chain variable region comprises the amino acid sequence of SEQ ID NO:26.

In a related aspect, the invention provides antibodies that bind to PCSK9, wherein the antibody comprises a heavy chain variable region and a light chain variable region, wherein the heavy chain variable region and the light chain variable region each comprise the following three complementarity determining regions (CDRs): CDR1, CDR2 and CDR3; wherein:

i) the CDR1 of the heavy chain variable region comprises the amino acid sequence of SEQ ID NO:7;
ii) the CDR2 of the heavy chain variable region comprises the amino acid sequence of SEQ ID NO:10;
iii) the CDR3 of the heavy chain variable region comprises the amino acid sequence of SEQ ID NO:12;
iv) the CDR1 of the light chain variable region comprises the amino acid sequence of SEQ ID NO:21;
v) the CDR2 of the light chain variable region comprises the amino acid sequence of SEQ ID NO:24;
vi) the CDR3 of the light chain variable region comprises the amino acid sequence of SEQ ID NO:26.

In a related aspect, the invention provides antibodies that bind to PCSK9, wherein the antibody comprises a heavy chain variable region and a light chain variable region, wherein the heavy chain variable region and the light chain variable region each comprise the following three complementarity determining regions (CDRs): CDR1, CDR2 and CDR3; wherein:

i) the CDR1 of the heavy chain variable region comprises the amino acid sequence of SEQ ID NO:7;
ii) the CDR2 of the heavy chain variable region comprises the amino acid sequence of SEQ ID NO:10;
iii) the CDR3 of the heavy chain variable region comprises the amino acid sequence of SEQ ID NO:13;
iv) the CDR1 of the light chain variable region comprises the amino acid sequence of SEQ ID NO:21;
v) the CDR2 of the light chain variable region comprises the amino acid sequence of SEQ ID NO:24;
vi) the CDR3 of the light chain variable region comprises the amino acid sequence of SEQ ID NO:26.

In a further aspect, the invention provides compositions comprising an antibody or antigen binding molecule as described herein and a physiologically compatible excipient.

In some embodiments, the composition further comprises a second agent that reduces low density lipoprotein cholesterol (LDL-C) levels in an individual.

In some embodiments, the second agent is a statin. For example, the statin can be selected from the group consisting of atorvastatin, cerivastatin, fluvastatin, lovastatin, mevastatin, pitavastatin, pravastatin, rosuvastatin, and simvastatin.

In some embodiments, the second agent is selected from the group consisting of fibrates, niacin and analogs thereof, a cholesterol absorption inhibitor, a bile acid sequestrant, a thyroid hormone mimetic, a microsomal triglyceride transfer protein (MTP) inhibitor, a diacylglycerol acyltransferase (DGAT) inhibitor, an inhibitory nucleic acid targeting PCSK9 and an inhibitory nucleic acid targeting apoB100.

In a further aspect, the invention provides methods of reducing LDL-C, non-HDL-C and/or total cholesterol in an individual in need thereof, the method comprising administering a therapeutically effective amount to the individual an antibody or antigen binding molecule as described herein.

In some embodiments, the individual is hyporesponsive or resistant to statin therapy. In some embodiments, the individual is intolerant to statin therapy. In some embodiments, the individual has a baseline LDL-C level of at least about 100 mg/dL, for example, at least about 110, 120, 130, 140, 150, 160, 170, 180, 190 mg/dL, or higher. In some embodiments, the individual has familial hypercholesterolemia. In some embodiments, the individual has triglyceridemia. In some embodiments, the individual has a gain-of-function PCSK9 gene mutation. In some embodiments, the individual has drug-induced dyslipidemia.

In some embodiments, total cholesterol is reduced with LDL-C.

In some embodiments, the methods further comprise administering a therapeutically effective amount of a second agent effective in reducing LDL-C to the individual.

In some embodiments, the second agent is a statin. For example, the statin can be selected from the group consisting of atorvastatin, cerivastatin, fluvastatin, lovastatin, mevastatin, pitavastatin, pravastatin, rosuvastatin, and simvastatin.

In some embodiments, the second agent is selected from the group consisting of fibrates, niacin and analogs thereof, cholesterol absorption inhibitors, bile acid sequestrants, thyroid hormone mimetics, a microsomal triglyceride transfer protein (MTP) inhibitor, a diacylglycerol acyltransferase (DGAT) inhibitor, an inhibitory nucleic acid targeting PCSK9 and an inhibitory nucleic acid targeting apoB100.

In some embodiments, the antibody or antigen binding molecule and the second agent are co-administered as a mixture.

In some embodiments, the antibody or antigen binding molecule and the second agent are co-administered separately.

In some embodiments the antibody is administered intravenously. In some embodiments, the antibody is administered subcutaneously.

DEFINITIONS

An "antibody" refers to a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used in this application, an "antibody" encompasses all variations of antibody and fragments thereof that possess a particular binding specifically, e.g., for PCSK9. Thus, within the scope of this concept are full length antibodies, chimeric antibodies, humanized antibodies, single chain antibodies (ScFv), Fab, Fab', and multimeric versions of these fragments (e.g., F(ab')$_2$) with the same binding specificity.

"Complementarity-determining domains" or "complementarity-determining regions ("CDRs")" interchangeably refer to the hypervariable regions of $V_L$ and $V_H$. The CDRs are the target protein-binding site of the antibody chains that harbors specificity for such target protein. There are three CDRs (CDR1-3, numbered sequentially from the N-terminus) in each human $V_L$ or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, Immunology, 4th ed., Chapter 4. W.H. Freeman & Co., New York, 2000).

The positions of the CDRs and framework regions are determined using various well known definitions in the art, e.g., Kabat, Chothia, international ImMunoGeneTics database (IMGT) (on the worldwide web at imgt.cines.fr/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

The term "binding specificity determinant" or "BSD" interchangeably refer to the minimum contiguous or non-contiguous amino acid sequence within a complementarity determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody.

An "antibody light chain" or an "antibody heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions. In this application, antibody light chains and/or antibody heavy chains may, from time to time, be collectively referred to as "antibody chains." These terms encompass antibody chains containing mutations that do not disrupt the basic structure of $V_L$ or $V_H$, as one skilled in the art will readily recognize.

Antibodies exist as intact immunoglobulins or as a number of well-characterized fragments produced by digestion with various peptidases. Thus, for example, pepsin digests an antibody below the disulfide linkages in the hinge region to produce F(ab')$_2$, a dimer of Fab' which itself is a light chain joined to $V_H$-$C_H$1 by a disulfide bond. The F(ab')$_2$ may be reduced under mild conditions to break the disulfide linkage in the hinge region, thereby converting the F(ab')$_2$ dimer into an Fab' monomer. The Fab' monomer is essentially Fab with part of the hinge region. Paul, Fundamental Immunology 3d ed. (1993). While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., supra; Marks et al., Biotechnology, 10:779-783, (1992)).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332: 323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementarity determining region ("CDR") residues and possibly some framework ("FR") residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

Antibodies or antigen-binding molecules of the invention further includes one or more immunoglobulin chains that are chemically conjugated to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (dAbs), and minibodies.

The various antibodies or antigen-binding fragments described herein can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, as shown in the Examples below, a mouse anti-PCSK9 antibody can be modified by replacing its constant region with the constant region from a human immunoglobulin. Due to the replacement with a human constant region, the chimeric antibody can retain its specificity in recognizing human PCSK9 while having reduced antigenicity in human as compared to the original mouse antibody.

The term "antibody binding molecule" or "non-antibody ligand" refers to antibody mimics that use non-immunoglobulin protein scaffolds, including adnectins, avimers, single chain polypeptide binding molecules, and antibody-like binding peptidomimetics.

The term "variable region" or "V-region" interchangeably refer to a heavy or light chain comprising FR1-CDR1-FR2-CDR2-FR3-CDR3-FR4. See, FIG. 1. An endogenous variable region is encoded by immunoglobulin heavy chain V-D-J genes or light chain V-J genes. A V-region can be naturally occurring, recombinant or synthetic.

As used herein, the term "variable segment" or "V-segment" interchangeably refer to a subsequence of the variable region including FR1-CDR1-FR2-CDR2-FR3. See, FIG. 1. An endogenous V-segment is encoded by an immunoglobulin V-gene. A V-segment can be naturally occurring, recombinant or synthetic.

As used herein, the term "J-segment" refers to a subsequence of the variable region encoded comprising a C-terminal portion of a CDR3 and the FR4. An endogenous J-segment is encoded by an immunoglobulin J-gene. See, FIG. 1. A J-segment can be naturally occurring, recombinant or synthetic.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 94%, 96%, 98%, 99% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under designated immunoassay conditions, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with, e.g., PCSK9 molecules from other species (e.g., mouse) or other PCSK subtypes. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^{-1}$, M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

As used herein, the term "antigen-binding region" refers to a domain of the PCSK9-binding molecule of this invention that is responsible for the specific binding between the molecule and PCSK9. An antigen-binding region includes at least one antibody heavy chain variable region and at least one antibody light chain variable region. There are at least one such antigen-binding regions present in each PCSK9-binding molecule of this invention, and each of the antigen-binding regions may be identical or different from the others. In some embodiments, at least one of the antigen-binding regions of a PCSK9-binding molecule of this invention acts as an antagonist of PCSK9.

The term "antagonist," as used herein, refers to an agent that is capable of specifically binding and inhibiting the activity of the target molecule. For example, an antagonist of PCSK9 specifically binds to PCSK9 and fully or partially inhibits PCSK9-mediated degradation of the LDLR. Inhibiting PCSK9-mediated degradation of the LDLR may or may not interfere with PCSK9 binding to the LDLR. In some cases, a PCSK9 antagonist can be identified by its ability to bind to PCSK9 and inhibit binding of PCSK9 to the LDLR. Inhibition occurs when PCSK9-mediated degradation of the LDLR, when exposed to an antagonist of the invention, is at least about 10% less, for example, at least about 25%, 50%, 75% less, or totally inhibited, in comparison to PCSK9-mediated degradation in the presence of a control or in the absence of the antagonist. A control can be exposed to no antibody or antigen binding molecule, an antibody or antigen binding molecule that specifically binds to another antigen, or an anti-PCSK9 antibody or antigen binding molecule known not to function as an antagonist. An "antibody antagonist" refers to the situation where the antagonist is an inhibiting antibody.

The term "PCSK9" or "proprotein convertase subtilisin/kexin type 9a" interchangeably refer to a naturally-occurring human proprotein convertase belonging to the proteinase K subfamily of the secretory subtilase family. PCSK9 is synthesized as a soluble zymogen that undergoes autocatalytic intramolecular processing in the endoplasmic reticulum, and is thought to function as a proprotein convertase. PCSK9 plays a role in cholesterol homeostasis and may have a role in the differentiation of cortical neurons. Mutations in this the PCSK9 gene have been associated with a form of autosomal dominant familial hypercholesterolemia. See, e.g., Burnett and Hooper, *Clin Biochem Rev* (2008) 29(1):11-26. The nucleic acid and amino acid sequences of PCSK9 are known, and have been published in GenBank Accession Nos. NM_174936.2 and NP_777596.2, respectively. As used herein, a PCSK9 polypeptide functionally binds to LDLR and promotes the degradation of LDLR. Structurally, a PCSK9 amino acid sequence has at least about 90%, 91%, 92%, 93%, 94%, 95%, 96%, 97%, 98%, 99% or 100% sequence identity with the amino acid sequence of GenBank accession no. NP_777596.2. Structurally, a PCSK9 nucleic acid sequence has at least about 90%, 91%, 92%, 93%, 94%, 95%, 96%, 97%, 98%, 99% or 100% sequence identity with the nucleic acid sequence of GenBank accession no. NM_174936.2.

The phrase "PCSK9 gain-of-function mutation" refers to natural mutations occurring in PCSK9 genes that are associated with and/or causative of the familial hypercholesterolemia phenotype, accelerated atherosclerosis and premature coronary heart disease, e.g., due to enhanced LDLR degradation and a reduction of LDLR levels. The allele frequency of PCSK9 gain-of-function mutations is rare. See, Burnett and Hooper, *Clin Biochem Rev.* (2008) 29(1):11-26. Exemplary PCSK9 gain-of-function mutations include D129N, D374H, N425S and R496W. See, Fasano, et al., *Atherosclerosis* (2009) 203(1):166-71. PCSK9 gain-of-function mutations are reviewed, e.g., in Burnett and Hooper, supra; Fasano, et al, supra; Abifadel, et al., *J Med Genet* (2008) 45(12):780-6; Abifadel, et al., *Hum Mutat* (2009) 30(4):520-9; and Li, et al., *Recent Pat DNA Gene Seq* (2009) Nov. 1 (PMID 19601924).

"Activity" of a polypeptide of the invention refers to structural, regulatory, or biochemical functions of a polypeptide in its native cell or tissue. Examples of activity of a polypeptide include both direct activities and indirect activities. Exemplary direct activities of PCSK9 are the result of direct interaction with the polypeptide, including binding to LDLR and PCSK9-mediated degradation of LDLR. Exemplary indirect activities in the context of PCSK9 are observed as a change in phenotype or response in a cell, tissue, organ or subject to a polypeptide's directed activity, e.g., reducing increased liver LDLR, reduced plasma HDL-C, decreased plasma cholesterol, enhances sensitivity to statins.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The invention provides polypeptides or polynucleotides that are substantially identical to the polypeptides or polynucleotides, respectively, exemplified herein (e.g., the variable regions exemplified in any one of SEQ ID NOS:1-5, 15-19 and 40-41; the variable segments exemplified in any one of SEQ ID NOS:27-31; the CDRs exemplified in any one of SEQ ID NOS:6-14, 20-26; the FRs exemplified in any one of SEQ ID NOs: 32-39; and the nucleic acid sequences exemplified in any on of SEQ ID NOS:42-45). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "link," when used in the context of describing how the antigen-binding regions are connected within a PCSK9-binding molecule of this invention, encompasses all possible means for physically joining the regions. The multitude of antigen-binding regions are frequently joined by chemical bonds such as a covalent bond (e.g., a peptide bond or a disulfide bond) or a non-covalent bond, which can be either a direct bond (i.e., without a linker between two antigen-binding regions) or indirect bond (i.e., with the aid of at least one linker molecule between two or more antigen-binding regions).

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

The term "therapeutically acceptable amount" or "therapeutically effective dose" interchangeably refer to an amount sufficient to effect the desired result (i.e., a reduction in plasma non-HDL-C, hypercholesterolemia, atherosclerosis, coronary heart disease). In some embodiments, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of a PCSK9 antagonizing antibody of the invention can prevent the onset of, or result in a decrease in severity of, respectively, disease symptoms associated with the presence of PCSK9 (e.g., hypercholesterolemia). Said terms can also promote or increase, respectively, frequency and duration of periods free from disease symptoms. A "prophylactically effective dosage," and a "therapeutically effective dosage," can also prevent or ameliorate, respectively, impairment or disability due to the disorders and diseases resulting from activity of PCSK9.

The term "co-administer" refers to the simultaneous presence of two active agents in the blood of an individual. Active agents that are co-administered can be concurrently or sequentially delivered.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than an antagonist anti PCSK9 antibody of the invention. In some embodiments, the phrase "consisting essentially of" expressly excludes the inclusion of one or more additional active agents other than an antagonist anti PCSK9 antibody of the invention and a second co-administered agent.

The term "statin" refers to a class of pharmacological agents that are competitive inhibitors of 3-hydroxy-3-methylglutaryl coenzyme A (HMG-CoA) reductase.

BRIEF DESCRIPTION OF THE DRAWINGS

FIG. 1 illustrates the heavy (SEQ ID NO:1) and light (SEQ ID NO:15) chain amino acid sequences of parent mouse monoclonal antibody NVP-LFU720. The sequences of CDR1, CDR2 and CDR3 are underlined and in bold.

FIG. 2 illustrates the heavy (SEQ ID NO:2) and light (SEQ ID NO:16) chain amino acid sequences of parent mouse monoclonal antibody NVP-LGT209. The sequences of CDR1, CDR2 and CDR3 are underlined and in bold.

FIG. 3 illustrates the heavy (SEQ ID NO:2) and light (SEQ ID NO:18) chain amino acid sequences of parent mouse monoclonal antibody NVP-LGT210. The sequences of CDR1, CDR2 and CDR3 are underlined and in bold.

FIG. 4 illustrates the heavy (SEQ ID NO:4) and light (SEQ ID NO:16) chain amino acid sequences of parent mouse monoclonal antibody NVP-LGT211. The sequences of CDR1, CDR2 and CDR3 are underlined and in bold.

FIGS. 5A-C illustrate ELISA assay testing of binding of NVP-LGT209 (A), NVP-LGT210 (B) and NVP-LGT-211 (C) in comparison to NVP-LFU720-NX-4 to several different human and mouse antigens.

For LDL-uptake assays, PCSK9-binding antibodies were incubated for 30 min at room temperature in DMEM containing 10% fetal bovine lipoprotein-deficient serum (Intracel) and 200 nM human PCSK9 (Hampton et al. PNAS (2007) 104:14604-14609), and the antibody/PCSK9/media solutions were added to cells in 96-well plates and incubated overnight. The following day, 1,1'-dioctadecyl-3,3,3',3'-tetramethyl-indocarbocyanine perchlorate-labeled LDL (DiI-LDL, Biomedical Technologies) was added for an additional 2 h. Medium was then aspirated, cells washed three times with PBS, and cells dissociated with 0.25% trypsin-EDTA. Cells were then transferred into FACS buffer (PBS containing 5% fetal bovine serum, 2 mM EDTA and 0.2% sodium azide), centrifuged at 1000×g for 10 min, aspirated, and fixed in 1% paraformaldehyde. LDL uptake was measured by cellular DiI fluorescence (excitation at 488 nm and emission at 575 nm) using flow cytometry (Becton Dickinson LSR II). For surface LDL-R assays, cells were incubated with serum-free media containing antibodies, washed with PBS, and harvested in Versine (Biowhittaker, 17-771E) and FACS buffer. The cells were transferred to new plates, centrifuged at 1200 rpm for 5 m, and blocked with normal rabbit IgG (MP biomedicals). Cells were labeled with rabbit-anti-hLDL-R-Alexa 647 IgG (5 µg/ml) labeled antibodies in FACS buffer, centrifuged, washed, and fixed in 1% paraformaldehyde. Surface LDL-R was measured by flow cytometry (excitation of 488 nm and emission of 633 nm). $EC_{50}$s were calculated using Prism (GraphPad).

Figure 10:
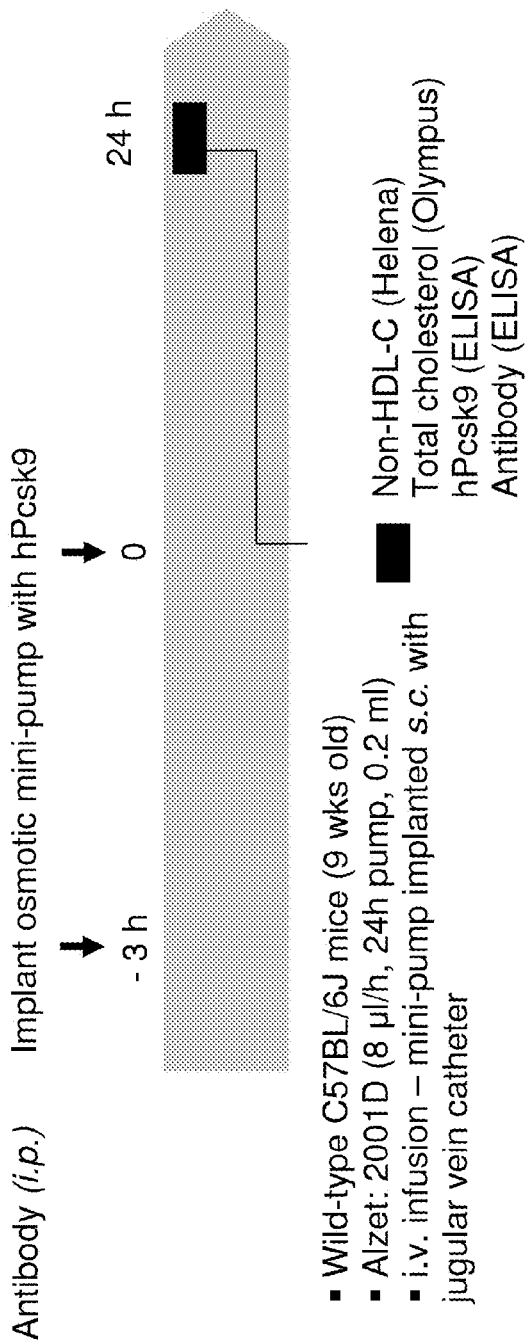

FIG. 10 provides a schematic of the study design for the human PCSK9 infusion mouse model to determine the cholesterol lowering effect of the present antibodies. LGT209, LGT210, and LGT211 are Humaneered™ anti-PCSK9 antibodies that bind with high affinity to hPCSK9 with no detectable binding to murine PCSK9. To test whether LGT209, LGT210, or LGT211 could both inhibit hPCSK9-mediated elevation of non-HDL cholesterol and prevent PCSK9-mediated degradation of hepatic LDLR, the antibodies were each injected into mice 3 h before osmotic mini-pump implantation containing hPCSK9 (for continuous infusion). Plasma and liver tissue harvest were performed 24 h after hPCSK9 injection.

FIG. 11 shows that treatment with antibodies LGT209, LGT210 and LGT211 resulted in accumulation of human PCSK9 ("hPCSK9") in the infusion mouse model. Briefly, total hPCSK9 was measured by ELISA using mAb 7D16 for capture. mAb 7D16 binds a different epitope on PCSK9 than LGT209, LGT210 and LGT211 and can be used to measure total (free and bound) PCSK9. The observed increase in total hPCSK9 is presumably due to an increase in hPCSkK9/Ab complexes. Free antibody was measured by ELISA using hPCSK9 for capture. This assay measured "free" antibody and possibly measures 1:1 Ab:PCSK9 complexes. C57BL/6 mice were treated with vehicle alone, PCSK9 alone, PCSK9+ 20 mg/kg LGT210, PCSK9+20 mg/kg NVP-LGT211, or mouse non-specific IgG mixture (negative control). Individual data points are plotted and the mean value is demarcated by a horizontal bar; p<0.05 was considered significant.

Plasma IgG levels were quantified by Meso Scale Discovery (MSD) assay. Free antibody was measured using hPCSK9 for capture. This assay measured "free" antibody and possibly measures 1:1 Ab:PCSK9 complexes. For IgG MSD assay, MSD Standard 96 plates (L11XA-3) were used. Briefly, plates were coated with 25 to 28 µl capture antigen, PCSK9-His, 1 µg/ml in PBS (25-28 ng/well) overnight at 4° C. The coating solution was removed and the plates were blocked with 150 µl/well of 5% MSD Blocker A (R93AA-2) shaking for 1 h at room temperature. After washing the plate with PBS+0.05% Tween-20 300 µl×3 times, 25 µl of IgG calibrator dilutions (10 series dilutions with MSD blocker A from 10,000 to 0.0003 ng/ml), unknown plasma sample dilutions (10,000× with MSD blocker A), or quality control samples were added and incubated with shaking for 1 h at room temperature. After washing, 25 µl/well of 1 µg/ml detection antibody (MSD goat anti-mouse SULFO-TAG Labeled detection antibody, R32AC-5, diluted with 1% BSA/PBS/0.05% Tween 20) was added and incubated with shaking for 1 h at room temperature. After wash and addition of 150 μl/well 1× read buffer T, plate was read immediately on MSD SECTOR Imager 6000. A plot of the standard curve and unknown samples were calculated using MSD data analysis software.

Both plasma IgG and hPCSK9 levels were quantified by Meso Scale Discovery (MSD) assay. The MSD hPCSK9 assay is similar to IgG assay, but with the following exceptions. The plates were coated with 25-28 μl capture antibody (7D16.C3: 2.95 mg/ml) at 1 μg/ml. mAb 7D16 binds a different epitope on PCSK9 than LGT209, LGT210 and LGT211 and can be used to measure total (free and bound) PCSK9. After blocking the plates, 25 μl of hPCSK9 calibrator dilutions (10 points from 10,000 to 0.0003 ng/ml) and plasma sample dilutions (10,000× with MSD blocker A) were incubated with shaking for 1 h at room temperature followed by incubation with primary detection antibody (rabbit anti-PCSK9 polyclonal antibody, Ab4, in house Rabbit ID #RB11835). An incubation step with secondary detection antibody (MSD goat anti-rabbit SULFO-TAG Labeled detection antibody, R32AB-5) was added before reading with MSD SECTOR Imager 6000. The observed increase in total hPCSK9 is presumably due to an increase in hPCSkK9/Ab complexes. Statistical analysis of was performed using GraphPad Prism 4.02 (GraphPad software, San Diego, Calif.). One-way ANOVA was used to analyze group differences and when overall differences were found Newman-Keuls post hoc test was used to determine specific differences amongst treated groups.

Figure 12:
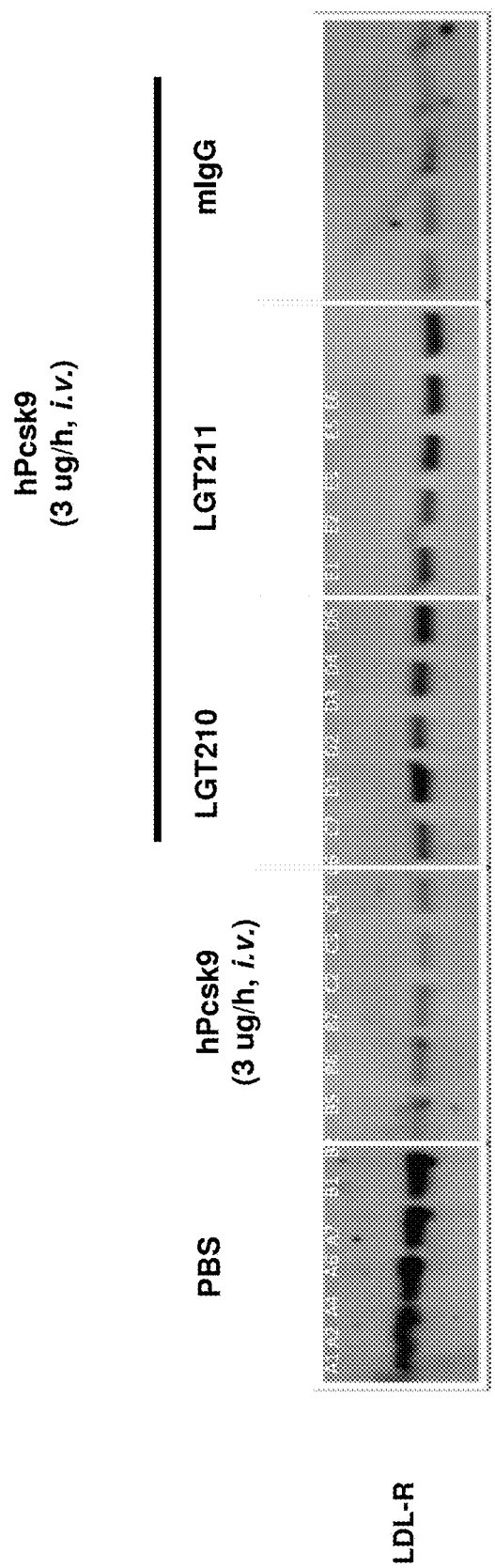

FIG. 12 illustrates that antibodies LGT209, LGT210 and LGT211 lead to protection of liver LDL-R from hPCSK9-mediated degradation in the infusion mouse model. C57BL/6 mice were treated with vehicle alone, PCSK9 alone, PCSK9+20 mg/kg LGT210, PCSK9+20 mg/kg NVP-LGT211, or mouse non-specific IgG mixture (negative control). Liver samples from individual animals are shown.

Polyacrylamide gel electrophoresis of plasma membrane samples was performed using a 20-lane 4-12% Bis-Tris Invitrogen Midi gel (Invitrogen WG1402BX10) with MOPS running buffer (Invitrogen NP0001). Prepared samples were heated at 70° C. for 10 minutes, placed on ice, and then a Matrix multi-channel pipettor was used to load 10 μl of each sample onto a gel. SeeBlue Plus2 markers (Invitrogen LC5925) were loaded alongside the samples for size determination and gel orientation. The gels were run at a constant voltage of 200V until the dye front reached the bottom of the gel. After electrophoresis, the gels were transferred to nitrocellulose membranes (Invitrogen IB3010-01) using an iBlot unit (Invitrogen IB1001EU). Transfer was performed at 20V for 7 min. After transfer, the membranes were blocked with Pierce Superblock T20 (Pierce 37536) for at least 30 min. Membranes were placed in "seal-a-meal" bags, and then a 1:500 dilution of rabbit anti-LDLR antibody in Superblock was added before overnight incubation at 4° C. with rocking. Membranes were rinsed in TBS/0.05% Tween 5 times for 5 minutes with rocking, and then a 1:30,000 dilution of goat anti-rabbit HRP secondary antibody in Superblock was added to the membranes for 1 h. Membranes were again rinsed in TBS/0.05% Tween 5 times for 5 minutes with rocking. The HRP-conjugate was detected using a Pierce SuperSignal West Pico Chemiluminescent Substrate (Pierce 37079) according to the manufacturer's directions. Briefly, equal parts Peroxide Solution and Luminol/Enhancer Solution were mixed and added to the membranes (0.2 ml/cm$^2$) for 5 min. Excess solution was removed by blotting, and the membranes were exposed to Kodak BioMax MR X-ray film (Kodak 870 1302) for exposure.

Figure 13:
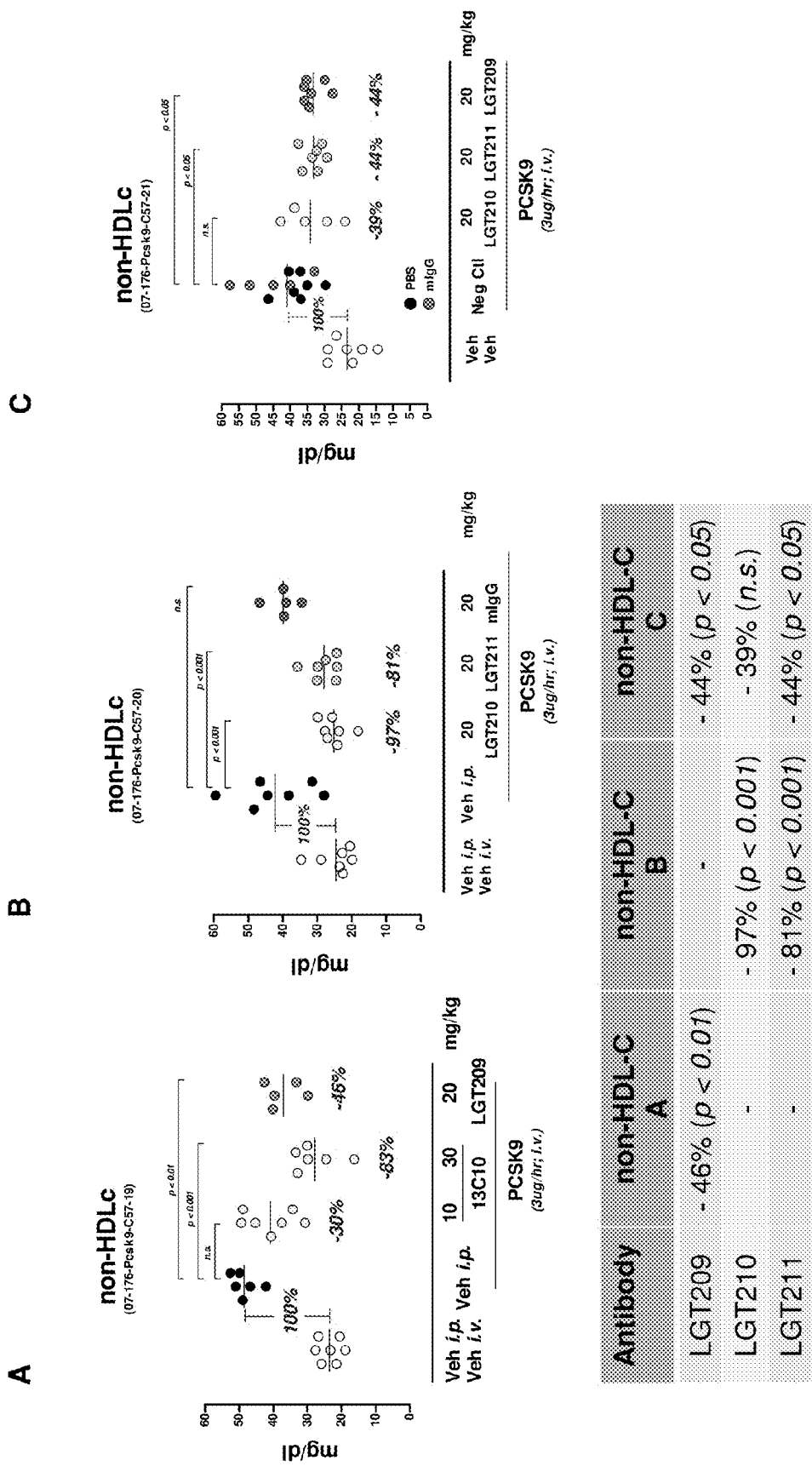

FIGS. 13A-C illustrate that antibodies LGT209, LGT210 and LGT211 lead to reduction in plasma non-HDL-cholesterol in the hPCSK9 infusion mouse model. Pre-injection of LGT209 antibody resulted in a 46% protection from hPCSK9-mediated elevation in non-HDL cholesterol. Pre-injection of LGT210 or LGT211 resulted in equivalent or greater protection from hPCSK9-mediated elevation in non-HDL cholesterol. 13C10 is a validated murine anti-PCSK9 antibody that binds with high affinity to hPCSK9 and was used as a positive control for this assay. C57BL/6 mice were treated with vehicle alone, PCSK9 alone, PCSK9+20 mg/kg LGT209, PCSK9+20 mg/kg LGT210, PCSK9+20 mg/kg NVP-LGT211, PCSK9+20 mg/kg 13C10 or mouse non-specific IgG mixture (negative control). Individual values are shown with mean value demarcated as a horizontal bar. To quantify plasma total cholesterol level, Olympus clinical analyzer (Olympus America Inc.: Olympus AU400) was used. Plasma samples were diluted 1:3 in ddH2O and 40 μl of diluted plasma samples were quantified for total cholesterol level according to the manufacturer's directions. To quantify plasma HDL and non-HDL, lipoprotein cholesterol fractions were obtained using Spife 3000 from Helena Laboratories. All procedures, including sample preparation, gel preparation, sample application, gel electrophoresis, staining, washing, and drying were following the instructions provided in the operator's manual. The gel was then scanned in the Quick Scan 2000 using Slit 5 and the relative percentage of the lipoprotein cholesterol fractions was calculated using Helena densitometer. Finally, the absolute values of HDL and non-HDL were calculated by multiplication of the percentage of each fraction and total cholesterol levels.

Figure 14:
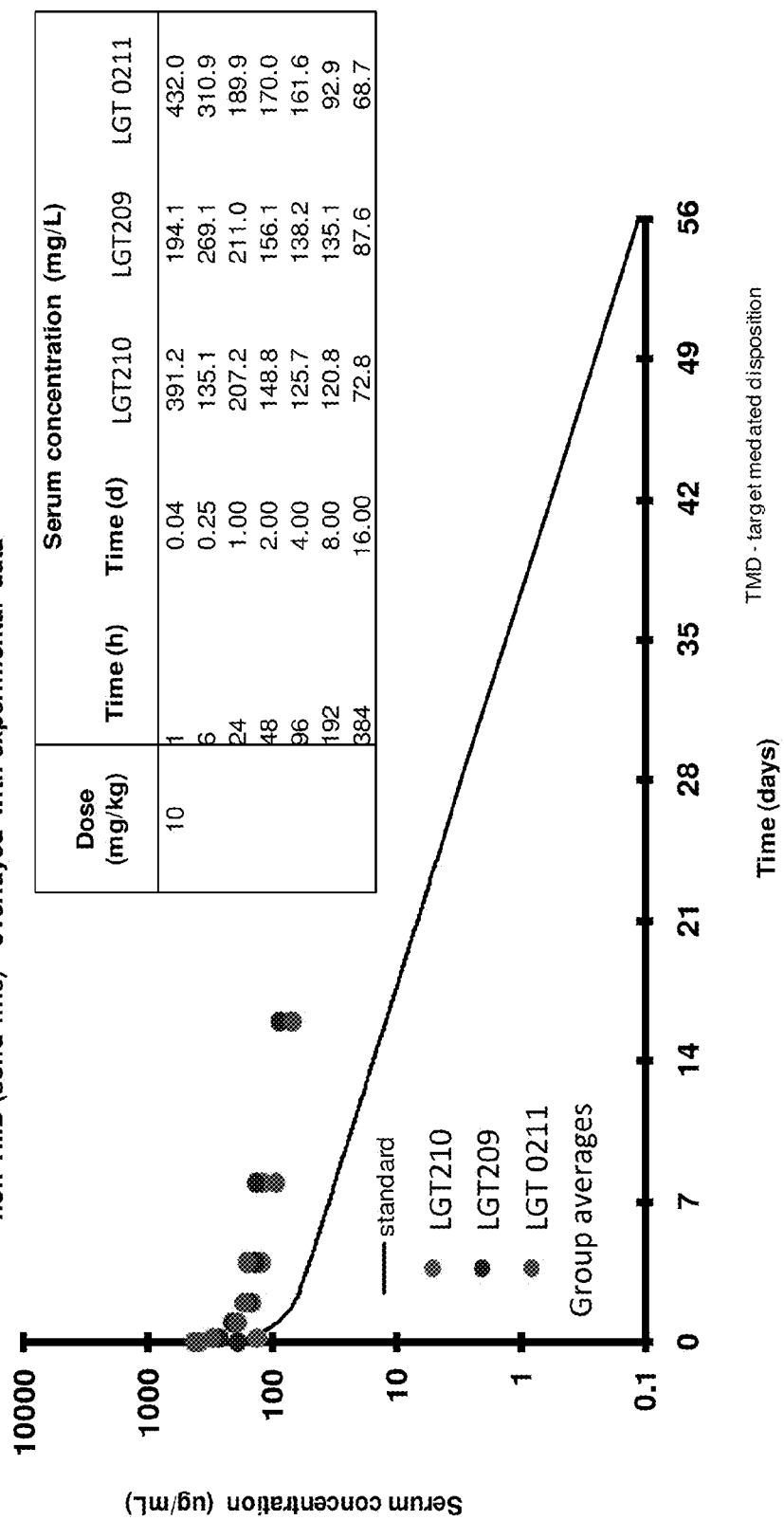

FIG. 14 illustrates rat pharmacokinetic (PK) profiles for antibodies LGT209, LGT210 and LGT211 (human IgG1-silent) in comparison with a "typical" IgG1 (PK) profile. The half-life of antibodies LGT209, LGT210 and LGT211 is markedly longer (7-13 days) in comparison to a typical IgG1 half-life (about 6 days) (e.g., as determined in a human subject). There was no evidence of target mediated disposition (TMD), indicating that the antibodies are not cross-reactive with rodent PCSK9). For each test antibody, 3 male Lewis rats were injected at 10 mgs/kg. At time=0, 1, 6, 24 h, 2, 4, 8 and 16 days, 250 μl of blood was sampled, and the cleared plasma diluted and evaluated in a capture ELISA (goat anti-human IgG) to measure total human antibody recovered. A standard curve was also generated for each test antibody. The quantity of the recovered IgG was graphed versus the expected recovery of a typical human IgG in a rat.

DETAILED DESCRIPTION

1. Introduction

The antibodies and antigen-binding molecules of the present invention specifically bind to proprotein convertase subtilisin/kexin type 9a ("PCSK9"). The present anti-PCSK9 antibodies and antigen-binding molecules bind to the C-terminus of PCSK9 and have the unexpected property of interfering with PCSK9-mediated degradation of the low density lipoprotein receptor (LDL-R) without interfering with binding of PCSK9 to the LDL-R. In particular, the anti-PCSK9 antibodies and antigen binding molecules bind to an epitope within residues 680-692 of PCSK9, for example, an epitope within the amino acid sequence RSRHLAQASQELQ (SEQ ID NO:49), located at the C-terminal end of PCSK9. Because the antibodies and antigen-binding molecules of the invention bind to PCSK9 while bound on a cell rather than only to circulating PCSK9, they have a comparatively longer in vivo half-life in a patient, e.g., at least about 7 days or longer, and in some embodiments, provide lipid-lowering effects for at least 2 weeks after administration. The anti-PCSK9 antibodies and antigen binding molecules of the invention are antagonists of PCSK9 in that they prevent, reduce and/or inhibit PCSK9-mediated degradation of the LDL-R, thereby facilitating increased uptake of low density lipoprotein cholesterol (LDL-C). The anti-PCSK9 antibodies and antigen binding molecules find use in treating subjects suffering from, e.g., dyslipidemia, hypercholesterolemia, triglyceridemia and other PCSK9-mediated disease conditions.

2. Improved Anti-PCSK9 Antibodies Generally

Anti-PCSK9 antibody fragments can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc. When present, the constant regions of the anti-PCSK9 antibodies can be any type or subtype, as appropriate, and can be selected to be from the species of the subject to be treated by the present methods (e.g., human, non-human primate or other mammal, for example, agricultural mammal (e.g., equine, ovine, bovine, porcine, camelid), domestic mammal (e.g., canine, feline) or rodent (e.g., rat, mouse, hamster, rabbit). In some embodiments the anti-PCSK9 antibodies are humanized or Humaneered™ In some embodiments, the constant region isotype is IgG, for example, IgG1. In some embodiments, the human IgG1 constant region is mutated to have reduced binding affinity for an effector ligand such as Fc receptor (FcR), e.g., Fc gamma R1, on a cell or the C1 component of complement. See, e.g., U.S. Pat. No. 5,624, 821. Antibodies containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to Ala234 and Ala235. The numbering of the residues in the heavy chain constant region is that of the EU index (see, Kabat, et al., (1983) "Sequences of Proteins of Immunological Interest," U.S. Dept. Health and Human Services). See also, e.g., Woodle, et al, *Transplantation* (1999) 68(5):608-616; Xu, et al., *Cell Immunol* (2000) 200(1):16-26; and Hezareh, et al., *J Virol* 75(24):12161-8.

Anti-PCSK9 antibodies or antigen-binding molecules of the invention also include single domain antigen-binding units which have a camelid scaffold. Animals in the camelid family include camels, llamas, and alpacas. Camelids produce functional antibodies devoid of light chains. The heavy chain variable (VH) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies. Camelid scaffold-based anti-PCSK9 molecules with binding specificities of the anti-PCSK9 antibodies exemplified herein can be produced using methods well known in the art, e.g., Dumoulin et al., Nature Struct. Biol. 11:500-515, 2002; Ghahroudi et al., FEBS Letters 414:521-526, 1997; and Bond et al., J Mol. Biol. 332: 643-55, 2003.

The improved anti-PCSK9 antibodies of the invention are engineered human antibodies with V-region sequences having substantial amino acid sequence identity to human germline V-region sequences while retaining the specificity and affinity of a reference antibody. See, U.S. Patent Publication No. 2005/0255552 and U.S. Patent Publication No. 2006/0134098, both of which are hereby incorporated herein by reference. The process of improvement identifies minimal sequence information required to determine antigen-binding specificity from the variable region of a reference antibody, and transfers that information to a library of human partial V-region gene sequences to generate an epitope-focused library of human antibody V-regions. A microbial-based secretion system can be used to express members of the library as antibody Fab fragments and the library is screened for antigen-binding Fabs, for example, using a colony-lift binding assay. See, e.g., U.S. Patent Publication No. 2007/0020685. Positive clones can be further characterized to identify those with the highest affinity. The resultant engineered human Fabs retain the binding specificity of the parent, reference anti-PCSK9 antibody, typically have equivalent or higher affinity for antigen in comparison to the parent antibody, and have V-regions with a high degree of sequence identity compared with human germ-line antibody V-regions.

The minimum binding specificity determinant (BSD) required to generate the epitope-focused library is typically represented by a sequence within the heavy chain CDR3 ("CDRH3") and a sequence within the light chain of CDR3 ("CDRL3"). The BSD can comprise a portion or the entire length of a CDR3. The BSD can be comprised of contiguous or non-contiguous amino acid residues. In some cases, the epitope-focused library is constructed from human V-segment sequences linked to the unique CDR3-FR4 region from the reference antibody containing the BSD and human germ-line J-segment sequences (see, U.S. Patent Publication No. 2005/0255552). Alternatively, the human V-segment libraries can be generated by sequential cassette replacement in which only part of the reference antibody V-segment is initially replaced by a library of human sequences. The identified human "cassettes" supporting binding in the context of residual reference antibody amino acid sequences are then recombined in a second library screen to generate completely human V-segments (see, U.S. Patent Publication No. 2006/0134098).

In each case, paired heavy and light chain CDR3 segments, CDR3-FR4 segments, or J-segments, containing specificity determinants from the reference antibody, are used to constrain the binding specificity so that antigen-binders obtained from the library retain the epitope-specificity of the reference antibody. Additional maturational changes can be introduced in the CDR3 regions of each chain during the library construction in order to identify antibodies with optimal binding kinetics. The resulting engineered human antibodies have V-segment sequences derived from the human germ-line libraries, retain the short BSD sequence from within the CDR3 regions and have human germ-line framework 4 (FR4) regions.

Accordingly, in some embodiments, the anti-PCSK9 antibodies contain a minimum binding sequence determinant (BSD) within the CDR3 of the heavy and light chains derived from the originating or reference monoclonal antibody. The remaining sequences of the heavy chain and light chain variable regions (CDR and FR), e.g., V-segment and J-segment, are from corresponding human germline and affinity matured amino acid sequences. The V-segments can be selected from a human V-segment library. Further sequence refinement can be accomplished by affinity maturation.

In another embodiment, the heavy and light chains of the anti-PCSK9 antibodies contain a human V-segment from the corresponding human germline sequence (FR1-CDR1-FR2-CDR2-FR3), e.g., selected from a human V-segment library, and a CDR3-FR4 sequence segment from the originating monoclonal antibody. The CDR3-FR4 sequence segment can be further refined by replacing sequence segments with corresponding human germline sequences and/or by affinity maturation. For example, the FR4 and/or the CDR3 sequence surrounding the BSD can be replaced with the corresponding human germline sequence, while the BSD from the CDR3 of the originating monoclonal antibody is retained.

In some embodiments, the corresponding human germline sequence for the heavy chain V-segment is Vh1-02. In some embodiments, the corresponding human germline sequence for the heavy chain J-segment is JH4. In some embodiments, the heavy chain J-segment comprises the human germline JH4 partial sequence WGQGTLVTVSS (SEQ ID NO:50). The full-length J-segment from human germline JH4 is YFDYWGQGTLVTVSS (SEQ ID NO:51). The variable region genes are referenced in accordance with the standard nomenclature for immunoglobulin variable region genes. Current immunoglobulin gene information is available through the worldwide web, for example, on the ImMunoGeneTics (IMGT), V-base and PubMed databases. See also, Lefranc, *Exp Clin Immunogenet*. 2001; 18(2):100-16; Lefranc, *Exp Clin Immunogenet*. 2001; 18(3):161-74; *Exp Clin Immunogenet*. 2001; 18(4):242-54; and Giudicelli, et al., *Nucleic Acids Res*. 2005 Jan. 1; 33 (Database issue):D256-61.

In some embodiments, the corresponding human germline sequence for the light chain V-segment is VK3 L6. In some embodiments, the corresponding human germline sequence for the light chain J-segment is Jk2. In some embodiments, the light chain J-segment comprises the human germline Jk2 partial sequence FGQGTKLEIK (SEQ ID NO:52). The full-length J-segment from human germline Jk2 is YTFGQGTKLEIK (SEQ ID NO:53).

In some embodiments, the heavy chain V-segment has at least 85%, 89%, 90%, 93%, 95%, 96%, 97%, 98%, 99% or 100% sequence identity to the amino acid sequence QVQLVQSGAEVKKPGASVKVSCKASGYTFS(D/T)MYMSWVRQAPGQGLEWMGRIDPAN(A/E/G)HTNY(A/D)(P/Q)KFQ(A/G)RVTMTRDTSISTAYMELSRLTSDDTAVYYCAR (SEQ ID NO:28). In some embodiments, the heavy chain V-segment has at least 85%, 89%, 90%, 93%, 95%, 96%, 97%, 98%, 99% or 100% sequence identity to the amino acid sequence QVQLVQSGAEVKKPGASVKVSCKASGYTFSTMYMSWVRQAPGQGLEWMGRIDPANEHTNYAQKFQGRVTMTRDTSISTAYMELSRLTSDDTAVYYCAR (SEQ ID NO:27).

In some embodiments, the light chain V-segment has at least 85%, 89%, 90%, 93%, 95%, 96%, 97%, 98%, 99% or 100% sequence identity to the amino acid sequence (E/Q)IV(L/M)TQSPATLSVSPGERATLSC(R/S)AS(Q/S)SVSYMHWYQQKPGQAPRLLIY(G/L)(T/V)F(N/R)(L/R)A(S/T)GIPDRFSGSGSGTDFTLTIGRLEPEDFAVYYC (SEQ ID NO:31). In some embodiments, the heavy chain V-segment has at least 85%, 89%, 90%, 93%, 95%, 96%, 97%, 98%, 99% or 100% sequence identity to the amino acid sequence QIVLTQSPATLSVSPGERATLSCRASQSVSYMHWYQQKPGQAPRLLIYGVFRRATGIPDRFSGSGSGTDFTLTIGRLEPEDFAVYYC (SEQ ID NO:29). In some embodiments, the heavy chain V-segment has at least 85%, 89%, 90%, 93%, 95%, 96%, 97%, 98%, 99% or 100% sequence identity to the amino acid sequence EIVMTQSPATLSVSPGERATLSCRASQSVSYMHWYQQKPGQAPRLLIYGVFRRATGIPDRFSGSGSGTDFTLTIGRLEPEDFAVYYC (SEQ ID NO:30).

In some embodiments:
  i) the heavy chain CDR3 comprises the amino acid sequence SYYYY(A/N)MD(A/F/S/V/Y) (SEQ ID NO:14); and
  ii) the light chain CDR3 variable region comprises the amino acid sequence LQWSSDPPT (SEQ ID NO:26).

In some embodiments:
  i) the heavy chain CDR3 comprises the amino acid sequence selected from the group consisting of SEQ ID NO:12 and SEQ ID NO:13; and
  ii) the light chain CDR3 comprises the amino acid sequence of SEQ ID NO:26.

In some embodiments, the antibodies of the invention comprise a heavy chain variable region comprising a CDR1 comprising an amino acid sequence (D/T)MYMS (SEQ ID NO:8); a CDR2 comprising an amino acid sequence RIDPAN(A/E/G)HTNY(A/D)(P/Q)KFQ(A/G) (SEQ ID NO:11); and a CDR3 comprising an amino acid sequence of SYYYY(A/N)MD(A/F/S/V/Y) (SEQ ID NO:14).

In some embodiments, the antibodies of the invention comprise a light chain variable region comprising a CDR1 comprising an amino acid sequence (R/S)AS(Q/S)SVSYMH (SEQ ID NO:22); a CDR2 comprising an amino acid sequence (G/L)(T/V)F(N/R)(L/R)A(S/T) (SEQ ID NO:25); and a CDR3 comprising an amino acid sequence of LQWSSDPPT (SEQ ID NO:26).

In some embodiments, the heavy chain variable region comprises a FR1 comprising the amino acid sequence of SEQ ID NO:32; a FR2 comprising the amino acid sequence of SEQ ID NO:33; a FR3 comprising the amino acid sequence of SEQ ID NO:34; and a FR4 comprising the amino acid sequence of SEQ ID NO:35. The identified amino acid sequences may have one or more substituted amino acids (e.g., from affinity maturation) or one or two conservatively substituted amino acids.

In some embodiments, the light chain variable region comprises a FR1 comprising an amino acid sequence of SEQ ID NO:36; a FR2 comprising the amino acid sequence of SEQ ID NO:37; a FR3 comprising the amino acid sequence of SEQ ID NO:38; and a FR4 comprising the amino acid sequence of SEQ ID NO:39. The identified amino acid sequences may have one or more substituted amino acids (e.g., from affinity maturation) or one or two conservatively substituted amino acids.

Over their full length, the variable regions of the anti-PCSK9 antibodies of the present invention generally will have an overall variable region (e.g., FR1-CDR1-FR2-CDR2-FR3-CDR3-FR4) amino acid sequence identity of at least about 85%, for example, at least about 89%, 90%, 91%, 92%, 93%, 94%, 95%, 96%, 97%, 98%, 99% or 100% to the corresponding human germline variable region amino acid sequence. For example, the heavy chain of the anti-PCSK9 antibodies can have at least about 85%, 89%, 90%, 91%, 92%, 93%, 94%, 95%, 96%, 97%, 98%, 99% or 100% amino acid sequence identity to the human germline variable region Vh1-02. The light chain of the anti-PCSK9 antibodies can have at least about 85%, 89%, 90%, 91%, 92%, 93%, 94%, 95%, 96%, 97%, 98%, 99% or 100% amino acid sequence identity to the human germline variable region VK3 L6. In some embodiments, only amino acids within the framework regions are added, deleted or substituted. In some embodiments, the sequence identity comparison excludes the CD3.

In some embodiments, the anti-PCSK9 antibodies of the invention comprise a heavy chain variable region having at least 85%, 89%, 90%, 91%, 92%, 93%, 94%, 95%, 96%, 97%, 98%, 99% or 100% amino acid sequence identity to a heavy chain variable region of SEQ ID NO:40 and comprise a light chain variable region having at least 85%, 89%, 90%, 91%, 92%, 93%, 94%, 95%, 96%, 97%, 98%, 99% or 100% amino acid sequence identity to a light chain variable region of SEQ ID NO:41 (i.e., consensus sequences).

In some embodiments, the anti-PCSK9 antibodies of the invention comprise a heavy chain variable region having at least 85%, 89%, 90%, 91%, 92%, 93%, 94%, 95%, 96%, 97%, 98%, 99% or 100% amino acid sequence identity to a heavy chain variable region of SEQ ID NO:1 and comprise a light chain variable region having at least 85%, 89%, 90%, 91%, 92%, 93%, 94%, 95%, 96%, 97%, 98%, 99% or 100% amino acid sequence identity to a light chain variable region of SEQ ID NO:15 (i.e., mouse LFU720).

In some embodiments, the anti-PCSK9 antibodies of the invention comprise a heavy chain variable region having at least 85%, 89%, 90%, 91%, 92%, 93%, 94%, 95%, 96%, 97%, 98%, 99% or 100% amino acid sequence identity to a heavy chain variable region of SEQ ID NO:2 and comprise a light chain variable region having at least 85%, 89%, 90%, 91%, 92%, 93%, 94%, 95%, 96%, 97%, 98%, 99% or 100% amino acid sequence identity to a light chain variable region of SEQ ID NO:16 (i.e., LGT-209).

In some embodiments, the anti-PCSK9 antibodies of the invention comprise a heavy chain variable region having at least 85%, 89%, 90%, 91%, 92%, 93%, 94%, 95%, 96%, 97%, 98%, 99% or 100% amino acid sequence identity to a heavy chain variable region of SEQ ID NO:2 and comprise a light chain variable region having at least 85%, 89%, 90%, 91%, 92%, 93%, 94%, 95%, 96%, 97%, 98%, 99% or 100% amino acid sequence identity to a light chain variable region of SEQ ID NO:18 (i.e., LGT-210).

In some embodiments, the anti-PCSK9 antibodies of the invention comprise a heavy chain variable region having at least 85%, 89%, 90%, 91%, 92%, 93%, 94%, 95%, 96%, 97%, 98%, 99% or 100% amino acid sequence identity to a heavy chain variable region of SEQ ID NO:4 and comprise a light chain variable region having at least 85%, 89%, 90%, 91%, 92%, 93%, 94%, 95%, 96%, 97%, 98%, 99% or 100% amino acid sequence identity to a light chain variable region of SEQ ID NO:16 (i.e., LGT-211).

In some embodiments, the anti-PCSK9 antibodies of the invention comprise a heavy chain polypeptide having at least 85%, 89%, 90%, 91%, 92%, 93%, 94%, 95%, 96%, 97%, 98%, 99% or 100% amino acid sequence identity to a heavy chain variable region of SEQ ID NO:3 and comprise a light chain polypeptide having at least 85%, 89%, 90%, 91%, 92%, 93%, 94%, 95%, 96%, 97%, 98%, 99% or 100% amino acid sequence identity to a light chain variable region of SEQ ID NO:17 (i.e., LGT-209).

In some embodiments, the anti-PCSK9 antibodies of the invention comprise a heavy chain polypeptide having at least 85%, 89%, 90%, 91%, 92%, 93%, 94%, 95%, 96%, 97%, 98%, 99% or 100% amino acid sequence identity to a heavy chain variable region of SEQ ID NO:3 and comprise a light chain polypeptide having at least 85%, 89%, 90%, 91%, 92%, 93%, 94%, 95%, 96%, 97%, 98%, 99% or 100% amino acid sequence identity to a light chain variable region of SEQ ID NO:19 (i.e., LGT-210).

In some embodiments, the anti-PCSK9 antibodies of the invention comprise a heavy chain polypeptide having at least 85%, 89%, 90%, 91%, 92%, 93%, 94%, 95%, 96%, 97%, 98%, 99% or 100% amino acid sequence identity to a heavy chain variable region of SEQ ID NO:5 and comprise a light chain polypeptide having at least 85%, 89%, 90%, 91%, 92%, 93%, 94%, 95%, 96%, 97%, 98%, 99% or 100% amino acid sequence identity to a light chain variable region of SEQ ID NO:17 (i.e., LGT-211).

For identified amino acid sequences less than 20 amino acids in length, one or two conservative amino acid residue substitutions can be tolerated while still retaining the desired specific binding and/or antagonist activity.

The anti-PCSK9 antibodies of the present invention generally will bind PCSK9 with an equilibrium dissociation constant ($K_D$) of less than about $10^{-8}$ M or $10^{-9}$ M, for example, less than about $10^{-10}$ M or $10^{-11}$ M, in some embodiments less than about $10^{-12}$ M or $10^{-13}$ M.

The anti-PCSK9 antibodies optionally can be multimerized and used according to the methods of this invention. The anti-PCSK9 antibodies can be a full-length tetrameric antibody (i.e., having two light chains and two heavy chains), a single chain antibody (e.g., a scFv), or a molecule comprising antibody fragments that form one or more antigen-binding sites and confer PCSK9-binding specificity, e.g., comprising heavy and light chain variable regions (for instance, Fab' or other similar fragments).

The invention further provides polynucleotides encoding the antibodies described herein, e.g., polynucleotides encoding heavy or light chain variable regions or segments comprising the complementarity determining regions as described herein. In some embodiments, the polynucleotide encoding the heavy chain has at least 85%, 89%, 90%, 91%, 92%, 93%, 94%, 95%, 96%, 97%, 98%, 99% or 100% nucleic acid sequence identity with a polynucleotide selected from the group consisting of SEQ ID NO:42, SEQ ID NO:43 and SEQ ID NO:54. In some embodiments, the polynucleotide encoding the light chain has at least 85%, 89%, 90%, 91%, 92%, 93%, 94%, 95%, 96%, 97%, 98%, 99% or 100% nucleic acid sequence identity with a polynucleotide selected from the group consisting of SEQ ID NO:44, SEQ ID NO:45 and SEQ ID NO:55.

In some embodiments, the polynucleotide encoding the heavy chain has at least 85%, 89%, 90%, 91%, 92%, 93%, 94%, 95%, 96%, 97%, 98%, 99% or 100% nucleic acid sequence identity with a polynucleotide of SEQ ID NO:42. In some embodiments, the polynucleotide encoding the light chain has at least 85%, 89%, 90%, 91%, 92%, 93%, 94%, 95%, 96%, 97%, 98%, 99% or 100% nucleic acid sequence identity with a polynucleotide of SEQ ID NO:45 (i.e., LGT-209).

In some embodiments, the polynucleotide encoding the heavy chain has at least 85%, 89%, 90%, 91%, 92%, 93%, 94%, 95%, 96%, 97%, 98%, 99% or 100% nucleic acid sequence identity with a polynucleotide selected from the group consisting of SEQ ID NO:42. In some embodiments, the polynucleotide encoding the light chain has at least 85%, 89%, 90%, 91%, 92%, 93%, 94%, 95%, 96%, 97%, 98%, 99% or 100% nucleic acid sequence identity with a polynucleotide selected from the group consisting of SEQ ID NO:44 (i.e., LGT-210).

In some embodiments, the polynucleotide encoding the heavy chain has at least 85%, 89%, 90%, 91%, 92%, 93%, 94%, 95%, 96%, 97%, 98%, 99% or 100% nucleic acid sequence identity with a polynucleotide selected from the group consisting of SEQ ID NO:43. In some embodiments, the polynucleotide encoding the light chain has at least 85%, 89%, 90%, 91%, 92%, 93%, 94%, 95%, 96%, 97%, 98%, 99% or 100% nucleic acid sequence identity with a polynucleotide selected from the group consisting of SEQ ID NO:45 (i.e., LGT-211).

In some embodiments, the polynucleotide encoding the heavy chain has at least 85%, 89%, 90%, 91%, 92%, 93%, 94%, 95%, 96%, 97%, 98%, 99% or 100% nucleic acid sequence identity with a polynucleotide of SEQ ID NO:54. In some embodiments, the polynucleotide encoding the light chain has at least 85%, 89%, 90%, 91%, 92%, 93%, 94%, 95%, 96%, 97%, 98%, 99% or 100% nucleic acid sequence identity with a polynucleotide of SEQ ID NO:55 (i.e., mouse LFU720).

3. Assays for Identifying Anti-PCSK9 Antibodies

Antagonist antibodies can be identified by generating anti-PCSK9 antibodies and then testing each antibody for the ability to reduce or inhibit PCSK9 mediated events, e.g., binding to the LDLR, promoting the degradation of the LDLR. The assays can be carried out in vitro or in vivo. Preferred antibodies bind to PCSK9, do not prevent PCSK9 from binding to LDLR, and reduce or inhibit PCSK9-mediated degradation of LDLR.

The binding of the antibodies or antigen binding molecules to PCSK9 can be determined using any method known in the art, including without limitation, ELISA, Biacore and Western Blot.

PCSK9-mediated degradation of LDLR also can be measured using any method known in the art. In one embodiment, the ability of the anti-PCSK9 antibody or antigen binding molecule to inhibit LDLR degradation is determined using an infusion mouse model. Anti-PCSK9 antibodies or antigen binding molecules are infused intravenously (e.g., 3 μg/hour) into a mouse and the levels of LDLR in liver membrane preparations is determined in comparison to the levels of LDLR in liver membrane preparations from a mouse that has received intravenous infusions of a control antibody (e.g., that binds to an unrelated antigen). Mice that have received antagonist anti-PCSK9 antibodies will have detectably higher levels of LDLR, e.g., at least 10%, 20%, 50%, 80%, 100% higher, in comparison to mice that have received the control antibody.

Anti-PCSK9 antagonist antibodies also can be tested for their therapeutic efficacy in reducing plasma levels of LCL-C, non-HDL-C and/or total cholesterol. Anti-PCSK9 antibodies or antigen binding molecules are infused intravenously (e.g., 3 μg/hour) into a mammal (e.g., mouse, rat, non-human primate, human) and the plasma levels of LCL-C, non-HDL-C and/or total cholesterol is determined in comparison to the plasma levels of LCL-C, non-HDL-C and/or total cholesterol from the same mammal before treatment or from a mammal that has received intravenous infusions of a control antibody (e.g., that binds to an unrelated antigen). The mammal that has received antagonist anti-PCSK9 antibodies will have detectably lower plasma levels of LCL-C, non-HDL-C and/or total cholesterol, e.g., at least 10%, 20%, 50%, 80%, 100% lower, in comparison to the mammal before treatment or the mammal that has received the control antibody.

4. Compositions Comprising Anti-PCSK9 Antibodies

The invention provides pharmaceutical compositions comprising the present anti-PCSK9 antibodies or antigen-binding molecules formulated together with a pharmaceutically acceptable carrier. The compositions can additionally contain other therapeutic agents that are suitable for treating or preventing a given disorder. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, intranasal, inhalational, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The antibodies, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present invention. Applicable methods for formulating the antibodies and determining appropriate dosing and scheduling can be found, for example, in *Remington: The Science and Practice of Pharmacy*, 21$^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of the anti-PCSK9 antibody is employed in the pharmaceutical compositions of the invention. The anti-PCSK9 antibodies are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

In some embodiments, the pharmacological compositions comprise a mixture of the anti-PCSK9 antibody or antigen binding molecule and a second pharmacological agent. For example, the compositions may comprise a anti-PCSK9 antibody or antigen-binding molecule of the invention and an agent known to be beneficial for reducing cholesterol, including LDL-C, non-HDL-C and total cholesterol and/or raising HDL-C.

Exemplary second agents for inclusion in mixtures with the present anti-PCSK9 antagonist antibody or antigen binding molecule include without limitation an HMG-CoA reductase inhibitor (i.e., a statin), fibrates (e.g., clofibrate, gemfibrozil, fenofibrate, ciprofibrate, bezafibrate), niacin and analogs thereof, cholesterol absorption inhibitors, bile acid sequestrants (e.g., cholestyramine, colestipol, colesvelam), an ileal bile acid transport (IBAT) inhibitor, a thyroid hormone mimetic (e.g., compound KB2115), a microsomal triglyceride transfer protein (MTP) inhibitor, a dual peroxisome proliferator-activated receptor (PPAR) alpha and gamma agonist, an acyl CoA:diacylglycerol acyltransferase (DGAT) inhibitor, an acyl CoA:cholesterol acyltransferase (ACAT) inhibitor, a Niemann Pick C1-like 1 (NPC1-L1) inhibitor (e.g., ezetimibe), an agonist of ATP Binding Cassette (ABC) proteins G5 or G8, a cholesterol ester transfer protein (CETP) inhibitor, an inhibitory nucleic acid targeting PCSK9 and an inhibitory nucleic acid targeting apoB100. Lipid-lowering agents are known in the art, and described, e.g., in *Goodman and Gilman's The Pharmacological Basis of Therapeutics*, 11th Ed., Brunton, Lazo and Parker, Eds., McGraw-Hill (2006); 2009 *Physicians' Desk Reference (PDR)*, for example, in the 63rd (2008) Eds., Thomson PDR.

Additional lipid lowering agents of use in the present compositions are described and/or reviewed in, e.g., Chang, et al., *Curr Opin Drug Disco Devel* (2002) 5(4):562-70; Sudhop, et al., *Drugs* (2002) 62(16):2333-47; Bays and Stein, *Expert Opin Pharmacother* (2003) 4(11):1901-38; Kastelein, *Int J Clin Pract Suppl* (2003) March (134):45-50; Tomoda and Omura, *Pharmacol Ther* (2007) 115(3):375-89; Tenenbaum, et al., *Adv Cardiol* (2008) 45:127-53; Tomkin, *Diabetes Care* (2008) 31(2):S241-S248; Lee, et al., *J Microbiol Biotechnol* (2008) 18(11):1785-8; Oh, et al., *Arch Pharm Res* (2009) 32(1): 43-7; Birch, et al, *J Med Chem* (2009) 52(6):1558-68; and Baxter and Webb, *Nature Reviews Drug Discovery* (2009) 8:308-320.

In some embodiments, the anti-PCSK9 antibodies or antigen binding molecules of the invention are provided as a mixture with a statin. Exemplary statins include without limitation, atorvastatin, cerivastatin, fluvastatin, lovastatin, mevastatin, pitavastatin, pravastatin, rosuvastatin, and simvastatin.

In some embodiments, the anti-PCSK9 antibodies or antigen binding molecules of the invention are provided as a mixture with a pharmacological agent that induces hypercholesterolemia or triglyceridemia. For example, the second pharmacological agent may be a protease inhibitor, for example, Saquinavir, Ritonavir, Indinavir, Nelfinavir, Amprenavir, Lopinavir, Atazanavir, Fosamprenavir, Tipranavir, Darunavir, abacavir-lamivudine-zidovudine (Trizivir). In some embodiments, the second pharmacological agent is Tacrolimus.

5. Methods of Using Anti-PCSK9 Antibodies a. Conditions Subject to Treatment with Anti-PCSK9 Antibodies The anti-PCSK9 antagonist antibodies and antigen binding molecules of the invention find use in treating any disease condition mediated by the activity or over-activity of PCSK9.

For example, individuals who have or who are at risk of developing dyslipidemia or hypercholesterolemia for any number of reasons or etiologies may benefit from administration of the present anti-PCSK9 antagonist antibodies and antigen binding molecules. For example, the individual may have familial or genetically transmitted homozygous or heterozygous hypercholesterolemia in which a functional LDL-R is present. Genetic mutations associated with and/or causative of familial or genetically inherited hypercholesterolemia are summarized, e.g., in Burnett and Hooper, *Clin Biochem Rev* (2008) 29(1):11-26. The individual may also have other disease conditions or engage in behaviors that contribute to or increase the risk of developing dyslipidemia or hypercholesterolemia. For example, the individual may be obese, or suffer from diabetes or metabolic syndrome. The individual may be a smoker, lead a sedentary lifestyle, or have a diet high in cholesterol.

Targeting PCSK9 is useful for the reduction, reversal, inhibition or prevention of dyslipidemia, hypercholesterolemia and postprandial triglyceridemia. See, e.g., Le May, et al., *Arterioscler Thromb Vasc Biol* (2009) 29(5):684-90; Seidah, *Expert Opin Ther Targets* (2009) 13(1):19-28; and Poirier, et al., *J Biol Chem* (2009) PMID 19635789. Accordingly, administration of the present anti-PCSK9 antagonist antibodies and antigen binding molecules finds use in reducing, reversing, inhibiting and preventing, dyslipidemia, hypercholesterolemia and postprandial triglyceridemia in an individual in need thereof.

The present anti-PCSK9 antagonist antibodies and antigen binding molecules find use in reducing or lowering low density lipoprotein cholesterol (LDL-C) in an individual in need thereof. The individual may have persistently elevated levels of LDL-C. In some embodiments, the individual has LDL-C plasma levels consistently above 80 mg/dL, for example above 90, 100, 110, 120, 130, 140, 150, 160, 170, 180, 190 mg/dL, or higher. The present anti-PCSK9 antagonist antibodies and antigen binding molecules also find use in reducing or lowering non-high density lipoprotein cholesterol (non-HDL-C) or total cholesterol in an individual in need thereof.

The individual may already be taking another pharmacological agent to lower cholesterol, and be resistant or intolerant to this agent. For example, the individual may already be under a therapeutic regimen of a statin, which may have proven inefficacious in this individual in lowering LDL-C, non-HDL-C or total cholesterol to acceptable levels. The individual may also be intolerant to the administration of a statin. Combined administration of the present anti-PCSK9 antagonist antibodies and antigen binding molecules with a second agent useful in lowering LDL-C or non-HDL-C and/or raising HDL-C will improve the efficaciousness and tolerance of the second agent, for example, by allowing lower doses of the second agent to be administered.

In some embodiments, the individual has a gain-of-function mutation in the PCSK9 gene, for example, that results in an aberrant increase in the degradation of the LDLR.

In some embodiments, the individual is receiving a pharmacological agent the induces dyslipidemia or hypercholesterolemia, i.e., the individual has drug-induced dyslipidemia or hypercholesterolemia. For example, the individual may be receiving a therapeutic regime of protease inhibitors, e.g., for the treatment of an HIV infection. Another pharmacological agent known to cause elevated levels of plasma triglycerides is Tacrolimus, an immunosuppressive drug administered to transplantation patients. Cyclosporin has been shown to increase LDL significantly. See, e.g., Ballantyne, et al. (1996) 78(5):532-5. Second-generation antipsychotics (e.g., aripiprazole, clozapine, olanzapine, quetiapine, risperidone, and ziprasidone) have also been associated with dyslipidemia. See, e.g., Henderson, *J Clin Psychiatry* (2008) 69(2):e04 and Brooks, et al., *Curr Psychiatry Rep* (2009) 11(1):33-40.

b. Administration of Anti-PCSK9 Antibodies

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. Dosing can be daily, weekly, bi-weekly, monthly, or more or less often, as needed or desired. An exemplary treatment regime entails administration once weekly, once per every two weeks or once a month or once every 3 to 6 months.

In some embodiments, an polynucleotide encoding an anti-PCSK9 antibody or antigen binding molecule of the invention is administered. In embodiments where the agent is a nucleic acid, typical dosages can range from about 0.1 mg/kg body weight up to and including about 100 mg/kg body weight, e.g., between about 1 mg/kg body weight to about 50 mg/kg body weight. In some embodiments, about 1, 2, 3, 4, 5, 10, 15, 20, 30, 40 or 50 mg/kg body weight.

The antibody can be administered in single or divided doses. Antibody is usually administered on multiple occasions. Intervals between single dosages can be weekly, bi-weekly, monthly or yearly, as needed or desired. Intervals can also be irregular as indicated by measuring blood levels of anti-PCSK9 antibody in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime. In some embodiments, the anti-PCSK9 antibody or antigen binding agent is administered when plasma LDL-C levels in the patient rise above a predetermined threshold level, for example, at least about 80 mg/dL, for example, at least about 90, 100, 110, 120, 130, 140, 150, 160, 170, 180, 190 mg/dL, or higher.

c. Co-Administration with a Second Agent

The PCSK9 antibody antagonist can be used in combination with agents known to be beneficial for reducing cholesterol, including LDL-C, non-HDL-C and total cholesterol and/or raising HDL-C.

Active agents can be administered together in a mixture with the anti-PCSK9 antagonist antibody or each agent can be administered separately. The antibody agent and the other active agent can, but need not, be administered concurrently.

Exemplary second agents for use in co-administration with the present anti-PCSK9 antagonist antibody or antigen binding molecule include without limitation an HMG-CoA reductase inhibitor (i.e., a statin), fibrates (e.g., clofibrate, gemfibrozil, fenofibrate, ciprofibrate, bezafibrate), niacin and analogs thereof, cholesterol absorption inhibitors, bile acid sequestrants (e.g., cholestyramine, colestipol, colesvelam), an ileal bile acid transport (IBAT) inhibitor, a thyroid hormone mimetic (e.g., compound KB2115), a microsomal triglyceride transfer protein (MTP) inhibitor, a dual peroxisome proliferator-activated receptor (PPAR) alpha and gamma agonist, an acyl CoA:diacylglycerol acyltransferase (DGAT) inhibitor, an acyl CoA:cholesterol acyltransferase (ACAT) inhibitor, a Niemann Pick C1-like 1 (NPC1-L1) inhibitor (e.g., ezetimibe), an agonist of ATP Binding Cassette (ABC) proteins G5 or G8, a cholesterol ester transfer protein (CETP) inhibitor, an inhibitory nucleic acid targeting PCSK9 and an inhibitory nucleic acid targeting apoB100.

Additional lipid lowering agents of use are described and/or reviewed in, e.g., Chang, et al., *Curr Opin Drug Disco Devel* (2002) 5(4):562-70; Sudhop, et al., *Drugs* (2002) 62(16):2333-47; Bays and Stein, *Expert Opin Pharmacother* (2003) 4(11):1901-38; Kastelein, *Int J Clin Pract Suppl* (2003) March (134):45-50; Tomoda and Omura, *Pharmacol Ther* (2007) 115(3):375-89; Tenenbaum, et al., *Adv Cardiol* (2008) 45:127-53; Tomkin, *Diabetes Care* (2008) 31(2): 5241-5248; Lee, et al., *J Microbiol Biotechnol* (2008) 18(11): 1785-8; Oh, et al., *Arch Pharm Res* (2009) 32(1): 43-7; Birch, et al, *J Med Chem* (2009) 52(6):1558-68; and Baxter and Webb, *Nature Reviews Drug Discovery* (2009) 8:308-320.

In some embodiments, the anti-PCSK9 antibodies or antigen binding molecules of the invention are co-administered with a statin. Exemplary statins include without limitation, atorvastatin, cerivastatin, fluvastatin, lovastatin, mevastatin, pitavastatin, pravastatin, rosuvastatin, and simvastatin.

In some embodiments, the anti-PCSK9 antibodies or antigen binding molecules of the invention are co-administered with a pharmacological agent that induces hypercholesterolemia or triglyceridemia. For example, the second pharmacological agent may be a protease inhibitor, for example, Saquinavir, Ritonavir, Indinavir, Nelfinavir, Amprenavir, Lopinavir, Atazanavir, Fosamprenavir, Tipranavir, Darunavir, abacavir-lamivudine-zidovudine (Trizivir). In some embodiments, the second pharmacological agent is Tacrolimus.

In some embodiments, the anti-PCSK9 antibodies or antigen binding molecules of the invention are co-administered with an inhibitory nucleic acid (e.g., an siRNA, an miRNA, an antisense sequence, a ribozyme) that specifically targets PCSK9 or apoB100.

6. Kits

The pharmaceutical compositions of the present invention can be provided in a kit. In certain embodiments, a kit of the present invention comprises an anti-PCSK9 antagonist antibody or antigen binding molecule of the invention, as described herein. The anti-PCSK9 antibodies or antigen binding molecules can be provided in uniform or varying dosages.

In some embodiments, the kits comprise one or more second pharmacological agents, as described herein. The second pharmacological agent can be provided in the same formulation or in separate formulations from the anti-PCSK9 antibodies or antigen binding molecules. The dosages of the first and second agents can be independently uniform or varying.

In some embodiments, the kits comprise the PCSK9 antibody antagonist an one or more agents known to be beneficial for reducing cholesterol, including LDL-C, non-HDL-C and total cholesterol and/or raising HDL-C.

Exemplary second agents for inclusion in the kits with the present anti-PCSK9 antagonist antibody or antigen binding molecule include without limitation an HMG-CoA reductase inhibitor (i.e., a statin), fibrates (e.g., clofibrate, gemfibrozil, fenofibrate, ciprofibrate, bezafibrate), niacin and analogs thereof, cholesterol absorption inhibitors, bile acid sequestrants (e.g., cholestyramine, colestipol, colesvelam), an ileal bile acid transport (IBAT) inhibitor, a thyroid hormone mimetic (e.g., compound KB2115), a microsomal triglyceride transfer protein (MTP) inhibitor, a dual peroxisome proliferator-activated receptor (PPAR) alpha and gamma agonist, an acyl CoA:diacylglycerol acyltransferase (DGAT) inhibitor, an acyl CoA:cholesterol acyltransferase (ACAT) inhibitor, a Niemann Pick C1-like 1 (NPC1-L1) inhibitor (e.g., ezetimibe), an agonist of ATP Binding Cassette (ABC) proteins G5 or G8, a cholesterol ester transfer protein (CETP) inhibitor, an inhibitory nucleic acid targeting PCSK9 and an inhibitory nucleic acid targeting apoB100.

Additional lipid lowering agents of use in the kits are described and/or reviewed in, e.g., Chang, et al., *Curr Opin Drug Disco Devel* (2002) 5(4):562-70; Sudhop, et al., *Drugs* (2002) 62(16):2333-47; Bays and Stein, *Expert Opin Pharmacother* (2003) 4(11):1901-38; Kastelein, *Int J Clin Pract Suppl* (2003) March (134):45-50; Tomoda and Omura, *Pharmacol Ther* (2007) 115(3):375-89; Tenenbaum, et al., *Adv Cardiol* (2008) 45:127-53; Tomkin, *Diabetes Care* (2008) 31(2):5241-5248; Lee, et al., *J Microbiol Biotechnol* (2008) 18(11):1785-8; Oh, et al., Arch Pharm Res (2009) 32(1): 43-7; Birch, et al, *J Med Chem* (2009) 52(6):1558-68; and Baxter and Webb, *Nature Reviews Drug Discovery* (2009) 8:308-320.

In some embodiments, the anti-PCSK9 antibodies or antigen binding molecules of the invention provided in kits with a statin. Exemplary statins include without limitation, atorvastatin, cerivastatin, fluvastatin, lovastatin, mevastatin, pitavastatin, pravastatin, rosuvastatin, and simvastatin.

In some embodiments, the anti-PCSK9 antibodies or antigen binding molecules of the invention are provided in kits with a pharmacological agent that induces hypercholesterolemia or triglyceridemia. For example, the second pharmacological agent may be a protease inhibitor, for example, Saquinavir, Ritonavir, Indinavir, Nelfinavir, Amprenavir, Lopinavir, Atazanavir, Fosamprenavir, Tipranavir, Darunavir, abacavir-lamivudine-zidovudine (Trizivir). In some embodiments, the second pharmacological agent is Tacrolimus.

EXAMPLES

The following examples are offered to illustrate, but not to limit the claimed invention.

Example 1

Generation and Identification of the Pcsk9 Antagonist NVPLFU720

Summary

Studies were performed to generate a functional antibody antagonist against Pcsk9. Multiple hybridomas were identified that secreted an antibody capable of binding to a His-tagged version of the protein. Antibodies from hybridomas were evaluated for functional antagonist activity as measured by their ability to inhibit Pcsk9-mediated degradation of the LDL receptor on HepG2 cells resulting in an increased ability of these cells to take up LDL cholesterol. A potent functional murine anti-human Pcsk9 IgG1-kappa monoclonal antibody was identified and designated as NVP-LFU720 (LFU720).

Methods

Antigen and Other Proteins

A stable expression cell line secreting human Pcsk9 protein was generated by transfection of HEK293 Freestyle™ cells (Invitrogen, Carlsbad, Calif.). Briefly, the cells cultivated in Freestyle™ medium (Invitrogen) plus 10% fetal calf serum in adherent mode on BioCoat flasks (Becton Dickinson) were transfected using Lipofectamine 2000™ transfection reagent and a recombinant plasmid featuring the mellittin signal sequence, the mature Pcsk9 cDNA (aa 31-692) and a his6 (SEQ ID NO:57) tag at the C-terminus of the sequence (cloned by E. Hampton, GNF, NPL 010051). 48 hours post transfection selection of positive transfectants was started by adding 100 μg/mL Zeocin into the cultivation medium. Four weeks later four stable cell pools of Pcsk9-producing cells had emerged. Pool 4, being the highest producer, was adapted to serum-free suspension conditions in Freestyle™ medium and was subsequently scaled up for large scale production using the Wave™ bioreactor at a scale of 10-20 L production volume.

Several runs were performed over time yielding recombinant protein produced at rates between 12 and 30 mg/L. The cell supernatants were harvested and concentrated by cross-flow filtration. The resulting concentrate was applied to a 25 mL NiNTA His-Bind Superflow column (equilibrated with 50 mM Tris/300 mM NaCl/1 mM $CaCl_2$/2 mM β-Mercaptoethanol, pH 7.4) at 0.5 mL/min. After baseline washing with 50 mM Tris/300 mM NaCl/20 mM Imidazole, pH 7.4, bound material was eluted with 50 mM Tris/300 mM NaCl/250 mM Imidazole, pH 7.4. The resulting eluate was dialyzed against PBS, pH 7.3, sterile filtered and aliquotted. A sample was analyzed by analytical size-exclusion chromatography for determination of oligomerization. The HPLC chromatogram obtained of the purified protein shows two peaks, the major one accounting for 85%. HPLC-ESI MS analysis of full length protein reveals a mass of 58176.0 Da which is according the expected mass from mellitin-hsPcsk9 aa31-692-His with all Cysteine residues oxidized. Part of sample is additionally N-glycosylated. The contaminating protein of approx 13 kD mass resembles, most likely, the free pro-domain of the protein. The corresponding homologues of Pcsk9 from mouse and cynomolgus monkey were produced in large-scale transient expression approaches using again HEK293 Freestyle cells cultivated in serum-free suspension in Freestyle medium. The recombinant plasmids, mouse Pcsk9 cDNA featuring a natural leader sequence and a his6 (SEQ ID NO:57) tag at the C-terminus and cyno Pcsk9 featuring a CD33 leader sequence and a C-terminal his6 (SEQ ID NO:57) tag were transfected into Freestyle cells using Polyethylenimine as carrier of plasmid DNA at a ratio of 1:3 (μg/mL:μg/mL DNA:PEI). Production runs were carried out at the 10 liter scale in Wave™ bioreactors; protein purification and characterization was done analogously to the protocols described above for the human Pcsk9 protein. Yields for mouse Pcsk9 protein ranged between 0.7 and 2.7 mg/L culture, cyno Pcsk9 was obtained at 3.1 mg/L.

Hybridoma Generation
Immunization of Mice and Production of Hybridomas

Purified Pcsk9 was diluted 1:1 with Freunds Complete Adjuvant prior to immunization of Bcl-2 transgenic mice (C57BL/6-Tgn (bcl-2) 22 wehi strain). Mice were immunized using a procedure that calls for Repetitive Immunization at Multiple Sites (RIMMS). Briefly, mice were injected with 1-3 μg of antigen at 8 specific sites proximal to peripheral lymph nodes (PLN). This procedure was repeated 6 times over a 12-day period. On Day 12, a test bleed was collected and the serum antibody titer was analyzed by ELISA. Pooled PLN were removed from high titer mice on Day 15. To harvest lymphocytes, PLN were washed twice with plain DMEM and then dissociated by passage through a 0.22 micron screen (Falcon #352350). The resulting lymphocytes were washed 2 additional times prior to fusion. NSO/Bcl-2 myeloma cells were mixed with lymphocytes at a ration of 2.5 lymphocytes to 1 NSO cell. The cell mixture was centrifuged and 1 mL of PEG 1500 was subsequently added drop wise to the cell pellet for 1 min. After 30 seconds, 1 mL of DMEM was slowly added, and 1 min later, 19 mL of DMEM was added for 5 min. Fused cells were pelleted, resuspended at a density of $2 \times 10^5$ cells/mL in HAT media (DMEM+20% FBS, Pen/Strep/Glu, 1×NEAA, 1×HAT, 0.5×HFCS), and placed at 37° C. for one h. The cells were then plated in 384-well plates at 60 μL/well.

Screening of Hybridomas Secreting Functional Antibodies to Pcsk9

Ten days after fusion, hybridoma plates were screened for the presence of Pcsk9 specific antibodies. For the ELISA screen, Maxisorp 384-well plates (Nunc #464718) were coated with 50 μL of Pcsk9 (diluted to 15 ng/well in PBS) and incubated overnight at 4° C. The remaining protein was aspirated and wells were blocked with 1% BSA in PBS. After 30 min incubation at room temperature, the wells were washed four times with PBS+0.05% Tween (PBST). 15 μL of hybridoma supernatant was transferred to the ELISA plates. 15 μL of mouse serum, taken at the time of PLN removal, was diluted 1:1000 in PBS and added as a positive control. 50 μL of secondary antibody (goat anti mouse IgG-HRP (Jackson Immuno Research #115-035-071), diluted 1:5000 in PBS) was added to all wells on the ELISA plates. After incubation at room temperature for 1 h, the plates were washed eight times with PBST. 25 μL of TMB (KPL #50-76-05) was added and after 30 min incubation at room temperature; the plates were read at an absorbance of 605 nm. Cells from positive wells were expanded into 24-well plates in HT media (DMEM+20% FBS, Pen/Strep/Glu, 1×NEAA, 1×HT, 0.5× HFCS).

Antibody Purification

Supernatant containing LFU720 was purified using protein G (Upstate #16-266 (Billerica, Mass.)). Prior to loading the supernatant, the resin was equilibrated with 10 column volumes of PBS. Following binding of the sample, the column was washed with 10 column volumes of PBS, and the antibody was then eluted with 5 column volumes of 0.1 M Glycine, pH 2.0. Column fractions were immediately neutralized with ⅒th volume of Tris HCl, pH 9.0. The OD280 of the fractions was measured, and positive fractions were pooled and dialyzed overnight against PBS, pH 7.2.

Binding Kinetics and Biacore Assay

Determination of kinetic binding parameters was done by surface plasmon resonance measurements using the optical biosensor Biacore S51. This technology allows the label-free determination of the microscopic rate constants for binding ($k_a$) and dissociation ($k_d$) of a ligand to a receptor. It is, therefore, especially suited for characterizing the antibody-antigen interactions.

Binding studies of Pcsk9 to the LFU720 (2 μg/mL) were carried out by capturing the mouse antibody with a rabbit anti-mouse Fcγ antibody (Biacore #BR-1005-14) that was previously immobilized onto a Series S CM-5 Biacore sensor chip (certified) (Biacore #BR-1005-30). Covalent binding of the Fcγ capture antibody was done with the 'Amine Coupling Kit' (Biacore #BR-1000-50). The capture antibody (rabbit-anti-mouse) was attached to the EDCactivated dextran surface with a 50 μg/mL anti-Fcγ antibody solution in 10 mM sodium acetate, pH 5 (Biacore #BR-1003-51) at a flow rate of 10 μL/min. A range of concentrations of Pcsk9 from 0.5 μM to 7.8 nM (2 fold serial dilution) were flowed over the captured LFU720 chip in PBS plus 100 mM NaCl, 0.005% P20 (Biacore #BR-1000-54). The resulting sensorgrams were analyzed using the Biacore S51 Evaluation Software. Data from all concentrations was fitted globally to a 1:1 Langmuir model.

TR-FRET Assay

The TR-FRET assay was performed in 384-well white, shallow plates (Perkin Elmer, 6008280). hPcsk9-AF (10.7 nM) was incubated with serial dilutions of unlabeled hPcsk9 protein, EGF-A peptide, or NVP-LFU720-AX-1 antibody for 30 minutes at room temperature in 15 μL of assay buffer (20 mM HEPES, pH 7.2, 150 mM NaCl, 1 mM $CaCl_2$, 0.1% v/v Tween 20, and 0.1% w/v BSA). This was followed by addition of 5 μL of hLDL-R-Eu (4 nM) in assay buffer to the hPcsk9 and NVP-LFU720-AX-1 preincubated complex, and incubation at room temperature for 90 minutes. The final concentrations of these labeled proteins were 8 nM of hPcsk9-AF and 1 nM of hLDL-R-Eu. The TR-FRET signal was measured with EnVision 2100 multilabel reader (Perkin Elmer) at 330 nm excitation and 665 nm emission. Data was converted to normalized values using the following formula: [(665 nm value×10,000)/(615 nm value)]. The percentage inhibition was calculated with the following formula: 100-[(normalized value of treated sample/averaged normalized value of untreated samples)×100]. The percentage inhibition dose response curves were plotted using Prism version 5 with the formula, Y=Bottom+(Top−Bottom)/(1+10^((LogIC$_{50}$−X)*HillSlope)) (GraphPad Prism Software).

LDL-RTurnover Assay

HepG2 cells were trypsinized and seeded at 6×10$^4$ cells per well in 100 μL of culture medium in flat bottomed 96-well plates (Corning, 3595) which were pre-coated with 1% v/v collagen), then incubated at 37° C. in 5% CO$_2$ for 24 hours. Generally, cells were treated with 100 μL of serum-free medium containing either hPcsk9 protein, EGF-A peptide and/or NVP-LFU720-AX-1 antibody. After treatment, the medium was discarded, and the cells were washed with 100 μL of PBS. To harvest the cells, 100 μL of Versine (Biowhittaker, 17-771E) was added and incubated for one hour at 37° C. in 5% CO$_2$, followed by addition of 100 μL of FACS buffer. The cells were transferred to V-bottom 96-well plates (Corning, 3894) and centrifuged at 1200 rpm for 5 minutes to pellet the cells. To block non-specific binding sites on the cells, 50 μL of 100 μg/mL normal rabbit IgG (MP biomedicals, 55944) and mouse IgG (Sigma, I5381) in FACS buffer were added to each well and incubated for 30 minutes in ice. Cells were centrifuged at 1200 rpm for 5 min, and the buffer was removed by flicking the plate. To label the cells, 10 μL of rabbit anti-hLDL-R-Alexa 647 IgG (5 μg/mL) and 10 μL of mouse anti-transferrin-R-phycoerythrin (PE) IgG (2 μg/mL) (CD71, Becton Dickinson Biosciences, 624048) labeled antibodies in FACS buffer were added to each well and incubated for 60 minutes in ice. Cells were centrifuged at 1200 rpm for 5 min, and the buffer was removed by flicking the plate. Unbound antibodies were removed by washing the cells twice with 200 μL per well of FACS buffer. Cells were fixed in 1% paraformaldehyde in PBS, and viable cells were gated (5000) and analyzed using a BD LSR II flow cytometer and FACS-DIVA software (Becton Dickinson). The median value of PE fluorescence was measured at excitation of 488 nm and emission of 575 nm. The median value of Alexa 647 fluorescence was measured at excitation of 488 nm and emission of 633 nm. A custom made rabbit anti-hLDL-R polyclonal IgG 583 was custom produced by Covance (Denver, Pa., USA) for the FACS detection of surface hLDL-R on HepG2 cells. The rabbit anti-hLDL-R IgG 583 exhibited approximately a 7-fold window for detection of hLDL-R on the surface of HepG2 cells as compared to normal rabbit IgG. To determine the specificity of the anti-hLDL-R IgG 583 for LDL-R on the surface of HepG2 cells, an experiment was performed using hLDL-R protein as a competitor for binding of this IgG. A dose-dependent decrease in the average medium fluorescence for the anti-hLDL-R IgG 583 towards HepG2 cells was observed with increasing concentrations of hLDL-R protein. This demonstrated the anti-hLDL-R IgG 583 specifically recognizes the LDL-R on the surface of HepG2 cells as measured by FACS. Future work used directly labeled anti-hLDL-R-583-Alexa 647 IgG for the FACS quantification of LDL-R on the surface of HepG2 cells.

LDL-C Uptake

HepG2 cells were trypsinized and seeded at 6×10$^4$ cells per well in 100 μL of culture medium in flat bottomed 96-well plates (Corning, 3595, which were pre-coated with 1% v/v collagen), then incubated at 37° C. in 5% CO$_2$ for 24 hours. Unless otherwise stated, cells were treated with 100 μL of serum-free medium containing either hPcsk9 protein, EGF-A peptide and/or NVP-LFU720-AX-1 antibody. After treatment, each well received 20 μL of 30 μg/mL 3,3'-dioctadecylindocarbocyanine-labeled low-density lipoprotein (DiI-LDL) (Intracell, RP-077-175) in serum-free medium and incubated at 37° C. in 5% CO$_2$ for 2 hours. The medium was removed by flicking the plates, and the cells were washed with 100 μL of phosphate buffered saline (PBS without calcium or magnesium, Invitrogen, 14190-144). The PBS was removed by flicking the plates, and 100 μL of 0.25% trypsin-EDTA was added to each well and incubated for 5 minutes at 37° C. in 5% CO$_2$. One hundred μL of FACS buffer (PBS containing 5% FBS, 2 mM EDTA, and 0.2% sodium azide) was added to each well, and the cells were pelleted by centrifugation at 1200 rpm for 5 minutes. The medium was discarded by flicking the plate, and the cells were fixed by addition of 50 μL of 1% paraformaldehyde (Electron Microscopy Sciences, 15710) in PBS per well. Viable cells were gated and analyzed using a BD LSR II flow cytometer and FACSDIVA software (Becton Dickinson). The median value of DiI-LDL fluorescence was measured at excitation 488 nm and emission 575 nm, and 5000 cells were analyzed. Bar graphs were generated using Microsoft Excel 2002 (Microsoft Corporation). Percentage of activation was calculated as follows, %Activation=[1−(X÷A)]×100, where X=medium fluorescence reading from sample well and A=medium fluorescence reading from well with only hPcsk9 treatment.

Percentage of activation was plotted versus treatment to determine EC$_{50}$'s from dose response curves generated using the equation Y=Bottom+(Top−Bottom)/(1+10^((LogEC50−X)×HillSlope)) and GraphPad Prism 5 (GraphPad Software).

Results

Generation of an Anti-Human Pcsk9 Monoclonal Antibody

B-cells were harvested from the primary lymph nodes of animals immunized with Pcsk9 protein. Hybridoma were generated using standard PEG-mediated fusion. The resulting fusion was assayed by ELISA, and positive binders to human Pcsk9 were identified and expanded to generate supernatants. There were multiple ELISA positive clones identified that were subsequently triaged by functional assays. The clone that was identified as the lead candidate is LFU720. In addition to our lead candidate, LFU720, multiple other clones were identified that failed to block the interaction of Pcsk9 and LDLr (as measured by FRET) yet when bound to Pcsk9 were able to block Pcsk9's ability to mediate LDLr degradation (as measured by LDLc uptake), including clones 21D6, 5A4-C1, and 13F1. Clone 21D6 also showed the ability to block Pcsk9 degradation of the LDLr in vivo.

Screening of LFU720 for Binding Specifically to Pcsk9

LFU720 specificity was examined by evaluating binding in ELISA to a series of other proteins. The binding of LFU720 to three other HIS-tagged proteins was compared to binding to Pcsk9-HIS. This demonstrated that the binding to Pcsk9 is specific, and that the antibody was not binding to the HIS tag.

Evaluation of LFU720 for Binding to the Cynomolgus Pcsk9

The binding of LFU720 to the cynomolgus homolog of Pcsk9 was determined. For this assay, the supernatants from cells expressing the cynomolgus HIS-tagged Pcsk9 were utilized along with a Ni capture plate, avoiding the need to purify the material. Human Pcsk9 was dilute and also captured via its HIS-tag. LFU720 was able to bind to both human and cynomolgus Pcsk9. 5P20 also did not bind to human LDL-R or mouse Pcsk9 in ELISA.

Binding Kinetics of LFU720

The mouse antibody LFU720, that recognizes the human Pcsk9 protein, was analyzed for its binding affinity by using an optical biosensor technique (Biacore). LFU720 was found to bind with high affinity to recombinant human Pcsk9 with sub-nanomolar affinity (KD=200 μM).

Screening of LFU720 for Blocking the Pcsk9/LDL-R Interaction

TR-FRET assay was used for determining if the anti-hPcsk9 antibody NVP-LFU720 could disrupt the interaction between hPcsk9-AF and hLDL-R-Eu labeled proteins. Unlabeled hPcsk9 protein or EGF-A peptide were evaluated to demonstrate the assay could detect the disruption of the TR-FRET signal generated by interaction of hLDL-R-Eu and hPcsk9-AF labeled proteins. Increasing concentrations of unlabeled hPcsk9 competed with hPcsk9-AF for binding to hLDL-R-Eu, which resulted in a decrease of the TR-FRET signal. The EGF-A peptide disrupted the interaction between hLDL-R-Eu and hPcsk9-AF with an $IC_{50}$ of 2.5 µM. Conversely, NVP-LFU720 poorly disrupted the TR-FRET signal between hPcsk9-Eu and hLDL-R-AF with an $IC_{50}$ greater than 1000 nM, and exhibited a U-shaped response at low antibody concentrations.

Screening of LFU720 for Inhibiting Pcsk9-Mediated Degradation of the LDL-R

Pcsk9 binding to the LDL-R has been shown to lead to LDL-R degradation, and this was confirmed using HepG2 cells and recombinant human Pcsk9. The ability of LFU720 to bind Pcsk9 and block this effect was determined. NVP-LFU720 inhibited exogenous hPcsk9 treated HepG2 cells and led to increased cell-surface LDL-R.

Screening of LFU720 for Inhibiting Pcsk9 and Restoring LDLuptake

The inhibition of Pcsk9 degradation of the LDL-R should restore the ability of HepG2 cells to internalize LDL-C. NVP-LFU720 prevented Pcsk9-mediated LDL-R degradation on HepG2 cells treated with exogenous hPcsk9 and led to increased DiI-LDL-uptake with an $EC_{50}$ of 99 nM.

Example 2

Creation of PCSK9 Antagonist Antibodies NVP-LGT209, NVP-LGT210 and NVP-LGT211

Introduction

This example describes the generation of human antibodies NVP-LGT209, NVP-LGT210 and NVP LGT211 by engineering the murine monoclonal PCSK9 antagonist antibody NVP-LFU720 to have greater sequence homology to a human germline antibody. NVP-LGT209, NVP-LGT210 and NVP LGT211 retain the epitope specificity, affinity, and cynomolgus macaque PCSK9 cross-reactivity of the parent murine antibody, NVP-LFU720. NVP-LGT209, NVP-LGT210 and NVP LGT211 have much higher homology to the human germline sequence than the original murine antibody and should therefore be better tolerated by the human immune system.

Mouse monoclonal antibody LFU720 was Humaneered™ to bring its protein sequence closer to a human germline sequence and decrease its immunogenicity. Humaneering™ technology is available through KaloBios of South San Francisco (on the worldwide web at kalobios.com). Antibody Humaneering™ generates engineered human antibodies with V-region sequences that have high homology to a human germline sequence while still retaining the specificity and affinity of the parent or reference antibody (U.S. Patent Publ. 2005/0255552 and 2006/0134098). The process first identifies the minimum antigen binding specificity determinants (BSDs) in the heavy and light chain variable regions of a reference Fab (typically sequences within the heavy chain CDR3 and the light chain CDR3). As these heavy and light chain BSDs are maintained in all libraries constructed during the Humaneering™ process, each library is epitope-focused, and the final, fully Humaneered™ antibodies retain the epitope specificity of the original mouse antibody.

Next, full-chain libraries (in which an entire light or heavy chain variable region is replaced with a library of human sequences) and/or cassette libraries (in which a portion of the heavy or light chain variable region of the mouse Fab is replaced with a library of human sequences) are generated. A bacterial secretion system is used to express members of the library as antibody Fab fragments, and the library is screened for Fabs that bind antigen using a colony-lift binding assay (CLBA). Positive clones are further characterized to identify those with the highest affinity. Identified human cassettes supporting binding in the context of residual murine sequences are then combined in a final library screen to generate completely human V-regions.

The resulting Humaneered™ Fabs have V-segment sequences derived from human libraries, retain the short BSD sequences identified within the CDR3 regions, and have human germline Framework 4 regions. These Fabs are converted to full IgGs by cloning the variable regions of the heavy and light chains into IgG expression vectors. Fully Humaneered™ antibodies generated in this process retain the binding specificity of the parent, murine antibody, typically have equivalent or higher affinity for antigen than the parent antibody, and have V-regions with a high degree of sequence identity compared with human germline antibody genes at the protein level.

Methods

Cloning of Murine V-Regions

The V-region DNA from murine monoclonal NVP-LFU720 was amplified by RT-PCR from RNA isolated from the hybridoma cell line using standard methods. Primers successfully used for PCR amplification of the heavy chain variable region from hybridoma cDNA were $V_H14$ (5'-CTTCCT-GATGGCAGTGGTT-3'; SEQ ID NO:58) (Chardes T, et al 1999, *FEBS Letters;* 452(3):386-94) and HCconstant (5'-GCGTCTAGAAYCTCCACACACAGGRRC-CAGTGGATAGAC-3'; SEQ ID NO:59). Primers successfully used for PCR amplification of the light (kappa) chain variable region from hybridoma cDNA were Vκ4/5 (5'-TCAGCTTCYTGCTAATCAGTG-3'; SEQ ID NO:60) (Chardes T, et al., 1999, supra) and LCconstant (5'-GCGTCTAGAACTGGATGGTGGGAAGATGG-3'; SEQ ID NO:61). The amplified heavy and light chain variable regions were sequenced. PCR was then used to amplify the V-genes and to incorporate restriction enzyme sites for cloning into KaloBios vectors: Vh into KB1292-His (modified version of KB1292 that encodes a C-terminal flexible linker and 6-His (SEQ ID NO:57) tag of amino acid sequence AAGASHHHHHH (SEQ ID NO:62) on CH1) at NcoI (5') and NheI (3'); Vk into KB1296 at NcoI (5') and BsiWI (3'). These separate heavy and light chain vectors were then combined into a single dicistronic KaloBios Fab expression vector by restriction digest with BssHII and ClaI and ligation. Fab fragments were expressed in *E. coli* from this vector. This Fab was tested for PCSK9-antigen binding and is referred to as reference Fab SR032.

Fab Purification

Fab fragments were expressed by secretion from *E. coli* using KaloBios expression vectors. Cells were grown in 2×YT medium to an OD600 of ~0.6. Expression was induced by adding IPTG to 100 µM and shaking for 4 hours at 33° C. Assembled Fab was obtained from periplasmic fractions by osmotic lysis and purification by affinity chromatography using Ni-NTA columns (H isTrap HP columns; GE Healthcare catalog #17-5247-01) according to standard methods. Fabs were eluted in buffer containing 500 mM imidazole and thoroughly dialyzed against PBS pH 7.4 without calcium and magnesium.

Library Construction

For the first step in library construction, epitope-focused full human V-region libraries were generated by PCR amplification of KaloBios human V-segment library sequences. In making these full-chain libraries, the unique CDR3-FR4 regions containing the BSD and human germline J-segment sequences from the optimized reference Fab SR038 were attached to the human V-segment libraries using overlapping PCR. These full V-region libraries were not screened directly; rather, they were used as templates for construction of the Vh and Vk middle libraries. KaloBios human V-segment libraries used for full-chain library construction were chosen based on the human germline sequence closest to the original murine Vh and Vk's in the CDR regions. The original murine NVP-LFU720 Vh is closest to human germline sequence Vh1-02 in its CDRs, so a mixture of the two KaloBios libraries that contains Vh1 subgroup members (KB1410 and KB1411) was used in making the full Vh library. Likewise, as the NVP-LFU720 Vk is closest to the Vk3 L6 human germline sequence in its CDRs, a mixture of the two KaloBios human V-segment libraries containing Vk3 subgroup members (KB1423 and KB1424) was used in making the full Vk library. These full-length Vh and Vk libraries were then used as templates for the construction of cassette libraries in which only part of the parent murine V-segment is replaced by a library of human sequences. Two types of cassettes were constructed by bridge PCR: front-end cassettes containing human sequences in FR1, CDR1, and the first part of FR2 were amplified from the mixture of Vh1 libraries (KB1410 and KB1411) or the mixture of Vk3 libraries (KB1423 and KB1424) described above as a template. Middle cassettes containing human sequences in the last part of FR2, CDR2, and FR3 were amplified using the full human Vh- or Vk-region libraries described above as templates. Vh cassettes had overlapping common sequences in FR2 at amino acid positions 45-49 (Kabat numbering); Vk cassettes had overlapping common sequences in FR2 at amino acid residues 35-39 (Kabat numbering). In this way, front-end and middle human cassette libraries were constructed by PCR for human V-heavy 1 and V-kappa 3 isotypes. Each Vh cassette library was cloned into vector KB1292-His at NcoI (5') and KpnI (3'); each Vk cassette library was cloned into vector KB1296-B (modified version of KaloBios vector KB1296 which has a silent HindIII site added in FR4) at NcoI (5') and HindIII (3'). Resultant Vh or Vk plasmid libraries were then combined with the complementary chain from the optimized reference Fab SR038 (e.g., the Vh front-end library was combined with the optimized reference Vk vector) by digestion with BssHII and ClaI and subsequent ligation to create libraries of dicistronic vectors expressing full Fabs.

General ELISA

Recombinant human or cynomolgus macaque PCSK9-His6 antigen was used for all ELISA assays. Typically, PCSK9-His6 antigen diluted in PBS pH 7.4 was bound to a 96-well microtiter plate at 300 ng/well by overnight incubation at 4° C. The plate was blocked with a solution of 3% BSA in PBS for one hour at 37° C., and then rinsed once with PBST. Fab-containing induced cell medium or diluted, purified Fab (50 µL) was then added to each well. After a one-hour incubation at 37° C., the plate was rinsed three times with PBST. Anti-human-kappa chain HRP conjugate (Sigma #A7164) diluted 1:5000 in PBS (50 µL) was added to each well, and the plate was incubated for 45 min at room temperature. The plate was washed three times with PBST, then 100 µL of SureBlue TMB substrate (KPL #52-00-03) was added to each well and the plate was incubated for ~10 min at room temperature. The plate was read at 650 nm in a spectrophotometer.

For specificity ELISAs on purified human and mouse IgGs, a 384-well plate was coated with a panel of purified human or mouse antigens at 88 ng per well and incubated overnight at 4° C. The plate was blocked and washed as described above, then 22 µL of purified mouse or human anti-PCSK9 antibody diluted to 2 µg/mL in PBS was added to each well. The plate was incubated for 1 hr at 37° C. then washed with PBST. Anti-mouse Fc antibody (Jackson ImmunoResearch Labs #115-035-071) or anti-human kappa antibody (Sigma #A7164) conjugated to HRP was diluted 1:5000 in PBS (25 µL) and added to each well. The plate was incubated for 1 hr at room temperature, then washed and developed as described above.

Colony Lift Binding Assay (CLBA)

Screening of Humaneered™ libraries of Fab fragments was carried out essentially as described in (U.S. Patent Publ. 2005/0255552 and 2006/0134098) using nitrocellulose filters coated with PCSK9-His6 at 6 µg/mL. Fabs bound to the antigen-coated filter were detected using an alkaline phosphatase-conjugated anti-human kappa light chain antibody (Sigma #A3813) diluted 1:5000 in PBST, and blots were developed with DuoLux chemiluminescent substrate for alkaline phosphatase (Vector Laboratories #SK-6605).

Generation of Biotinylated Recombinant PCSK9 and Affinity Measurements

PCSK9 with C-terminal Avi- (for site-directed biotinylation) and His6 (SEQ ID NO:57) tags (PCSK9-Avi-His6) was generated by inserting an EcoRI restriction site between the gene encoding PCSK9 and the His6 (SEQ ID NO:57) tag in the pRS5a/PCSK9 plasmid; expresses amino acids 31-692 of PCSK9 Uniprot Accession Q8NBP7 with a C-terminal His6 (SEQ ID NO:57) tag). Oligonucleotides encoding the Avi tag (amino acid sequence: GGGLNDIFEAQKIEWHE; SEQ ID NO:63) and flanked with EcoRI overhangs were phosphorylated with T4 polynucleotide kinase (Invitrogen), annealed, and subsequently ligated into pRS5a/PCSK9 using the newly inserted EcoRI site. Clones containing the Avi tag were verified by sequence analysis. Expression of PCSK9-Avi-His6 was performed in the 293 Freestyle Expression System (Invitrogen), and secreted recombinant protein was purified using Ni-NTA resin (QIAGEN). Following purification, PCSK9-Avi-His6 protein was dialyzed against 10 mM Tris pH 8.0, 50 mM NaCl. The protein was biotinylated in vitro with biotin-protein ligase (Avidity) according to the manufacturer's protocol. Upon completion, the reaction was dialyzed against PBS pH 7.2, and biotinylation was verified by Western blot, probing with HRP-conjugated streptavidin.

The binding kinetics of IgGs and Fab fragments were analyzed using a Solution Equilibrium Titration ("SET") assay. Briefly, serial dilutions of hPCSK9 were added to 60 pM IgG or Fab and incubated overnight. A 96-well Standard Bind microtiter plate (Meso Scale Discovery) was coated with 1 µg/ml hPCSK9 and incubated overnight, washed with PBS/ 0.05% (w/v) Tween 20, blocked with PBS/5% (w/v) BSA, and washed again. The antibody-antigen preparation was added to the PCSK9-coated Standard Bind plate and incubated for 30 min at room temperature. After three additional washing steps, Sulfo-Tag-labeled goat-anti-human-detection antibody (R32AJ-5, Meso Scale Discovery) was added and incubated one hour at room temperature. After washing the plate three times, Read Buffer (Meso Scale Discovery) was added and electrochemiluminescence (ECL) signals were measured by a Sector Imager 6000 (Meso Scale Discovery). ECL data were processed with the excel add-in XLfit 4.3.2 (ID Business Solutions) using the fitting model applicable for antibodies described in Piehler, et al., (1997) *J Immunol Methods* 201:189-206. High affinity binding was observed between human PCSK9 and the antibodies LGT209, LGT210, and LGT211 in solution, with KD values of 150-190 pM calculated for each.

Antibody Production and Purification

Fully Humaneered™ NVP-LGT209, NVP-LGT210 and NVP-LGT211 antibodies (silent IgG1 kappa) were produced by co-transfection of vectors as follows into 293 Freestyle cells using 293fectin transfection reagent (Invitrogen #51-0031) according to the manufacturer's protocol.

LGT-209–pJG04(Vh)+pJG10(Vk)

LGT-210–pJG04(Vh)+pJG01(Vk)

LGT-211–pSR74(Vh)+pJG10(Vk)

Antibody was purified from 293 Freestyle cell supernatants using a 5-mL HiTrap Protein A HP column (GE Healthcare #17-0403-03). Antibody was eluted using IgG Elution Buffer (Pierce #21004), and buffer exchanged into PBS by dialysis. Protein A affinity chromatography was performed on an AKTAFPLC liquid chromatography system (GE Healthcare).

Epitope Competition Assay

Competition between the original mouse antibody NVP-LFU720 and its Humaneered™ derivative NVP-LGT209 for epitope binding on PCSK9 was assayed using the ForteBio Octet QK system and Streptavidin High Binding Biosensors coated with biotinylated PCSK9-Avi-His6. Three different antibodies were then bound to separate PCSK9-coated sensors to saturation: mouse LFU720, fully human LGT209, or the control mouse antibody 7D16 (known to have a separate epitope from that of LFU720). Next, all sensors were dipped into wells containing LFU720 mouse antibody to determine whether the first antibody could block LFU720 binding.

Results

Murine and Reference V-Region Amino Acid Sequences

RT-PCR products from hybridoma cells that express NVP-LFU720 were sequenced, and this sequence was largely (95% or greater) verified at the protein level using a ThermoElectron LTQ-Orbitrap Mass Spectrometer. The heavy and light chain variable regions of LFU720 were then cloned into KaloBios vectors in order to create the reference Fab SR032. The first amino acid in NVP-LFU720 Vk had to be changed from a glutamine (Q) to a glutamic acid (E) to enable cloning into KaloBios vectors for generation of the reference Fab SR032; therefore, the SR032 Vk has glutamic acid at the first Vk position. The Fab SR032 has intact murine V-regions from NVP-LFU720 fused with human constant regions and was purified from E. coli. In a dilution ELISA test of PCSK9-His6 antigen binding, the cloned SR032 reference Fab produced binding curves that were dependent on Fab concentration. In addition to the reference Fab (SR032), an optimized reference Fab, SR038, was constructed. Several framework amino acid residues in SR032 were changed to human germline in SR038.

Reference and Optimized Reference Fab Affinity Analysis

The human germline residues incorporated into the optimized reference Fab SR038 in FR1 and FR3 are those specified by the PCR primers used to amplify the human V-segment repertoire and thus are present in all members of the Humaneered™ V-region libraries. The optimized reference Fab is constructed to assess whether or not any of the changes to human germline alter the properties of Fab binding. By dilution ELISA using purified Fabs, the affinities of SR032 and SR038 for recombinant PCSK9 antigen were determined to be identical, indicating that the amino acid changes in SR038 are tolerated.

Library Construction and Selection of Fully Humaneered™ Fabs

Heavy and light chain front-end and middle cassette libraries subgroup-restricted to Vh1 or Vk3 were generated and screened by CLBA. For Vh, front-end cassettes which supported binding to PCSK9 antigen were identified by colony-lift binding assay, but Vh middle cassettes were not. For Vk, both front-end and middle cassettes were identified by colony lift, and in addition, some full Vk clones were identified (due to contamination of the Vk front-end library with full-chain Vk clones). Many binders from each library reconfirmed in an ELISA assay on Fab-containing cell supernatants, and several Fabs from each library were purified from periplasmic fractions and rank-ordered by affinity using Forte analysis.

Since no V-heavy middle cassettes that supported PCSK9 binding were identified, two mutagenic libraries were constructed which encoded either the parental murine residue or the closest human germline residue at all positions within the heavy chain CDR2 or FR3. Thus, an engineered human middle cassette library was built, screened, and antigen-binding clones identified. Changes to human germline in the Vh middle that supported binding in the context of individual clones were then combined to create one final middle cassette, and the affinity of a Fab containing this cassette in the context of the optimized reference Fab was confirmed to bind as well as the optimized reference Fab by Forte analysis.

From the libraries created, front-end and middle human cassettes that supported binding to PCSK9 antigen were successfully identified for both the heavy and light chains by CLBA. These binders were all confirmed by ELISA, then Fabs were purified and rank-ordered using the ForteBio Octet system. High-ranking cassettes for the heavy and light chains were combined into one final library by bridge PCR, and fully Humaneered™ Fabs that supported binding to PCSK9 were selected from this library by CLBA. In parallel with this, all the top-ranked cassettes or chains (the best Vh front-end, the engineered Vh middle, and the best full light chain) were combined together to create a single Fab SR066, which would be predicted to support high-affinity binding.

The sequences of the heavy and light chain variable regions for parent mouse mAb NVP-LFU720 and Humaneered™ Abs NVP-LGT209, NVP-LGT210 and NVP-LGT211 are shown in FIGS. 1-4, respectively.

Testing the Affinity of Fully Humaneered™ Fabs for PCSK9 Antigen Using Fortebio Octet Analysis The Humaneered™ SR066 Fab and three Fabs pulled out of the final combinatorial library (#1-2, #3-2, and #4-2) were expressed and purified. The binding kinetics of these four human Fabs were then compared to the kinetics of the optimized reference Fab SR038 using the ForteBio Octet system (numerical data summarized in Table 1).

TABLE 1

Affinity of fully Humaneered ™ Fabs for PCSK9

| Fab | $k_a$ | $k_d$ | $K_D$ |
|---|---|---|---|
| SR038 | 1.39E3 | 5.12E-4 | 3.69E-7 |
| SR066 | 3.25E3 | 1.08E-3 | 3.33E-7 |
| #1-2 | 6.91E3 | 2.16E-3 | 3.13E-7 |
| #3-2 | 5.92E3 | 1.46E-3 | 2.47E-7 |
| #4-2 | *** | *** | *** |

*** Not enough binding of the #4-2 Fab was detected to generate reliable kinetics data.

Protein concentration determination for these Fabs was difficult; as such, the off-rate (kd) data are much more reliable than the on-rate (ka) and KD data (only off-rates are concentration-independent). All four of the Humaneered™ Fabs tested appeared to have off-rates that were 3- to 4-fold "worse" (i.e., faster) than that of the optimized reference Fab. This decrease in affinity was likely due to the heavy chain front-ends in these clones, as all of the Fab binders selected from the original heavy chain front-end cassette library appeared to have "worse" off-rates than the optimized reference Fab (data not shown). As the heavy chain front-end contains CDR1, changes made to this CDR in the Vh front-end cassettes were a potential cause for the decreased affinity of the final Humaneered™ Fabs. Of the fully Humaneered™ Fabs, SR066 had the best off-rate (Table 1), and there are three differences between SR066 and the reference (mouse) sequence in heavy chain CDR1. To test the idea that changes made to CDRH1 were responsible for the decrease in affinity seen in all of our Humaneered™ Fabs, we simultaneously changed two residues at a time in CDRH1 of SR066 back to match the original murine residues, and expressed and purified these altered Fabs for Forte kinetic analysis.

One Fab with two simultaneous changes in CDRH1 (SR079) (Table 2) significantly improved the binding kinetics of SR066 (numerical data are summarized in Table 3). In fact, the SR079 Fab appeared to have an off-rate equivalent to that of the optimized reference (mouse) Fab SR038.

TABLE 2

| CDRH1 sequence of CDRH1-variant Fab SR079* | | |
|---|---|---|
| SR066 (humaneered) | TYYMN | SEQ ID NO: 64 |
| SR038 (mouse) | DMYMS | SEQ ID NO: 65 |
| SR079 (humaneered) | TMYMS | SEQ ID NO: 66 |

*Human (SR066-derived) or invariant residues are bolded; murine residues are normal font.

TABLE 3

| Affinity of SR079 Fab for PCSK9 | | | |
|---|---|---|---|
| Fab | $k_a$ | $k_d$ | $K_D$ |
| SR038 | 2.69E3 | 3.68E-4 | 1.37E-7 |
| SR079 | 6.01E3 | 3.26E-4 | 5.42E-8 |

Humaneered™ Fabs SR066, #1-2, #3-2, and #4-2 contained an "Asn-Gly" ("NG") amino acid sequence in CDRH2, which came from the original mouse antibody. This sequence is known to potentially undergo deamidation, an undesirable property for production. Therefore, at the same time as efforts were made to improve the affinity of the Humaneered™ SR066 Fab, two mutagenic libraries were constructed in the context of SR066, in which the "N" or the "G" were substituted with every possible amino acid except the original amino acid (e.g., in the "N removal library," "N" was substituted with every amino acid except for "N"). Fab-containing cell supernatants from this library were then screened by ELISA to identify clones that no longer had the "NG" sequence but still retained the SR066 level of binding (which is less than that of the optimized reference Fab SR038). The "N removal library" did not yield any Fabs that bound to the same extent as SR066, but the "G removal library" yielded Fabs with sufficient levels of binding that had a number of different substitutions at the "G" position. Of these, Fabs that had "NG" to "NE," "NA," and "NM" changes were chosen for purification and Forte kinetic analysis and found to have similar kinetics to that of the parent Fab SR066.

Engineering 7472 Human IgG to Improve Affinity
Vk Engineering

In order to create a completely human IgG, the Vh sequence of SR079 (modified version of SR066 that has improved affinity) up to CDRH2 was amplified and stitched to the sequence of a "G removal library" clone (containing "NE" in CDRH2) from CDRH2 through most of FR4 by bridge PCR. This Vh sequence was cloned into pRS5a-hIgG1 LALA+KpnI (silent IgG1 cloning vector that had been modified to add a KpnI site in FR4 without affecting the amino acid sequence of the Vh) at NruI (5') and KpnI (3') to create pSR074. The Vk (from FR1 up to partway through FR4) from SR066 was amplified and cloned into pRS5a-hkappa at AgeI and BsiWI to create pSR072. These vectors were verified by sequencing and co-transfected into 293 Freestyle cells. This IgG (referred to as "7472") was purified from antibody-containing cell media. Surprisingly, antibody 7472 had a significantly slower on-rate than the parental mouse antibody LFU720 by Biacore analysis (not shown). By interchanging each human chain with the complementary parental mouse chain, it was determined that this on-rate defect is due to a problem with the human light chain. Alterations were made to the pSR072 human light chain to rescue affinity (Table 4): the first four residues of the light chain were converted back to mouse sequence, and residues in the second half of CDR1 were converted back to mouse. This light chain was cloned into pRS5a-hkappa as described above to generate pJG10 and pJG01, and a full IgG was generated by co-transfection of pSR074 (Hc vector) and pJG10 (Lc vector) or pJG01 (Lc vector). Together, these changes partially rescued the affinity of the Humaneered™ antibody as determined by Biacore.

TABLE 4

| Changes made to IgG 7472 light chain | | | |
|---|---|---|---|
| LC N terminus (SEQ ID NO:) | | LC CDR1 (SEQ ID NO:) | |
| 7472 | EIVM (67) | 7472 | RASQSVSSSHVA (68) |
| LFU720 | QIVL (69) | LFU720 | SASSSVS--YMH (70) |
| pJG10 | QIVL (69) | pJG10 | RASQSVS--YMH (71) |

Table 4 shows alignments of portions of the light chains of the human antibody 7472, the parental mouse antibody LFU720, and the light chain encoded by pJG10. This portion is identical to the light chain encoded by pJG01. The light chain vectors were used for expression of the final Humaneered™ antibodies NVP-LGT209, NVP-LGT210 and NVP-LGT-211.

Affinity Maturation of CDRH3

In parallel with the light chain alterations, a Fab library was constructed to affinity mature CDR3 of the pSR074 heavy chain. In this library, CDR3 residues were substituted singly with every other amino acid, excluding the original residue. This library was screened by CLBA, binders were verified by ELISA, and the resultant Fabs were purified and tested by bio-layer interferometry to determine whether they had improved binding kinetics relative to the parental human Fab.

One CDRH3 substitution was identified which did significantly improve affinity: an A to N change (Table 5). This change was subsequently made in the context of the pSR074 heavy chain IgG expression plasmid; this new construct was called pJG04. The final Humaneered™ antibody NVP-LGT209 (LGT209) was generated by co-transfection of pJG04 (Hc) and pJG10 and subsequent purification. The final Humaneered™ antibody NVP-LGT210 (LGT210) was generated by co-transfection of pJG04 (Hc) and pJG01 and subsequent purification. This change was not introduced into antibody NVP-LGT211 (LGT211).

TABLE 5

Change made to IgG 7472 heavy chain CDR3

| CDRH3 sequence | | SEQ ID NO: |
|---|---|---|
| 7472 | CARSYYYYAMDY | 72 |
| LFU720 | CARSYYYYAMDY | 72 |
| pJG04 | CARSYYYYNMDY | 73 |

Table 5 shows alignments of heavy chain CDR3 of the human antibody 7472, the parental mouse antibody LFU720, and the heavy chain encoded by pJG04 (heavy chain vector used for expression of the final Humaneered™ antibodies NVP-LGT209 and NVP-LGT210). The A to N substitution is underlined.

Analysis of Binding Kinetics of NVP-LGT209, NVP-LGT210 and NVP-LGT211 Using the Solution Equilibrium Titration (SET) System Using the SET assay, the binding affinities of the NVP-LGT209, NVP-LGT210 and NVP-LGT211 antibodies to human PCSK9 were determined to be between 150-190 μM as indicated in Table 6. This suggests high affinity interaction between the antibodies and PCSK9 in solution.

TABLE 6

| Antibody | $K_D$ [pM] |
|---|---|
| LGT209 | 190 ± 50 |
| LGT210 | 150 ± 50 |
| LGT211 | 190 ± 50 |

Analysis of Antigen Specificity of NVP-LGT209 by ELISA

Figure 5A:
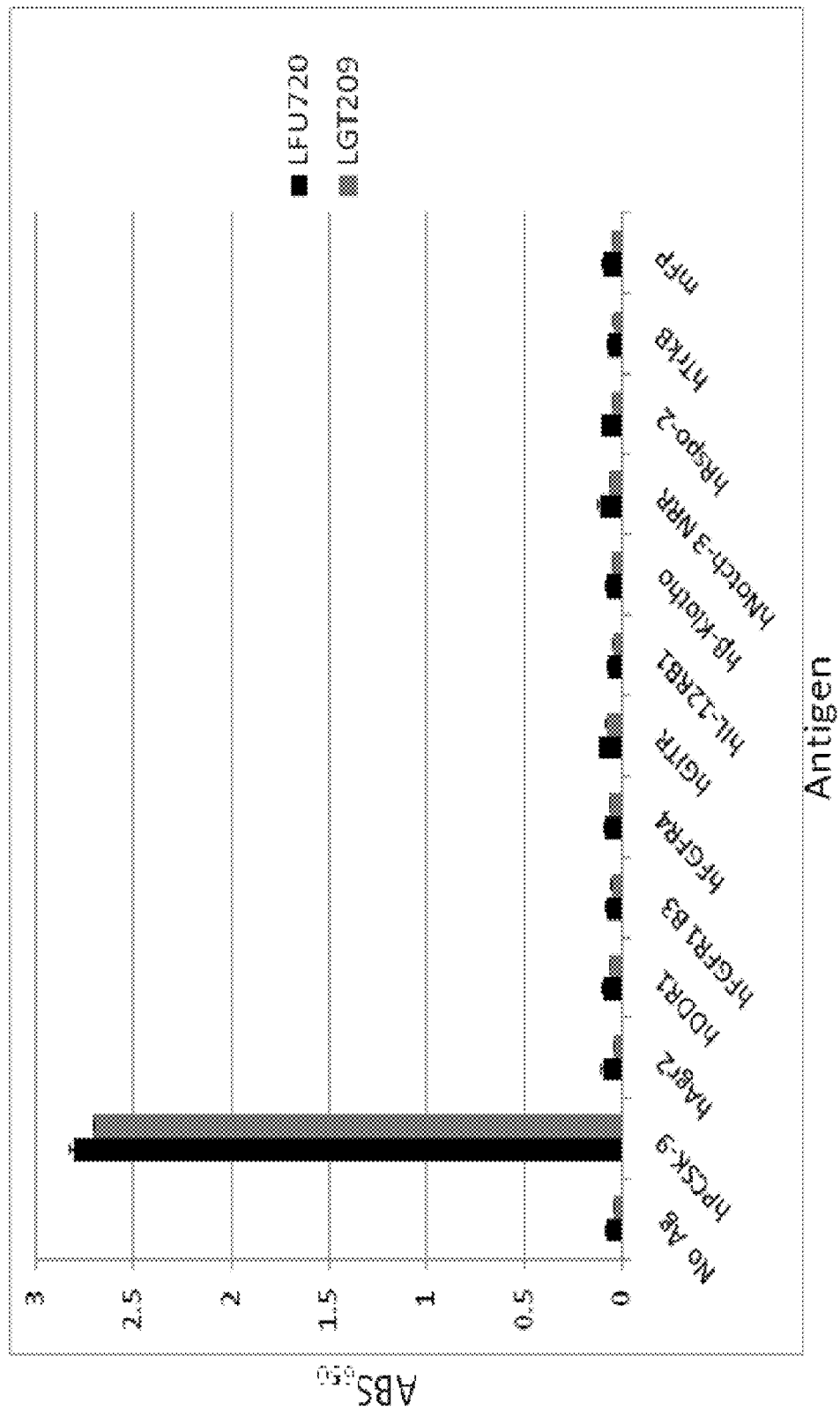
Figure 5C:
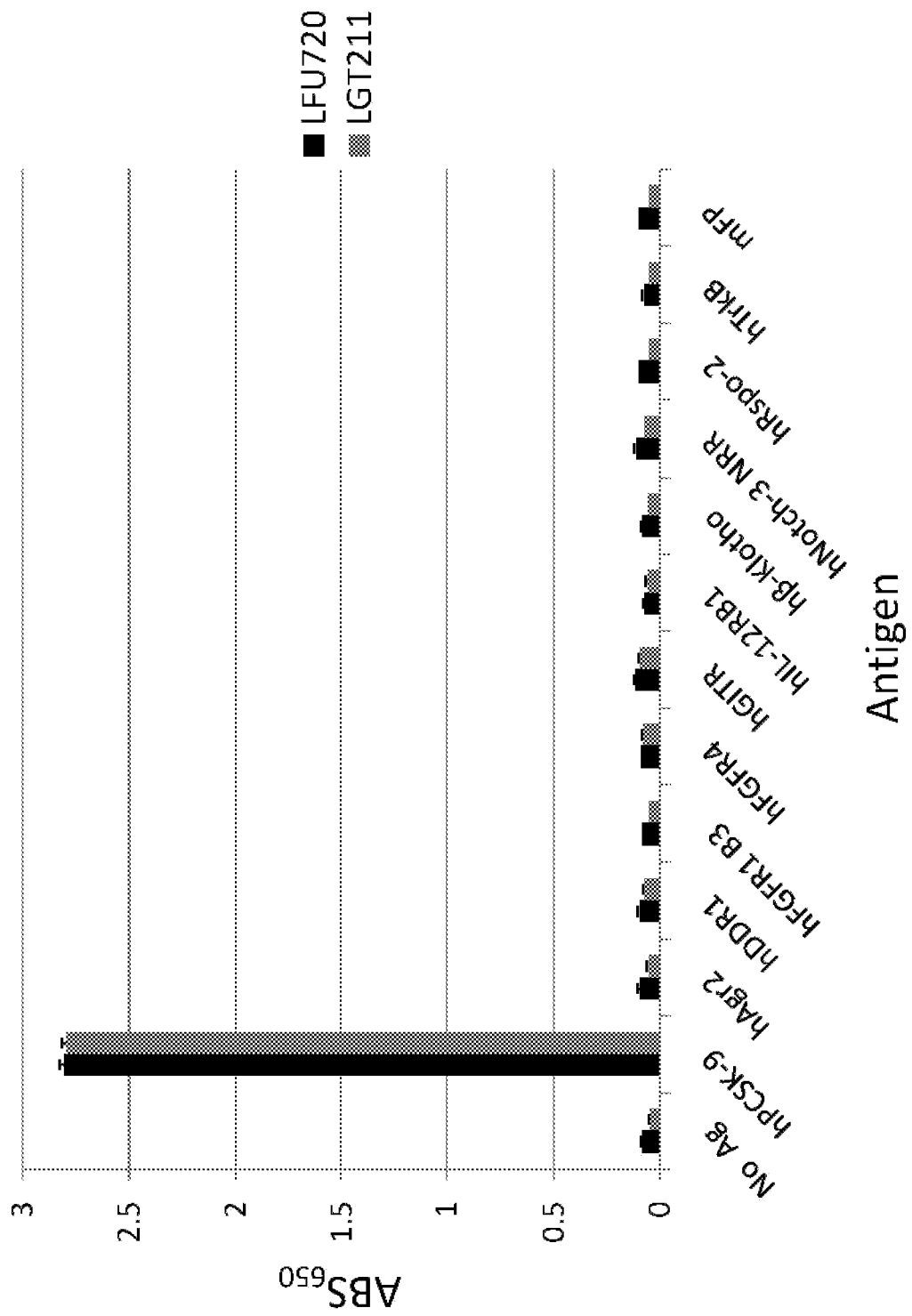

In order to test whether the antigen specificity of the parental mouse antibody LFU720 was retained in the final Humaneered™ IgGs, LGT209, LGT210 and LGT211, binding of the antibodies to a panel of human and mouse antigens (as well as human PCSK9) was tested in an ELISA assay. The results of this assay (FIGS. 5A-C) show that LGT209, LGT210 and LGT211 retain high specificity for PCSK9, similar to the murine antibody LFU720.

Antibody Binding to Human and Cynomolgus Macaque Pcsk9 Protein in ELISA

Figure 6A:
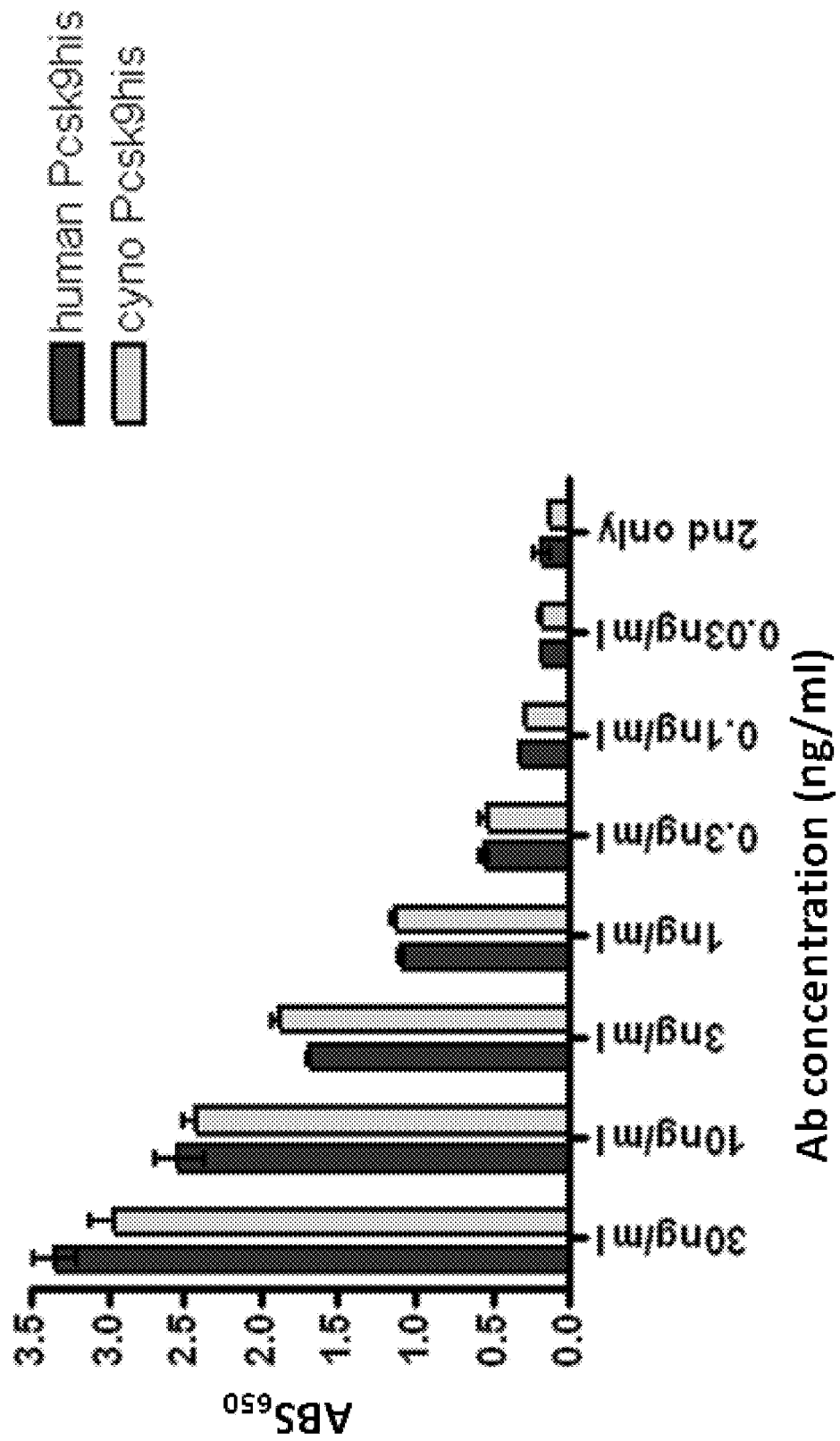
FIGS. 6A-C illustrate binding of NVP-LGT209 (A), NVP-LGT210 (B) and NVP-LGT-211 (C) in an ELISA to human and cyno Pcsk9. Secondary antibody is goat anti-mouse, diluted 1:5000. 2nd only is the secondary antibody alone control.
Figure 6B:
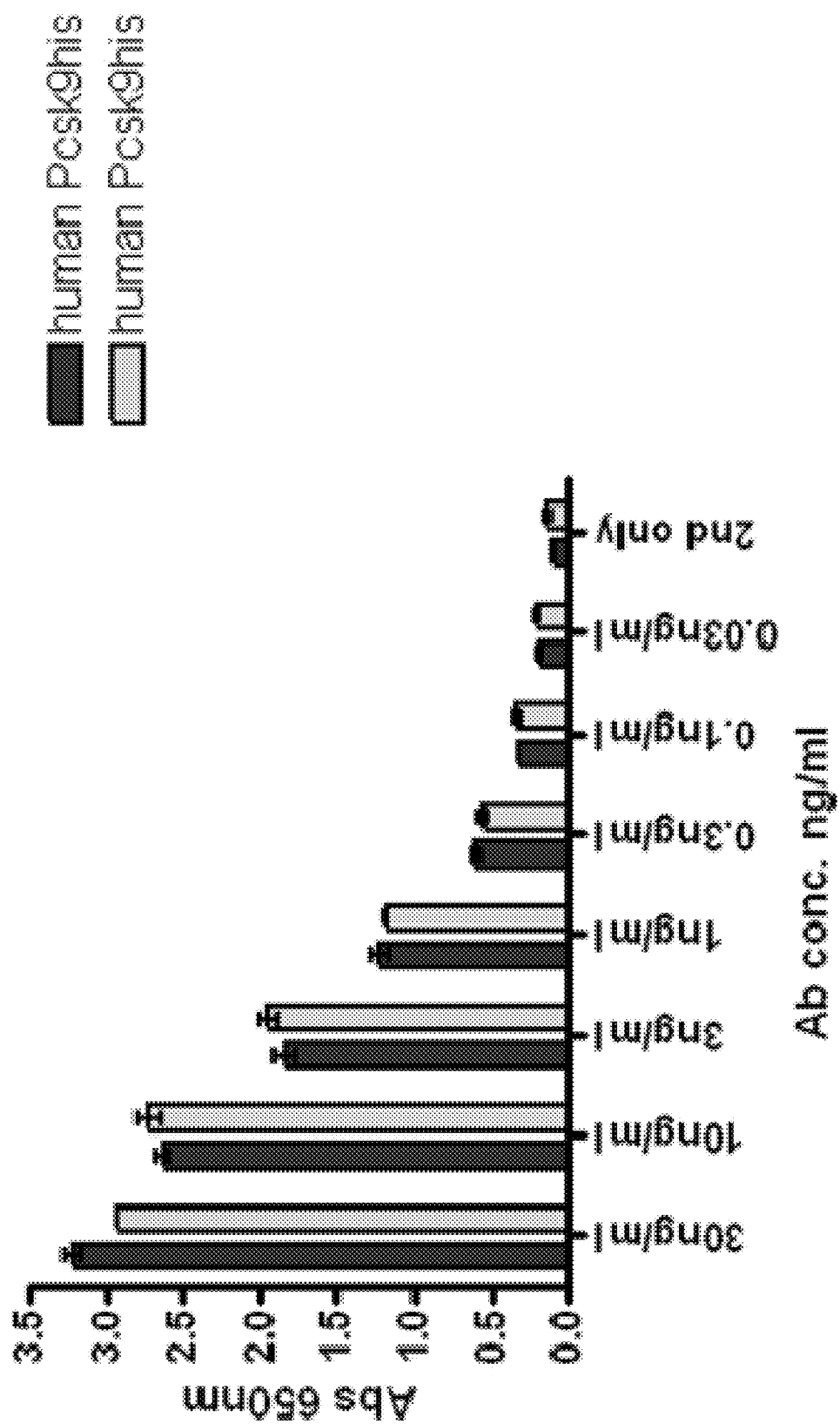
Figure 6C:
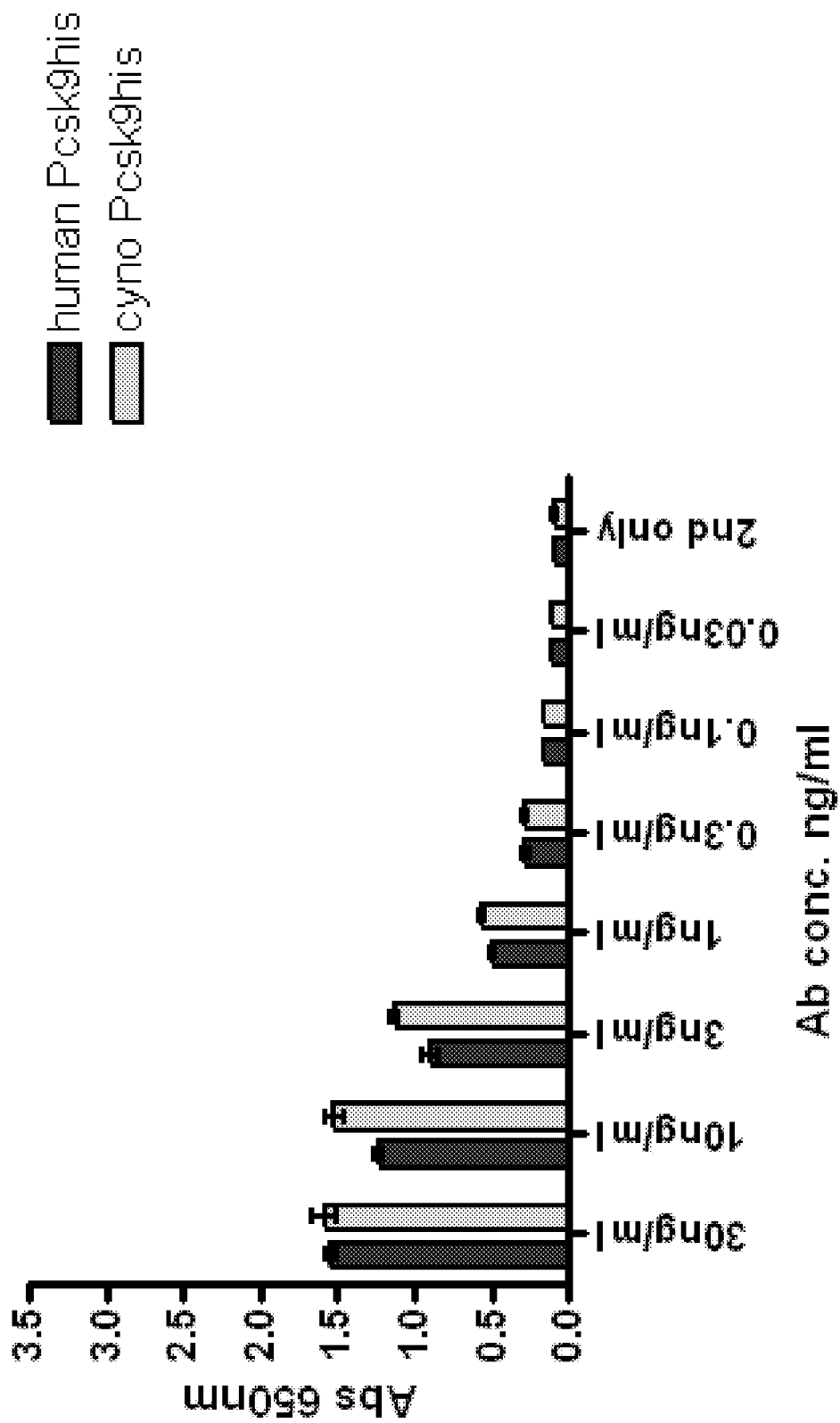
Figure 7:
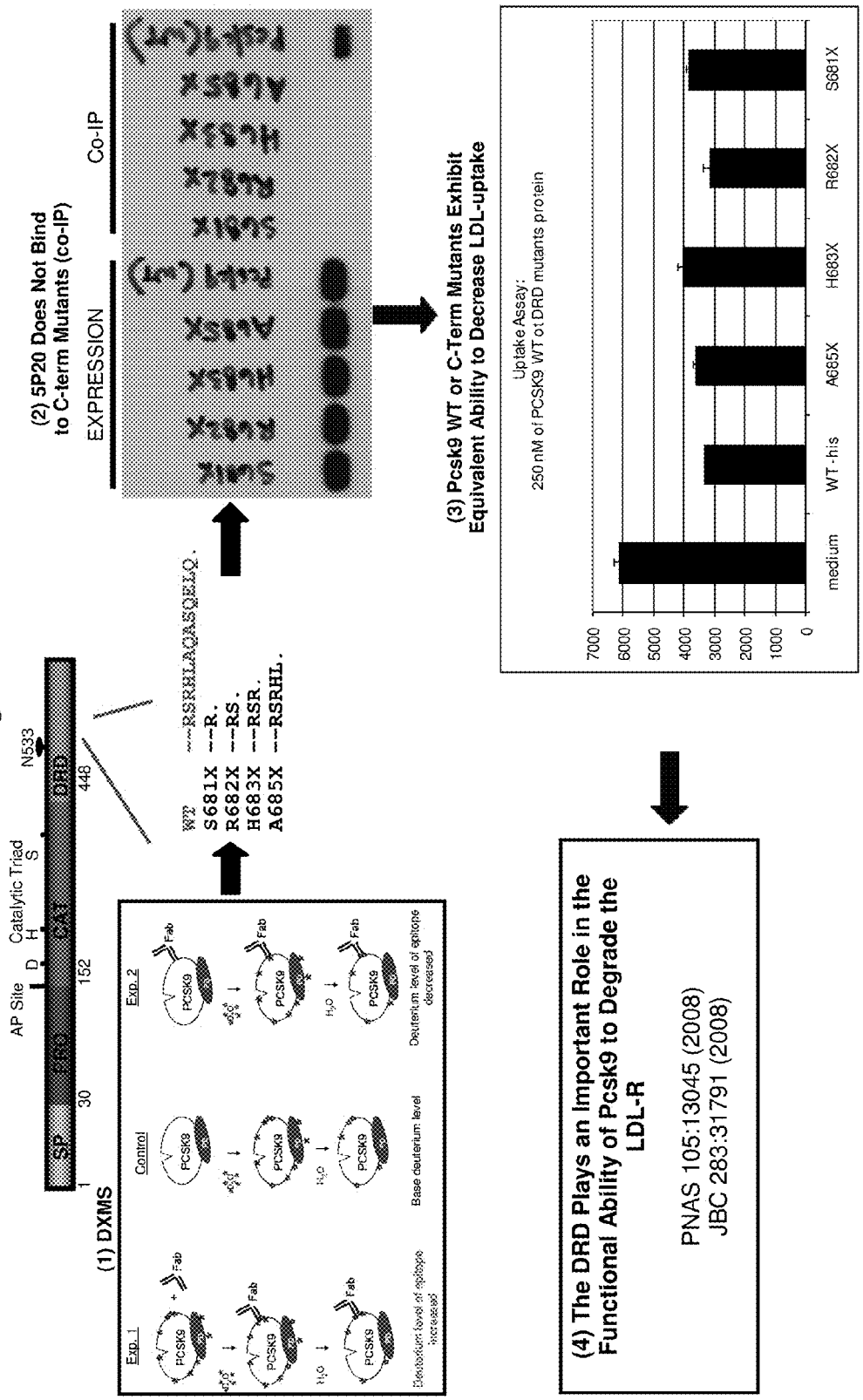
FIG. 7 illustrates that the parent mouse monoclonal antibody, NVP-LFU720 binds to the C-terminus of PCSK9, residues 680-692 (RSRHLAQASQELQ; SEQ ID NO:49). Humaneered™ antibodies LGT209, LGT210 and LGT211 compete for the same epitope. C-term mutant A685X=SEQ ID NO:56.
Figure 8:
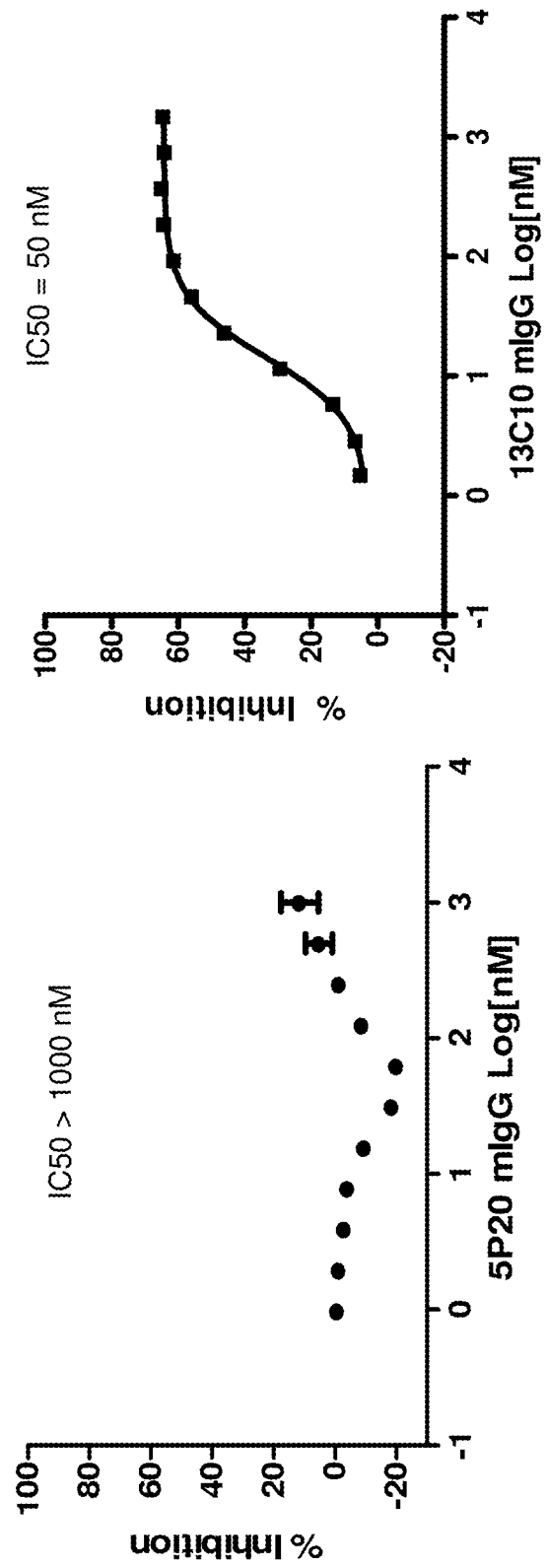
FIG. 8 illustrates that parent mouse antibody NVP-LFU720 (5P20) poorly disrupts the PCSK9 and LDL-R interaction, as determined in a time-resolved fluorescence resonance energy transfer (TR-FRET) biochemical assay. In contrast, 13C10 disrupts the PCSK9-LDL-R FRET interaction with an $IC_{50}$ of 50 nM. Human PCSK9 labeled with a fluorophore (hPCSK9-AF) was incubated with NVP-LFU720-AX-1 or 13C10 in assay buffer (20 mM HEPES, pH 7.2, 150 mM NaCl, 1 mM $CaCl_2$, 0.1% v/v Tween 20, and 0.1% w/v BSA) for 30 minutes at room temperature. This was followed by addition of europium-labeled LDL-R (hLDL-R-Eu), and further incubation at room temperature for 90 minutes, such that final concentrations were 8 nM hPcsk9-AF and 1 nM hLDL-R-Eu. TR-FRET signal (330 nm excitation and 665 nm emission) was measured with a plate reader (EnVision 2100, Perkin Elmer) and % inhibition in the presence of 5P20 or 13C10 calculated. $IC_{50}$ values were calculated by plotting percent inhibition values in Prism (GraphPad). Each data point represents mean±SD (n=4 replicates per point). Data are representative of at least two independent experiments.
Figure 9:
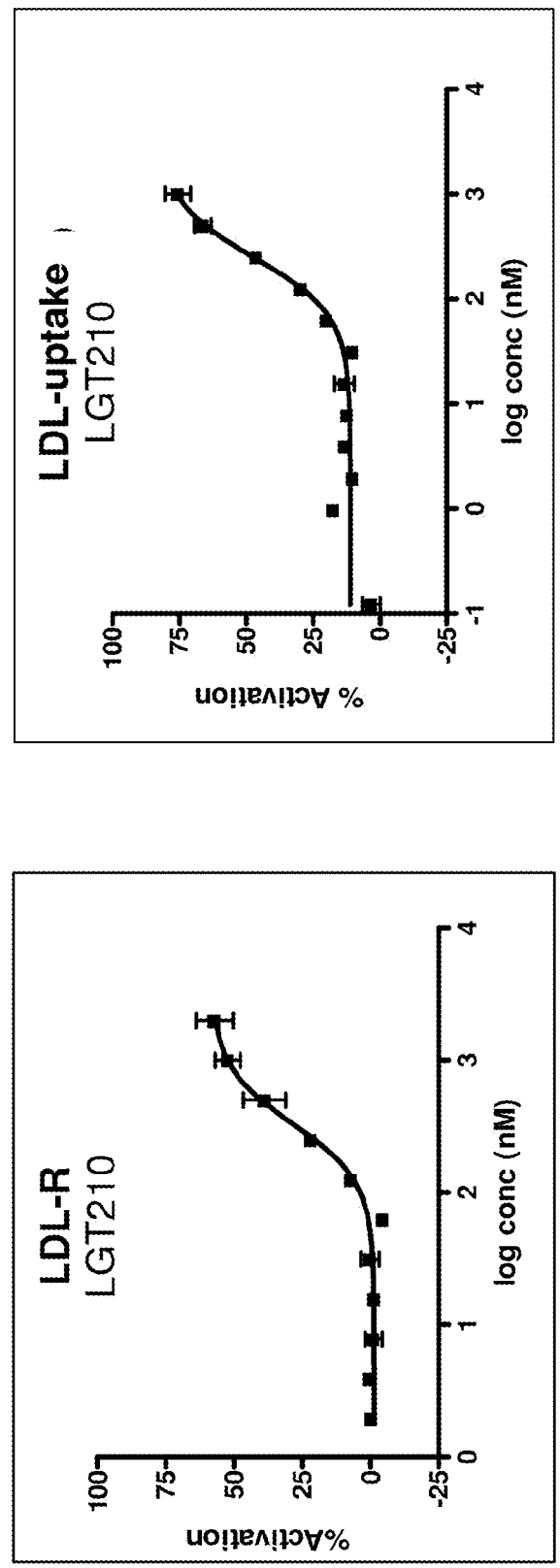
FIG. 9 illustrates that the Humaneered™ antibodies LGT209, LGT210 and LGT211 are equivalent to mouse antibody LFU720 at leading to increased LDL-R levels and LDL-uptake by HepG2 cells. For LDL-R measurement, cells were incubated with PCSK9-binding antibodies and labeled with anti-LDL-R antibodies. For LDL uptake, cells were incubated with PCSK9-binding antibodies, PCSK9, and DiI-LDL. LDL-R antibodies and DiI-LDL fluorescence were measured by flow cytometry. Mean+SEM for replicate measurements are shown for each assay. Results are representative of 3 independent experiments.

LGT209, LGT210 and LGT211 were evaluated for specific binding to human and cynomolgus macaque (cyno) Pcsk9. This ELISA assay shows that, like the parental mouse antibody LFU720, the Humaneered™ antibodies LGT209, LGT210 and LGT211 are able to bind both human and cyno Pcsk9 in a similar manner (FIGS. 6A-C).

Bio-Layer Interferometry-Based Epitope Competition Assay

In order to test whether the epitope specificity of the parent murine antibody NVP-LFU720 was retained in the final Humaneered™ antibodies LGT209, LGT210 and LGT211, a competition assay using the ForteBio Octet system was developed. The Humaneered™ antibodies LGT209, LGT210 and LGT211 block binding of the parental mouse antibody NVP-LFU720, indicating that the Humaneered™ antibodies retain the epitope specificity of the original murine antibody. Similar results were obtained when the order of loading of antibodies was switched, i.e., NVP-LFU720 bound first, followed by the Humaneered™ antibody.

Amino Acid Sequence of Humaneered™ Antibodies LGT209, LGT210 and LGT211 and Percent Identity to Human Germline Sequence The variable region amino acid sequences of final Humaneered™ IgG LGT209, LGT210 and LGT211 are shown in FIGS. 2-4, respectively; CDRs are underlined and in bold. Nucleotide sequences are included in the sequence listing.

The percent identity to human germline sequences for antibodies LGT209, LGT210 and LGT211 was determined by aligning the Vh and Vk amino acid sequences against a single human germline sequence (Vh1 1-02 and Vk3 A27, respectively; Table 7). Residues in CDRH3 and CDRL3 were omitted from the calculation for each chain.

TABLE 7

| Percent identity of antibodies LGT209, LGT210 and LGT211 to human germline sequences | |
|---|---|
| Vh versus Vh1 1-02 | Vk versus Vk3 A27 |
| 89% | 91% |

Additional information regarding the functional characterization of the humaneered antibodies is discussed in the figure legends of FIGS. 8-14.

Example 3

Mutational Analyses of PCSK9 Antagonist Antibodies NVP-LGT209, NVP-LGT210 and NVP-LGT211

Variants of PCSK9 Antagonist Antibodies NVP-LGT209, NVP-LGT210 and NVP LGT211 were evaluated for their ability to bind to PCSK9. The results are summarized as follows:

With respect to the heavy chain CDR1, TMYMS (SEQ ID NO:66), only clones that contain the original mouse residues (in bold) retain the binding kinetics of mouse Ab (as determined by biolayer interferometry analysis). Therefore, these residues within the heavy chain CDR1 play a role in binding.

With respect to the heavy chain CDR2, RIDPAN EHTNYAQKFQG (SEQ ID NO:74), residues in bold were not altered in antibody binders pulled out of a library encoding either original (mouse) residue or the corresponding residue in the closest human germline sequence at each position (screened by ELISA). Therefore, the bolded residues play a role in binding. Conservative substitutions are tolerated at the position indicated by the underlined Glu residue, for example, this position can be A, E or D, as determined by ELISA and confirmed by biolayer interferometry.

With respect to the heavy chain CDR3, SYYYY(A/N)MD Y (SEQ ID NO:75), residues in bold were not altered in clones pulled out of an affinity maturation library encoding all amino acid possibilities (excluding the original aa) at each position. Therefore, the bolded residues play a role in binding. Conservative substitutions are tolerated at the position indicated by the underlined Ala or Asn residue, for example, this position can be A, N or Q, as determined by Biacore. Conservative substitutions are tolerated at the position indicated by the underlined Tyr residue, for example, this position can be A, F, S, V or Y, as determined by Biacore.

With respect to the light chain FR1, (E/Q)IV(M/ L)TQSPATLSVSPGERATLSC (SEQ ID NO:76), conservative substitutions are tolerated at the underlined positions 1 and 4, as determined by Biacore. For example, the amino acid at position 1 can be A, D, E, N or Q. The amino acid at position 4 can be V, I, L or M. Positions 1-4 as QIVL (SEQ IOD NO:69) (as in the mouse parent LFU720, LGT209 and LGT211 Vk) have improved binding over positions 1-4 as EIVM (SEQ ID NO:67) (as in LGT210 Vk), as determined by Biacore.

With respect to the light chain CDR1, RASQSVSYMH (SEQ ID NO:71), the spacing of the bolded residues had consequences for binding, as a human clone with 2 extra amino acids in this portion of Lc CDR1 was compromised in affinity. Therefore, the bolded residues play a role in binding.

With respect to the light chain CDR3, LQWSSDPPT (SEQ ID NO:26), changes to human germline at these positions are not tolerated, as determined by ELISA. Therefore, the bolded residues play a role in binding.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession entries cited herein are hereby incorporated by reference in their entirety for all purposes.

What is claimed is:

1. An antibody that binds to proprotein convertase subtilisin/kexin type 9 (PCSK9), wherein the antibody comprises a heavy chain V-segment and a light chain V-segment, each of which comprises a complementarity determining region 1 (CDR1), a complementarity determining region 2 (CDR2), and a complementarity determining region 3 (CDR3); wherein:
   i) the CDR1 of the heavy chain V-segment comprises SEQ ID NO:7;
   ii) the CDR2 of the heavy chain V-segment comprises SEQ ID NO:10;
   iii) the heavy chain CDR3 comprises an amino acid sequence selected from the group consisting of SEQ ID NO:12 and SEQ ID NO:13;
   iv) the CDR1 of the light chain V-segment comprises SEQ ID NO:21;
   v) the CDR2 of the light chain V-segment comprises SEQ ID NO:24; and
   vi) the light chain CDR3 comprises SEQ ID NO:26.

2. The antibody of claim 1, wherein the heavy chain variable region has at least 90% amino acid sequence identity to the variable region of SEQ ID NO:40 and the light chain variable region has at least 90% amino acid sequence identity to the variable region of SEQ ID NO:41.

3. The antibody of claim 1, wherein the heavy chain variable region has at least 95% amino acid sequence identity to the variable region of SEQ ID NO:40 and the light chain variable region has at least 95% amino acid sequence identity to the variable region of SEQ ID NO:41.

4. The antibody of claim 1, wherein the antibody comprises a heavy chain comprising SEQ ID NO:40 and a light chain comprising SEQ ID NO:41.

5. The antibody of claim 1, wherein the heavy chain variable region has at least 90% amino acid sequence identity to the variable region selected from the group consisting of SEQ ID NO:2 and SEQ ID NO:4 and the light chain variable region has at least 90% amino acid sequence identity to the variable region selected from the group consisting of SEQ ID NO:16 and SEQ ID NO:18.

6. The antibody of claim 1, wherein the heavy chain variable region has at least 95% amino acid sequence identity to the variable region selected from the group consisting of SEQ ID NO:2 and SEQ ID NO:4 and the light chain variable region has at least 95% amino acid sequence identity to the variable region selected from the group consisting of SEQ ID NO:16 and SEQ ID NO:18.

7. The antibody of claim 1, wherein the heavy chain variable region comprises the amino acid sequence selected from the group consisting of SEQ ID NO:2 and SEQ ID NO:4 and the light chain variable region comprises the amino acid sequence selected from the group consisting of SEQ ID NO:16 and SEQ ID NO:18.

8. The antibody of claim 1, wherein the antibody is a FAb' fragment.

9. The antibody of claim 1, wherein the antibody is an IgG.

10. The antibody of claim 1, wherein the antibody is a single chain antibody (scFv).

11. The antibody of claim 1, wherein the antibody comprises human constant regions.

12. The antibody of claim 1, wherein the antibody is linked to a carrier protein.

13. The antibody of claim 1, wherein the antibody is PEGylated.

14. An antibody that specifically binds PCSK9, wherein the antibody comprises a heavy chain variable region and a light chain variable region, wherein the heavy chain variable region and the light chain variable region each comprise the following three complementarity determining regions (CDRs): CDR1, CDR2 and CDR3; wherein:
   i) the CDR1 of the heavy chain variable region comprises the amino acid sequence of SEQ ID NO:8;
   ii) the CDR2 of the heavy chain variable region comprises the amino acid sequence of SEQ ID NO:11;
   iii) the CDR3 of the heavy chain variable region comprises the amino acid sequence of SEQ ID NO:14;
   iv) the CDR1 of the light chain variable region comprises the amino acid sequence of SEQ ID NO:22;
   v) the CDR2 of the light chain variable region comprises the amino acid sequence of SEQ ID NO:25;
   vi) the CDR3 of the light chain variable region comprises the amino acid sequence of SEQ ID NO:26.

15. An antibody that specifically binds PCSK9, wherein the antibody comprises a heavy chain variable region and a light chain variable region, wherein the heavy chain variable region and the light chain variable region each comprise the following three complementarity determining regions (CDRs): CDR1, CDR2 and CDR3, wherein:
   i) the CDR1 of the heavy chain variable region comprises the amino acid sequence selected from the group consisting of SEQ ID NO:6 and SEQ ID NO:7;
   ii) the CDR2 of the heavy chain variable region comprises the amino acid sequence selected from the group consisting of SEQ ID NO:9 and SEQ ID NO:10;
   iii) the CDR3 of the heavy chain variable region comprises the amino acid sequence selected from the group consisting of SEQ ID NO:12 and SEQ ID NO:13;
   iv) the CDR1 of the light chain variable region comprises the amino acid sequence selected from the group consisting of SEQ ID NO:20 and SEQ ID NO:21;
   v) the CDR2 of the light chain variable region comprises the amino acid sequence selected from the group consisting of SEQ ID NO:23 and SEQ ID NO:24;
   vi) the CDR3 of the light chain variable region comprises the amino acid sequence of SEQ ID NO:26.

16. A composition comprising an antibody of claim 1 and a physiologically compatible excipient.

17. The composition of claim 16, wherein the composition further comprises a second agent that reduces low density lipoprotein cholesterol (LDL-C) levels in an individual.

18. The composition of claim 17, wherein the second agent is a statin.

19. The composition of claim 18, wherein the statin is selected from the group consisting of atorvastatin, cerivastatin, fluvastatin, lovastatin, mevastatin, pitavastatin, pravastatin, rosuvastatin, and simvastatin.

20. The composition of claim 17, wherein the second agent is selected from the group consisting of fibrates, niacin and analogs thereof, cholesterol absorption inhibitors, bile acid sequestrants, thyroid hormone mimetics, a microsomal triglyceride transfer protein (MTP) inhibitor, a diacylglycerol acyltransferase (DGAT) inhibitor, an inhibitory nucleic acid targeting PCSK9 and an inhibitory nucleic acid targeting apoB100.

* * * * *

SEQUENCE LISTING

```
<160> NUMBER OF SEQ ID NOS: 76

<210> SEQ ID NO 1
<211> LENGTH: 118
<212> TYPE: PRT
<213> ORGANISM: Mus musculus
<220> FEATURE:
<223> OTHER INFORMATION: mouse anti-PCSK9 monoclonal antibody LFU720
      heavy chain variable region (FR1-FR4)

<400> SEQUENCE: 1

Glu Val Gln Leu Gln Gln Ser Gly Ala Glu Leu Met Lys Pro Gly Ala
 1               5                  10                  15

Ser Val Lys Leu Ser Cys Thr Ala Ser Gly Phe Asn Ile Lys Asp Met
            20                  25                  30

Tyr Met Ser Trp Val Arg Gln Arg Pro Glu Gln Gly Leu Glu Trp Ile
        35                  40                  45

Gly Arg Ile Asp Pro Ala Asn Gly His Thr Asn Tyr Asp Pro Lys Phe
    50                  55                  60

Gln Ala Lys Ala Thr Ile Thr Thr Asp Thr Ser Ser Lys Thr Ala Tyr
65                  70                  75                  80

Leu His Leu Ser Ser Leu Thr Ser Glu Asp Thr Ala Val Tyr Tyr Cys
                85                  90                  95

Ala Arg Ser Tyr Tyr Tyr Ala Met Asp Tyr Trp Gly Gln Gly Thr
            100                 105                 110

Ser Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: synthetic anti-PCSK9 monoclonal antibody pJG04
      (clones LGT-209 and LGT-210) Vh heavy chain
      variable region (FR1-FR4)

<400> SEQUENCE: 2

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60
```

```
Gln Gly Arg Val Thr Met Thr Arg Asp Thr Ser Ile Ser Thr Ala Tyr
 65                  70                  75                  80

Met Glu Leu Ser Arg Leu Thr Ser Asp Asp Thr Ala Val Tyr Tyr Cys
                 85                  90                  95

Ala Arg Ser Tyr Tyr Tyr Tyr Asn Met Asp Tyr Trp Gly Gln Gly Thr
            100                 105                 110

Leu Val Thr Val Ser Ser
            115

<210> SEQ ID NO 3
<211> LENGTH: 448
<212> TYPE: PRT
<213> ORGANISM: Artificial Sequence
<220> FEATURE:
<223> OTHER INFORMATION: synthetic anti-PCSK9 monoclonal antibody pJG04
      (clones LGT-209 and LGT-210) Vh heavy chain
      includoing IgG1 constant chain
<220> FEATURE:
<221> NAME/KEY: VARIANT
<222> LOCATION: (235)...(236)
<223> OTHER INFORMATION: Xaa = Ala or Leu

<400> SEQUENCE: 3

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Ser Thr Met
                 20                  25                  30

Tyr Met Ser Trp Val Arg Gln Ala Pro Gly Gln Gly Leu Glu Trp Met
             35                  40                  45

Gly Arg Ile Asp Pro Ala Asn Glu His Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Thr Ser Asp Asp Thr Ala Val Tyr Tyr Cys
                 85                  90                  95

Ala Arg Ser Tyr Tyr Tyr Tyr Asn Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Xaa Xaa Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

```
                275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 4
<211> LENGTH: 118
<212> TYPE: PRT
<213> ORGANISM: Artificial Sequence
<220> FEATURE:
<223> OTHER INFORMATION: synthetic anti-PCSK9 monoclonal antibody pSR74
      (clone LGT-211) Vh heavy chain variable region
      (FR1-FR4)

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Ser Tyr Tyr Tyr Tyr Ala Met Asp Tyr Trp Gly Gln Gly Thr
            100                 105                 110

Leu Val Thr Val Ser Ser
        115

<210> SEQ ID NO 5
<211> LENGTH: 448
<212> TYPE: PRT
<213> ORGANISM: Artificial Sequence
<220> FEATURE:
<223> OTHER INFORMATION: synthetic anti-PCSK9 monoclonal antibody pSR74
      (clone LGT-211) Vh heavy chain including IgG1
      constant chain
<220> FEATURE:
<221> NAME/KEY: VARIANT
<222> LOCATION: (235)...(236)
```

<223> OTHER INFORMATION: Xaa = Ala or Leu

<400> SEQUENCE: 5

```
Gln Val Gln Leu Val Gln Ser Gly Ala Glu Val Lys Pro Gly Ala
  1               5                  10                  15

Ser Val Lys Val Ser Cys Lys Ala Ser Gly Tyr Thr Phe Ser Thr Met
             20                  25                  30

Tyr Met Ser Trp Val Arg Gln Ala Pro Gly Gln Gly Leu Glu Trp Met
         35                  40                  45

Gly Arg Ile Asp Pro Ala Asn Glu His Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Thr Ser Asp Asp Thr Ala Val Tyr Tyr Cys
                 85                  90                  95

Ala Arg Ser Tyr Tyr Tyr Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Xaa Xaa Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Val Leu Asp
385                 390                 395                 400

Ser Asp Gly Ser Phe Phe Leu Tyr Ser Lys Leu Thr Val Asp Lys Ser
```

```
                       405                 410                 415
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 6
<211> LENGTH: 5
<212> TYPE: PRT
<213> ORGANISM: Artificial Sequence
<220> FEATURE:
<223> OTHER INFORMATION: synthetic mouse anti-PCSK9 monoclonal antibody
      LFU720 heavy chain complementarity determining
      region 1 (CDR1)

<400> SEQUENCE: 6

Asp Met Tyr Met Ser
1               5

<210> SEQ ID NO 7
<211> LENGTH: 5
<212> TYPE: PRT
<213> ORGANISM: Artificial Sequence
<220> FEATURE:
<223> OTHER INFORMATION: anti-PCSK9 monoclonal antibody clones LGT-209,
      LGT-210 and LGT-211 heavy chain complementarity
      determining region 1 (CDR1)

<400> SEQUENCE: 7

Thr Met Tyr Met Ser
1               5

<210> SEQ ID NO 8
<211> LENGTH: 5
<212> TYPE: PRT
<213> ORGANISM: Artificial Sequence
<220> FEATURE:
<223> OTHER INFORMATION: anti-PCSK9 monoclonal antibody consensus heavy
      chain complementarity determining region 1 (CDR1)
<220> FEATURE:
<221> NAME/KEY: VARIANT
<222> LOCATION: (1)...(1)
<223> OTHER INFORMATION: Xaa = Asp or Thr

<400> SEQUENCE: 8

Xaa Met Tyr Met Ser
1               5

<210> SEQ ID NO 9
<211> LENGTH: 17
<212> TYPE: PRT
<213> ORGANISM: Artificial Sequence
<220> FEATURE:
<223> OTHER INFORMATION: synthetic mouse anti-PCSK9 monoclonal antibody
      LFU270 heavy chain complementarity determining
      region 2 (CDR2)

<400> SEQUENCE: 9

Arg Ile Asp Pro Ala Asn Gly His Thr Asn Tyr Asp Pro Lys Phe Gln
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: synthetic anti-PCSK9 monoclonal antibody clones
```

```
              LGT-209, LGT-210 and LGT-211 heavy chain
              complementarity determining region 2 (CDR2)

<400> SEQUENCE: 10

Arg Ile Asp Pro Ala Asn Glu His Thr Asn Tyr Ala Gln Lys Phe Gln
 1               5                  10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: synthetic anti-PCSK9 monoclonal antibody
      consensus heavy chain complementarity determining region 2
      (CDR2)
<220> FEATURE:
<221> NAME/KEY: VARIANT
<222> LOCATION: (7)...(7)
<223> OTHER INFORMATION: Xaa = Ala, Glu or Gly
<220> FEATURE:
<221> NAME/KEY: VARIANT
<222> LOCATION: (12)...(12)
<223> OTHER INFORMATION: Xaa = Ala or Asp
<220> FEATURE:
<221> NAME/KEY: VARIANT
<222> LOCATION: (13)...(13)
<223> OTHER INFORMATION: Xaa = Pro or Gln
<220> FEATURE:
<221> NAME/KEY: VARIANT
<222> LOCATION: (17)...(17)
<223> OTHER INFORMATION: Xaa = Ala or Gly

<400> SEQUENCE: 11

Arg Ile Asp Pro Ala Asn Xaa His Thr Asn Tyr Xaa Xaa Lys Phe Gln
 1               5                  10                  15

Xaa

<210> SEQ ID NO 12
<211> LENGTH: 9
<212> TYPE: PRT
<213> ORGANISM: Artificial Sequence
<220> FEATURE:
<223> OTHER INFORMATION: synthetic anti-PCSK9 monoclonal antibody pJG04
      (clones LGT-209 and LGT-210) Vh heavy chain
      complementarity determining region 3 (CDR3)

<400> SEQUENCE: 12

Ser Tyr Tyr Tyr Tyr Asn Met Asp Tyr
 1               5

<210> SEQ ID NO 13
<211> LENGTH: 9
<212> TYPE: PRT
<213> ORGANISM: Artificial Sequence
<220> FEATURE:
<223> OTHER INFORMATION: synthetic mouse anti-PCSK9 monoclonal antibody
      LFU270 and anti-PCSK9 monoclonal antibody pSR74
      (clone LGT-211) Vh heavy chain complementarity
      determining region 3 (CDR3)

<400> SEQUENCE: 13

Ser Tyr Tyr Tyr Tyr Ala Met Asp Tyr
 1               5

<210> SEQ ID NO 14
<211> LENGTH: 9
<212> TYPE: PRT
<213> ORGANISM: Artificial Sequence
<220> FEATURE:
```

-continued

```
<223> OTHER INFORMATION: synthetic anti-PCSK9 monoclonal antibody
      consensus heavy chain complementarity determining region 3
      (CDR3)
<220> FEATURE:
<221> NAME/KEY: VARIANT
<222> LOCATION: (6)...(6)
<223> OTHER INFORMATION: Xaa = Ala or Asn
<220> FEATURE:
<221> NAME/KEY: VARIANT
<222> LOCATION: (9)...(9)
<223> OTHER INFORMATION: Xaa = Ala, Phe, Ser, Val or Tyr

<400> SEQUENCE: 14

Ser Tyr Tyr Tyr Tyr Xaa Met Asp Xaa
 1               5

<210> SEQ ID NO 15
<211> LENGTH: 106
<212> TYPE: PRT
<213> ORGANISM: Mus musculus
<220> FEATURE:
<223> OTHER INFORMATION: mouse anti-PCSK9 monoclonal antibody LFU720
      light chain variable region (FR1-FR4)

<400> SEQUENCE: 15

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
            20                  25                  30

His Trp Tyr Gln Gln Lys Pro Gly Ser Ser Pro Arg Leu Trp Ile Tyr
        35                  40                  45

Leu Thr Phe Asn Leu Ala Ser Gly Val Pro Ala Arg Phe Ser Gly Ser
    50                  55                  60

Gly Ser Gly Thr Ser Tyr Ser Leu Ser Ile Ser Ser Met Glu Ala Glu
65                  70                  75                  80

Asp Ala Ala Thr Tyr Tyr Cys Leu Gln Trp Ser Ser Asp Pro Pro Thr
                85                  90                  95

Phe Gly Ser Gly Thr Lys Leu Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: synthetic anti-PCSK9 monoclonal antibody pJG10
      (clones LGT-209 and LGT-211) Vk light chain
      variable region (FR1-FR4)

<400> SEQUENCE: 16

Gln Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Gly Val Phe Arg Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys
            100                 105
```

<210> SEQ ID NO 17
<211> LENGTH: 213
<212> TYPE: PRT
<213> ORGANISM: Artificial Sequence
<220> FEATURE:
<223> OTHER INFORMATION: synthetic anti-PCSK9 monoclonal antibody pJG10
(clones LGT-209 and LGT-211) Vk light chain
including kappa constant chain

<400> SEQUENCE: 17

Gln Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Gly Val Phe Arg Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 18
<211> LENGTH: 106
<212> TYPE: PRT
<213> ORGANISM: Artificial Sequence
<220> FEATURE:
<223> OTHER INFORMATION: synthetic anti-PCSK9 monoclonal antibody pJG01
(clone LGT-210) Vk light chain variable region
(FR1-FR4)

<400> SEQUENCE: 18

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Gly Val Phe Arg Arg Ala Thr Gly Ile Pro Asp Arg Phe Ser Gly Ser
    50                  55                  60

```
Gly Ser Gly Thr Asp Phe Thr Leu Thr Ile Gly Arg Leu Glu Pro Glu
 65                  70                  75                  80

Asp Phe Ala Val Tyr Tyr Cys Leu Gln Trp Ser Ser Asp Pro Pro Thr
                 85                  90                  95

Phe Gly Gln Gly Thr Lys Leu Glu Ile Lys
            100                 105

<210> SEQ ID NO 19
<211> LENGTH: 213
<212> TYPE: PRT
<213> ORGANISM: Artificial Sequence
<220> FEATURE:
<223> OTHER INFORMATION: synthetic anti-PCSK9 monoclonal antibody pJG01
      (clone LGT-210) Vk light chain including kappa
      constant chain

<400> SEQUENCE: 19

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Tyr Met
                 20                  25                  30

His Trp Tyr Gln Gln Lys Pro Gly Gln Ala Pro Arg Leu Leu Ile Tyr
             35                  40                  45

Gly Val Phe Arg Arg Ala Thr Gly Ile Pro Asp Arg Phe Ser Gly Ser
 50                  55                  60

Gly Ser Gly Thr Asp Phe Thr Leu Thr Ile Gly Arg Leu Glu Pro Glu
 65                  70                  75                  80

Asp Phe Ala Val Tyr Tyr Cys Leu Gln Trp Ser Ser Asp Pro Pro Thr
                 85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 20
<211> LENGTH: 10
<212> TYPE: PRT
<213> ORGANISM: Artificial Sequence
<220> FEATURE:
<223> OTHER INFORMATION: synthetic mouse anti-PCSK9 monoclonal antibody
      LFU720 light chain complementarity determining
      region 1 (CDR1)

<400> SEQUENCE: 20

Ser Ala Ser Ser Ser Val Ser Tyr Met His
  1               5                  10

<210> SEQ ID NO 21
```

```
<211> LENGTH: 10
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 light chain
      complementarity determining region 1 (CDR1)

<400> SEQUENCE: 21

Arg Ala Ser Gln Ser Val Ser Tyr Met His
1               5                   10

<210> SEQ ID NO 22
<211> LENGTH: 10
<212> TYPE: PRT
<213> ORGANISM: Artificial Sequence
<220> FEATURE:
<223> OTHER INFORMATION: synthetic anti-PCSK9 monoclonal antibody
      consensus light chain complementarity determining region 1
      (CDR1)
<220> FEATURE:
<221> NAME/KEY: VARIANT
<222> LOCATION: (1)...(1)
<223> OTHER INFORMATION: Xaa = Arg or Ser
<220> FEATURE:
<221> NAME/KEY: VARIANT
<222> LOCATION: (4)...(4)
<223> OTHER INFORMATION: Xaa = Gln or Ser

<400> SEQUENCE: 22

Xaa Ala Ser Xaa Ser Val Ser Tyr Met His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: synthetic mouse anti-PCSK9 monoclonal antibody
      LFU720 light chain complementarity determining
      region 2 (CDR2)

<400> SEQUENCE: 23

Leu Thr Phe Asn Leu Ala Ser
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 light chain
      complementarity determining region 1 (CDR1)

<400> SEQUENCE: 24

Gly Val Phe Arg Arg Ala Thr
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic anti-PCSK9 monoclonal antibody
      consensus light chain complementarity determining region 2
      (CDR2)
<220> FEATURE:
<221> NAME/KEY: VARIANT
<222> LOCATION: (1)...(1)
<223> OTHER INFORMATION: Xaa = Gly or Leu
<220> FEATURE:
```

```
<221> NAME/KEY: VARIANT
<222> LOCATION: (2)...(2)
<223> OTHER INFORMATION: Xaa = Thr or Val
<220> FEATURE:
<221> NAME/KEY: VARIANT
<222> LOCATION: (4)...(4)
<223> OTHER INFORMATION: Xaa = Asn or Arg
<220> FEATURE:
<221> NAME/KEY: VARIANT
<222> LOCATION: (5)...(5)
<223> OTHER INFORMATION: Xaa = Leu or Arg
<220> FEATURE:
<221> NAME/KEY: VARIANT
<222> LOCATION: (7)...(7)
<223> OTHER INFORMATION: Xaa = Ser or Thr

<400> SEQUENCE: 25

Xaa Xaa Phe Xaa Xaa Ala Xaa
 1               5

<210> SEQ ID NO 26
<211> LENGTH: 9
<212> TYPE: PRT
<213> ORGANISM: Artificial Sequence
<220> FEATURE:
<223> OTHER INFORMATION: synthetic mouse anti-PCSK9 monoclonal antibody
      LFU720 and anti-PCSK9 monoclonal antibody clones
      LGT-209, LGT-210 and LGT-211 light chain
      complementarity determining region 3 (CDR3)

<400> SEQUENCE: 26

Leu Gln Trp Ser Ser Asp Pro Pro Thr
 1               5

<210> SEQ ID NO 27
<211> LENGTH: 98
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 heavy chain variable
      segment (FR1-FR3)

<400> SEQUENCE: 27

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg

<210> SEQ ID NO 28
<211> LENGTH: 98
<212> TYPE: PRT
<213> ORGANISM: Artificial Sequence
<220> FEATURE:
<223> OTHER INFORMATION: synthetic anti-PCSK9 monoclonal antibody
      consensus heavy chain variable segment (FR1-FR3)
<220> FEATURE:
<221> NAME/KEY: VARIANT
<222> LOCATION: (31)...(31)
```

```
<223> OTHER INFORMATION: Xaa = Asp or Thr
<220> FEATURE:
<221> NAME/KEY: VARIANT
<222> LOCATION: (56)...(56)
<223> OTHER INFORMATION: Xaa = Ala, Glu or Gly
<220> FEATURE:
<221> NAME/KEY: VARIANT
<222> LOCATION: (61)...(61)
<223> OTHER INFORMATION: Xaa = Ala or Asp
<220> FEATURE:
<221> NAME/KEY: VARIANT
<222> LOCATION: (62)...(62)
<223> OTHER INFORMATION: Xaa = Pro or Gln
<220> FEATURE:
<221> NAME/KEY: VARIANT
<222> LOCATION: (66)...(66)
<223> OTHER INFORMATION: Xaa = Ala or Gly

<400> SEQUENCE: 28

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Xaa Met
             20                  25                  30

Tyr Met Ser Trp Val Arg Gln Ala Pro Gly Gln Gly Leu Glu Trp Met
         35                  40                  45

Gly Arg Ile Asp Pro Ala Asn Xaa His Thr Asn Tyr Xaa Xaa Lys Phe
 50                  55                  60

Gln Xaa Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                 85                  90                  95

Ala Arg

<210> SEQ ID NO 29
<211> LENGTH: 87
<212> TYPE: PRT
<213> ORGANISM: Artificial Sequence
<220> FEATURE:
<223> OTHER INFORMATION: synthetic anti-PCSK9 monoclonal antibody pJG10
      (clones LGT-209 and LGT-211) Vk light chain
      variable segment (FR1-FR3)

<400> SEQUENCE: 29

Gln Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Tyr Met
             20                  25                  30

His Trp Tyr Gln Gln Lys Pro Gly Gln Ala Pro Arg Leu Leu Ile Tyr
         35                  40                  45

Gly Val Phe Arg Arg Ala Thr Gly Ile Pro Asp Arg Phe Ser Gly Ser
 50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys
                 85

<210> SEQ ID NO 30
<211> LENGTH: 87
<212> TYPE: PRT
<213> ORGANISM: Artificial Sequence
<220> FEATURE:
<223> OTHER INFORMATION: synthetic anti-PCSK9 monoclonal antibody pJG01
      (clone LGT-210) Vk light chain variable segment
      (FR1-FR3)
```

-continued

```
<400> SEQUENCE: 30

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Tyr Met
             20                  25                  30

His Trp Tyr Gln Gln Lys Pro Gly Gln Ala Pro Arg Leu Leu Ile Tyr
         35                  40                  45

Gly Val Phe Arg Arg Ala Thr Gly Ile Pro Asp Arg Phe Ser Gly Ser
 50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys
                85

<210> SEQ ID NO 31
<211> LENGTH: 87
<212> TYPE: PRT
<213> ORGANISM: Artificial Sequence
<220> FEATURE:
<223> OTHER INFORMATION: synthetic anti-PCSK9 monoclonal antibody pJG01
      (clones LGT-209, LGT-210 and LGT-211) consensus Vk
      light chain variable segment (FR1-FR3)
<220> FEATURE:
<221> NAME/KEY: VARIANT
<222> LOCATION: (4)...(4)
<223> OTHER INFORMATION: Xaa = Leu or Met
<220> FEATURE:
<221> NAME/KEY: VARIANT
<222> LOCATION: (24)...(24)
<223> OTHER INFORMATION: Xaa = Arg or Ser
<220> FEATURE:
<221> NAME/KEY: VARIANT
<222> LOCATION: (27)...(27)
<223> OTHER INFORMATION: Xaa = Gln or Ser
<220> FEATURE:
<221> NAME/KEY: VARIANT
<222> LOCATION: (49)...(49)
<223> OTHER INFORMATION: Xaa = Gly or Leu
<220> FEATURE:
<221> NAME/KEY: VARIANT
<222> LOCATION: (50)...(50)
<223> OTHER INFORMATION: Xaa = Thr or Val
<220> FEATURE:
<221> NAME/KEY: VARIANT
<222> LOCATION: (52)...(52)
<223> OTHER INFORMATION: Xaa = Asn or Arg
<220> FEATURE:
<221> NAME/KEY: VARIANT
<222> LOCATION: (53)...(53)
<223> OTHER INFORMATION: Xaa = Leu or Arg
<220> FEATURE:
<221> NAME/KEY: VARIANT
<222> LOCATION: (55)...(55)
<223> OTHER INFORMATION: Xaa = Ser or Thr

<400> SEQUENCE: 31

Glx Ile Val Xaa Thr Gln Ser Pro Ala Thr Leu Ser Val Ser Pro Gly
  1               5                  10                  15

Glu Arg Ala Thr Leu Ser Cys Xaa Ala Ser Xaa Ser Val Ser Tyr Met
             20                  25                  30

His Trp Tyr Gln Gln Lys Pro Gly Gln Ala Pro Arg Leu Leu Ile Tyr
         35                  40                  45

Xaa Xaa Phe Xaa Xaa Ala Xaa Gly Ile Pro Asp Arg Phe Ser Gly Ser
 50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys
```

```
<210> SEQ ID NO 32
<211> LENGTH: 30
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 heavy chain framework
      region 1 (FR1)

<400> SEQUENCE: 32

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser
            20                  25                  30

<210> SEQ ID NO 33
<211> LENGTH: 14
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 heavy chain framework
      region 2 (FR2)

<400> SEQUENCE: 33

Trp Val Arg Gln Ala Pro Gly Gln Gly Leu Glu Trp Met Gly
 1               5                  10

<210> SEQ ID NO 34
<211> LENGTH: 32
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 heavy chain framework
      region 3 (FR3)

<400> SEQUENCE: 34

Arg Val Thr Met Thr Arg Asp Thr Ser Ile Ser Thr Ala Tyr Met Glu
 1               5                  10                  15

Leu Ser Arg Leu Thr Ser Asp Asp Thr Ala Val Tyr Tyr Cys Ala Arg
            20                  25                  30

<210> SEQ ID NO 35
<211> LENGTH: 11
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 heavy chain framework
      region 4 (FR4)

<400> SEQUENCE: 35

Trp Gly Gln Gly Thr Leu Val Thr Val Ser Ser
 1               5                  10

<210> SEQ ID NO 36
<211> LENGTH: 22
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 consensus light chain
      framework region 1 (FR1)
<220> FEATURE:
<221> NAME/KEY: VARIANT
<222> LOCATION: (4)...(4)
```

<223> OTHER INFORMATION: Xaa = Leu or Met

<400> SEQUENCE: 36

Glx Ile Val Xaa Thr Gln Ser Pro Ala Thr Leu Ser Val Ser Pro Gly
1               5                   10                  15

Glu Arg Ala Thr Leu Ser
            20

<210> SEQ ID NO 37
<211> LENGTH: 15
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 light chain framework
      region 2 (FR2)

<400> SEQUENCE: 37

Trp Tyr Gln Gln Lys Pro Gly Gln Ala Pro Arg Leu Leu Ile Tyr
1               5                   10                  15

<210> SEQ ID NO 38
<211> LENGTH: 32
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 light chain framework
      region 3 (FR3)

<400> SEQUENCE: 38

Gly Ile Pro Asp Arg Phe Ser Gly Ser Gly Ser Gly Thr Asp Phe Thr
1               5                   10                  15

Leu Thr Ile Gly Arg Leu Glu Pro Glu Asp Phe Ala Val Tyr Tyr Cys
            20                  25                  30

<210> SEQ ID NO 39
<211> LENGTH: 10
<212> TYPE: PRT
<213> ORGANISM: Artificial Sequence
<220> FEATURE:
<223> OTHER INFORMATION: synthetic anti-PCSK9 monoclonal antibody clones
      LGT-209, LGT-210 and LGT-211 light chain framework
      region 4 (FR4)

<400> SEQUENCE: 39

Phe Gly Gln Gly Thr Lys Leu Glu Ile Lys
1               5                   10

<210> SEQ ID NO 40
<211> LENGTH: 118
<212> TYPE: PRT
<213> ORGANISM: Artificial Sequence
<220> FEATURE:
<223> OTHER INFORMATION: synthetic anti-PCSK9 monoclonal antibody
      consensus heavy chain variable region (FR1-FR4)
<220> FEATURE:
<221> NAME/KEY: VARIANT
<222> LOCATION: (31)...(31)
<223> OTHER INFORMATION: Xaa = Asp or Thr
<220> FEATURE:
<221> NAME/KEY: VARIANT
<222> LOCATION: (56)...(56)
<223> OTHER INFORMATION: Xaa = Ala, Glu or Gly
<220> FEATURE:
<221> NAME/KEY: VARIANT
<222> LOCATION: (61)...(61)
<223> OTHER INFORMATION: Xaa = Ala or Asp
<220> FEATURE:
<221> NAME/KEY: VARIANT

```
<222> LOCATION: (62)...(62)
<223> OTHER INFORMATION: Xaa = Pro or Gln
<220> FEATURE:
<221> NAME/KEY: VARIANT
<222> LOCATION: (66)...(66)
<223> OTHER INFORMATION: Xaa = Ala or Gly
<220> FEATURE:
<221> NAME/KEY: VARIANT
<222> LOCATION: (104)...(104)
<223> OTHER INFORMATION: Xaa = Ala or Asn
<220> FEATURE:
<221> NAME/KEY: VARIANT
<222> LOCATION: (107)...(107)
<223> OTHER INFORMATION: Xaa = Ala, Phe, Ser, Val or Tyr

<400> SEQUENCE: 40

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Xaa Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Xaa His Thr Asn Tyr Xaa Xaa Lys Phe
    50                  55                  60

Gln Xaa Arg Val Thr Met Thr Arg Asp Thr Ser Ile Ser Thr Ala Tyr
65              70                  75                  80

Met Glu Leu Ser Arg Leu Thr Ser Asp Asp Thr Ala Val Tyr Tyr Cys
                85                  90                  95

Ala Arg Ser Tyr Tyr Tyr Tyr Xaa Met Asp Xaa Trp Gly Gln Gly Thr
            100                 105                 110

Leu Val Thr Val Ser Ser
        115

<210> SEQ ID NO 41
<211> LENGTH: 106
<212> TYPE: PRT
<213> ORGANISM: Artificial Sequence
<220> FEATURE:
<223> OTHER INFORMATION: synthetic anti-PCSK9 monoclonal antibody
      consensus light chain variable region (FR1-FR4)
<220> FEATURE:
<221> NAME/KEY: VARIANT
<222> LOCATION: (4)...(4)
<223> OTHER INFORMATION: Xaa = Leu or Met
<220> FEATURE:
<221> NAME/KEY: VARIANT
<222> LOCATION: (24)...(24)
<223> OTHER INFORMATION: Xaa = Arg or Ser
<220> FEATURE:
<221> NAME/KEY: VARIANT
<222> LOCATION: (27)...(27)
<223> OTHER INFORMATION: Xaa = Gln or Ser
<220> FEATURE:
<221> NAME/KEY: VARIANT
<222> LOCATION: (49)...(49)
<223> OTHER INFORMATION: Xaa = Gly or Leu
<220> FEATURE:
<221> NAME/KEY: VARIANT
<222> LOCATION: (50)...(50)
<223> OTHER INFORMATION: Xaa = Thr or Val
<220> FEATURE:
<221> NAME/KEY: VARIANT
<222> LOCATION: (52)...(52)
<223> OTHER INFORMATION: Xaa = Asn or Arg
<220> FEATURE:
<221> NAME/KEY: VARIANT
<222> LOCATION: (53)...(53)
<223> OTHER INFORMATION: Xaa = Leu or Arg
<220> FEATURE:
<221> NAME/KEY: VARIANT
<222> LOCATION: (55)...(55)
```

<223> OTHER INFORMATION: Xaa = Ser or Thr

<400> SEQUENCE: 41

Glx Ile Val Xaa Thr Gln Ser Pro Ala Thr Leu Ser Val Ser Pro Gly
1               5                   10                  15

Glu Arg Ala Thr Leu Ser Cys Xaa Ala Ser Xaa Ser Val Ser Tyr Met
            20                  25                  30

His Trp Tyr Gln Gln Lys Pro Gly Gln Ala Pro Arg Leu Leu Ile Tyr
        35                  40                  45

Xaa Xaa Phe Xaa Xaa Ala Xaa Gly Ile Pro Asp Arg Phe Ser Gly Ser
    50                  55                  60

Gly Ser Gly Thr Asp Phe Thr Leu Thr Ile Gly Arg Leu Glu Pro Glu
65              70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys
            100                 105

<210> SEQ ID NO 42
<211> LENGTH: 354
<212> TYPE: DNA
<213> ORGANISM: Artificial Sequence
<220> FEATURE:
<223> OTHER INFORMATION: synthetic anti-PCSK9 monoclonal antibody pJG04
      (clones LGT-209 and LGT-210) heavy chain

<400> SEQUENCE: 42
caggttcagc tggtgcagtc tggggctgag gtgaagaagc ctggggcctc agtgaaggtc      60
tcctgcaagg cttctggata caccttcagc actatgtata tgtcttgggt gcgacaggcc     120
cctggacaag gcttgagtg gatgggaagg atcgatcctg ccaatgagca cactaactat      180
gcccagaagt tccaggggag ggtgactatg acaagggaca catccatcag cacagcctac     240
atggagctca gcaggctgac gtctgacgac actgccgtct attactgtgc tagaagttac     300
tattactata acatggacta ctggggtcaa ggtaccctgg tgaccgtcag ctca           354

<210> SEQ ID NO 43
<211> LENGTH: 354
<212> TYPE: DNA
<213> ORGANISM: Artificial Sequence
<220> FEATURE:
<223> OTHER INFORMATION: synthetic anti-PCSK9 monoclonal antibody pSR74
      (clone LGT-211) heavy chain

<400> SEQUENCE: 43
caggttcagc tggtgcagtc tggggctgag gtgaagaagc ctggggcctc agtgaaggtc      60
tcctgcaagg cttctggata caccttcagc actatgtata tgtcttgggt gcgacaggcc     120
cctggacaag gcttgagtg gatgggaagg atcgatcctg ccaatgagca cactaactat      180
gcccagaagt tccaggggag ggtgactatg acaagggaca catccatcag cacagcctac     240
atggagctca gcaggctgac gtctgacgac actgccgtct attactgtgc tagaagttac     300
tattactatg ctatggacta ctggggtcaa ggtaccctgg tgaccgtcag ctca           354

<210> SEQ ID NO 44
<211> LENGTH: 318
<212> TYPE: DNA
<213> ORGANISM: Artificial Sequence
<220> FEATURE:
<223> OTHER INFORMATION: synthetic anti-PCSK9 monoclonal antibody pJG01
      (clone LGT-210) light chain -continued

```
<400> SEQUENCE: 44
gaaatagtga tgacgcagtc tccagccacc ctgtctgtgt ctccagggga aagagccacc     60
ctctcctgca gggccagtca gagtgttagc tatatgcatt ggtaccagca gaagccaggc    120
caggctccca ggctcctcat atatggtgtt ttcagaaggg ccactggcat cccagacagg    180
ttcagtggca gtgggtctgg gacagacttc actctcacca tcggcagact ggagcctgaa    240
gattttgcag tgtactactg cctacagtgg agtagtgacc cacccacgtt tggccaaggt    300
acgaagcttg aaattaaa                                                  318

<210> SEQ ID NO 45
<211> LENGTH: 318
<212> TYPE: DNA
<213> ORGANISM: Artificial Sequence
<220> FEATURE:
<223> OTHER INFORMATION: synthetic anti-PCSK9 monoclonal antibody pJG10
      (clones LGT-209 and LGT-211) light chain

<400> SEQUENCE: 45
cagattgttc tcacccagtc tccagccacc ctgtctgtgt ctccagggga aagagccacc     60
ctctcctgca gggccagtca gagtgttagc tatatgcatt ggtaccagca gaagccaggc    120
caggctccca ggctcctcat atatggtgtt ttcagaaggg ccactggcat cccagacagg    180
ttcagtggca gtgggtctgg gacagacttc actctcacca tcggcagact ggagcctgaa    240
gattttgcag tgtactactg cctacagtgg agtagtgacc cacccacgtt tggccaaggt    300
acgaagcttg aaattaaa                                                  318

<210> SEQ ID NO 46
<211> LENGTH: 13
<212> TYPE: PRT
<213> ORGANISM: Artificial Sequence
<220> FEATURE:
<223> OTHER INFORMATION: synthetic anti-PCSK9 monoclonal antibody
      epitope

<400> SEQUENCE: 46

Arg Ser Arg His Leu Ala Gln Ala Ser Gln Glu Leu Gln
 1               5                  10

<210> SEQ ID NO 47
<211> LENGTH: 692
<212> TYPE: PRT
<213> ORGANISM: Homo sapiens
<220> FEATURE:
<223> OTHER INFORMATION: human proprotein convertase subtilisin/kexin
      type 9 (PCSK9), proprotein convertase 9 (PC9), neural
      apoptosis-regulated convertase 1 (NARC1, NARC-1),
      FH3, HCHOLA3, LDLCQ1 preproprotein
<220> FEATURE:
<221> NAME/KEY: SIGNAL
<222> LOCATION: (1)...(30)
<223> OTHER INFORMATION: signal peptide
<220> FEATURE:
<221> NAME/KEY: PROPEP
<222> LOCATION: (31)...(692)
<223> OTHER INFORMATION: proprotein
<220> FEATURE:
<221> NAME/KEY: CHAIN
<222> LOCATION: (153)...(692)
<223> OTHER INFORMATION: mature protein

<400> SEQUENCE: 47

Met Gly Thr Val Ser Ser Arg Arg Ser Trp Trp Pro Leu Pro Leu Leu
-30                 -25                 -20                 -15

Leu Leu Leu Leu Leu Leu Leu Gly Pro Ala Gly Ala Arg Ala Gln Glu
```

-continued

```
            -10              -5                  1
Asp Glu Asp Gly Asp Tyr Glu Leu Val Leu Ala Leu Arg Ser Glu
                5              10                  15
Glu Asp Gly Leu Ala Glu Ala Pro Glu His Gly Thr Thr Ala Thr Phe
 20              25                  30
His Arg Cys Ala Lys Asp Pro Trp Arg Leu Pro Gly Thr Tyr Val Val
 35              40                  45                      50
Val Leu Lys Glu Glu Thr His Leu Ser Gln Ser Glu Arg Thr Ala Arg
                55                  60                  65
Arg Leu Gln Ala Gln Ala Ala Arg Arg Gly Tyr Leu Thr Lys Ile Leu
                70                  75                  80
His Val Phe His Gly Leu Leu Pro Gly Phe Leu Val Lys Met Ser Gly
                85                  90                  95
Asp Leu Leu Glu Leu Ala Leu Lys Leu Pro His Val Asp Tyr Ile Glu
 100                 105                 110
Glu Asp Ser Ser Val Phe Ala Gln Ser Ile Pro Trp Asn Leu Glu Arg
 115                 120                 125                 130
Ile Thr Pro Pro Arg Tyr Arg Ala Asp Glu Tyr Gln Pro Pro Asp Gly
                    135                 140                 145
Gly Ser Leu Val Glu Val Tyr Leu Leu Asp Thr Ser Ile Gln Ser Asp
                    150                 155                 160
His Arg Glu Ile Glu Gly Arg Val Met Val Thr Asp Phe Glu Asn Val
                    165                 170                 175
Pro Glu Glu Asp Gly Thr Arg Phe His Arg Gln Ala Ser Lys Cys Asp
 180                 185                 190
Ser His Gly Thr His Leu Ala Gly Val Val Ser Gly Arg Asp Ala Gly
 195                 200                 205                 210
Val Ala Lys Gly Ala Ser Met Arg Ser Leu Arg Val Leu Asn Cys Gln
                    215                 220                 225
Gly Lys Gly Thr Val Ser Gly Thr Leu Ile Gly Leu Glu Phe Ile Arg
                    230                 235                 240
Lys Ser Gln Leu Val Gln Pro Val Gly Pro Leu Val Val Leu Leu Pro
                    245                 250                 255
Leu Ala Gly Gly Tyr Ser Arg Val Leu Asn Ala Ala Cys Gln Arg Leu
 260                 265                 270
Ala Arg Ala Gly Val Val Leu Val Thr Ala Ala Gly Asn Phe Arg Asp
 275                 280                 285                 290
Asp Ala Cys Leu Tyr Ser Pro Ala Ser Ala Pro Glu Val Ile Thr Val
                    295                 300                 305
Gly Ala Thr Asn Ala Gln Asp Gln Pro Val Thr Leu Gly Thr Leu Gly
                    310                 315                 320
Thr Asn Phe Gly Arg Cys Val Asp Leu Phe Ala Pro Gly Glu Asp Ile
                    325                 330                 335
Ile Gly Ala Ser Ser Asp Cys Ser Thr Cys Phe Val Ser Gln Ser Gly
                    340                 345                 350
Thr Ser Gln Ala Ala Ala His Val Ala Gly Ile Ala Ala Met Met Leu
 355                 360                 365                 370
Ser Ala Glu Pro Glu Leu Thr Leu Ala Glu Leu Arg Gln Arg Leu Ile
                    375                 380                 385
His Phe Ser Ala Lys Asp Val Ile Asn Glu Ala Trp Phe Pro Glu Asp
                    390                 395                 400
Gln Arg Val Leu Thr Pro Asn Leu Val Ala Ala Leu Pro Pro Ser Thr
                    405                 410                 415
```

```
His Gly Ala Gly Trp Gln Leu Phe Cys Arg Thr Val Trp Ser Ala His
    420                 425                 430
Ser Gly Pro Thr Arg Met Ala Thr Ala Val Ala Arg Cys Ala Pro Asp
435                 440                 445                 450
Glu Glu Leu Leu Ser Cys Ser Ser Phe Ser Arg Ser Gly Lys Arg Arg
                455                 460                 465
Gly Glu Arg Met Glu Ala Gln Gly Gly Lys Leu Val Cys Arg Ala His
            470                 475                 480
Asn Ala Phe Gly Gly Glu Gly Val Tyr Ala Ile Ala Arg Cys Cys Leu
        485                 490                 495
Leu Pro Gln Ala Asn Cys Ser Val His Thr Ala Pro Pro Ala Glu Ala
    500                 505                 510
Ser Met Gly Thr Arg Val His Cys His Gln Gln Gly His Val Leu Thr
515                 520                 525                 530
Gly Cys Ser Ser His Trp Glu Val Glu Asp Leu Gly Thr His Lys Pro
                535                 540                 545
Pro Val Leu Arg Pro Arg Gly Gln Pro Asn Gln Cys Val Gly His Arg
            550                 555                 560
Glu Ala Ser Ile His Ala Ser Cys Cys His Ala Pro Gly Leu Glu Cys
        565                 570                 575
Lys Val Lys Glu His Gly Ile Pro Ala Pro Gln Glu Gln Val Thr Val
    580                 585                 590
Ala Cys Glu Glu Gly Trp Thr Leu Thr Gly Cys Ser Ala Leu Pro Gly
595                 600                 605                 610
Thr Ser His Val Leu Gly Ala Tyr Ala Val Asp Asn Thr Cys Val Val
                615                 620                 625
Arg Ser Arg Asp Val Ser Thr Thr Gly Ser Thr Ser Glu Gly Ala Val
            630                 635                 640
Thr Ala Val Ala Ile Cys Cys Arg Ser Arg His Leu Ala Gln Ala Ser
        645                 650                 655
Gln Glu Leu Gln
    660

<210> SEQ ID NO 48
<211> LENGTH: 3636
<212> TYPE: DNA
<213> ORGANISM: Homo sapiens
<220> FEATURE:
<221> NAME/KEY: CDS
<222> LOCATION: (292)...(2370)
<223> OTHER INFORMATION: human proprotein convertase subtilisin/kexin
      type 9 (PCSK9), proprotein convertase 9 (PC9), neural
      apoptosis-regulated convertase 1 (NARC1, NARC-1),
      FH3, HCHOLA3, LDLCQ1 preproprotein
<220> FEATURE:
<221> NAME/KEY: sig_peptide
<222> LOCATION: (292)...(381)
<223> OTHER INFORMATION: signal peptide
<220> FEATURE:
<221> NAME/KEY: misc_structure
<222> LOCATION: (382)...(2367)
<223> OTHER INFORMATION: proprotein
<220> FEATURE:
<221> NAME/KEY: mat_peptide
<222> LOCATION: (538)...(2367)
<223> OTHER INFORMATION: mature protein

<400> SEQUENCE: 48
cagcgacgtc gaggcgctca tggttgcagg cgggcgccgc cgttcagttc agggtctgag      60
cctggaggag tgagccaggc agtgagactg gctcgggcgg ccgggacgc gtcgttgcag     120 cagcggctcc cagctcccag ccaggattcc gcgcgcccct tcacgcgccc tgctcctgaa     180
```

-continued

```
cttcagctcc tgcacagtcc tccccaccgc aaggctcaag gcgccgccgg cgtggaccgc      240
gcacggcctc taggtctcct cgccaggaca gcaacctctc ccctggccct catgggcacc      300
gtcagctcca ggcggtcctg gtggccgctg ccactgctgc tgctgctgct gctgctcctg      360
ggtcccgcgg gcgcccgtgc gcaggaggac gaggacggcg actacgagga gctggtgcta      420
gccttgcgtt ccgaggagga cggcctggcc gaagcacccg agcacggaac cacagccacc      480
ttccaccgct gcgccaagga tccgtggagg ttgcctggca cctacgtggt ggtgctgaag      540
gaggagaccc acctctcgca gtcagagcgc actgcccgcc gcctgcaggc ccaggctgcc      600
cgccggggat acctcaccaa gatcctgcat gtcttccatg gccttcttcc tggcttcctg      660
gtgaagatga gtggcgacct gctggagctg gccttgaagt tgccccatgt cgactacatc      720
gaggaggact cctctgtctt tgcccagagc atcccgtgga acctggagcg gattacccct      780
ccacggtacc gggcggatga ataccagccc cccgacggag gcagcctggt ggaggtgtat      840
ctcctagaca ccagcataca gagtgaccac cgggaaatcg agggcagggt catggtcacc      900
gacttcgaga atgtgcccga ggaggacggg acccgcttcc acagacaggc cagcaagtgt      960
gacagtcatg gcacccacct ggcagggtgt gtcagcggcc gggatgccgg cgtggccaag      1020
ggtgccagca tgcgcagcct gcgcgtgctc aactgccaag ggaagggcac ggttagcggc      1080
accctcatag gcctggagtt tattcggaaa gccagctgg tccagcctgt ggggccactg       1140
gtggtgctgc tgcccctggc gggtgggtac agccgcgtcc tcaacgccgc ctgccagcgc      1200
ctggcgaggc tggggtcgt gctggtcacc gctgccggca acttccggga cgatgcctgc       1260
ctctactccc cagcctcagc tcccgaggtc atcacagttg ggccaccaa tgcccaagac       1320 cagccggtga ccctggggac tttggggacc aactttggcc gctgtgtgga cctctttgcc      1380
ccagggaggg acatcattgg tgcctccagc gactgcagca cctgctttgt gtcacagagt      1440
gggacatcac aggctgctgc ccacgtggct ggcattgcag ccatgatgct gtctgccgag      1500
ccggagctca ccctggccga gttgaggcag agactgatcc acttctctgc caaagatgtc      1560
atcaatgagg cctggttccc tgaggaccag cgggtactga cccccaacct ggtggccgcc      1620 ctgccccca gcacccatgg ggcaggttgg cagctgtttt gcaggactgt atggtcagca       1680
cactcggggc ctacacggat ggccacagcc gtcgcccgct cgcccccaga tgaggagctg      1740
ctgagctgct ccagtttctc caggagtggg aagcggcggg gcgagcgcat ggaggcccaa      1800 ggggcaagc tggtctgccg ggcccacaac gctttgggg gtgagggtgt ctacgccatt        1860
gccaggtgct gcctgctacc ccaggccaac tgcagcgtcc acacagctcc accagctgag      1920
gccagcatgg ggacccgtgt ccactgccac caacagggcc acgtcctcac aggctgcagc      1980
tcccactggg aggtggagga ccttggcacc cacaagccgc ctgtgctgag gccacgaggt      2040
cagcccaacc agtgcgtggg ccacaggag gccagcatcc acgcttcctg ctgccatgcc       2100
ccaggtctgg aatgcaaagt caaggagcat ggaatcccgg cccctcagga gcaggtgacc      2160
gtggcctgcg aggagggctg gaccctgact ggctgcagtg ccctccctgg gacctcccac      2220
gtcctggggg cctacgccgt agacaacacg tgtgtagtca ggagccggga cgtcagcact      2280
acaggcagca ccagcgaagg ggccgtgaca gccgttgcca tctgctgccg gagccggcac      2340
ctggcgcagg cctcccagga gctccagtga cagcccatc ccaggatggg tgtctgggga       2400
gggtcaaggg ctggggctga gctttaaaat ggttccgact tgtccctctc tcagccctcc      2460
atggcctggc acgaggggat ggggatgctt ccgcctttcc ggggctgctg gcctggccct      2520
tgagtggggc agcctccttg cctggaactc actcactctg ggtgcctcct ccccaggtgg      2580
```

```
aggtgccagg aagctccctc cctcactgtg gggcatttca ccattcaaac aggtcgagct   2640
gtgctcgggt gctgccagct gctcccaatg tgccgatgtc cgtgggcaga atgacttta    2700 ttgagctctt gttccgtgcc aggcattcaa tcctcaggtc tccaccaagg aggcaggatt   2760
cttcccatgg ataggggagg gggcggtagg ggctgcaggg acaaacatcg ttgggggtg    2820 agtgtgaaag gtgctgatgg ccctcatctc cagctaactg tggagaagcc cctgggggct   2880
ccctgattaa tggaggctta gctttctgga tggcatctag ccagaggctg gagacaggtg   2940 cgccctggt ggtcacaggc tgtgcccttgg tttcctgagc cacctttact ctgctctatg    3000
ccaggctgtg ctagcaacac ccaaaggtgg cctgcgggga gccatcacct aggactgact   3060
cggcagtgtg cagtggtgca tgcactgtct cagccaaccc gctccactac ccggcagggt   3120
acacattcgc accctactt cacagaggaa gaaacctgga accagagggg gcgtgcctgc    3180
caagctcaca cagcaggaac tgagccagaa acgcagattg gctggctct gaagccaagc    3240 ctcttcttac ttcacccggc tgggctcctc attttacgg gtaacagtga ggctgggaag    3300
gggaacacag accaggaagc tcggtgagtg atggcagaac gatgcctgca ggcatggaac   3360
tttttccgtt atcacccagg cctgattcac tggcctggcg gagatgcttc taaggcatgg   3420 tcggggaga gggccaacaa ctgtccctcc ttgagcacca gccccaccca agcaagcaga    3480
catttatctt ttgggtctgt cctctctgtt gccttttac agccaacttt tctagacctg    3540
ttttgctttt gtaacttgaa gatatttatt ctgggttttg tagcattttt attaatatgg   3600
tgacttttta aaataaaaac aaacaaacgt tgtcct                             3636
```

<210> SEQ ID NO 49
<211> LENGTH: 13
<212> TYPE: PRT
<213> ORGANISM: Artificial Sequence
<220> FEATURE:
<223> OTHER INFORMATION: synthetic anti-PCSK9 C-terminus epitope,
      residues 680-692

<400> SEQUENCE: 49

Arg Ser Arg His Leu Ala Gln Ala Ser Gln Glu Leu Gln
1               5                   10

<210> SEQ ID NO 50
<211> LENGTH: 11
<212> TYPE: PRT
<213> ORGANISM: Artificial Sequence
<220> FEATURE:
<223> OTHER INFORMATION: synthetic human germline JH4 partial sequence
      in anti-PCSK9 heavy chain J-segment

<400> SEQUENCE: 50

Trp Gly Gln Gly Thr Leu Val Thr Val Ser Ser
1               5                   10

<210> SEQ ID NO 51
<211> LENGTH: 15
<212> TYPE: PRT
<213> ORGANISM: Artificial Sequence
<220> FEATURE:
<223> OTHER INFORMATION: synthetic full-length J-segment from human
      germline JH4

<400> SEQUENCE: 51

Tyr Phe Asp Tyr Trp Gly Gln Gly Thr Leu Val Thr Val Ser Ser
1               5                   10                  15

```
<210> SEQ ID NO 52
<211> LENGTH: 10
<212> TYPE: PRT
<213> ORGANISM: Artificial Sequence
<220> FEATURE:
<223> OTHER INFORMATION: synthetic human germline Jk2 partial sequence
      in anti-PCSK9 light chain J-segment

<400> SEQUENCE: 52

Phe Gly Gln Gly Thr Lys Leu Glu Ile Lys
 1               5                  10

<210> SEQ ID NO 53
<211> LENGTH: 12
<212> TYPE: PRT
<213> ORGANISM: Artificial Sequence
<220> FEATURE:
<223> OTHER INFORMATION: synthetic full-length J-segment from human
      germline Jk2

<400> SEQUENCE: 53

Tyr Thr Phe Gly Gln Gly Thr Lys Leu Glu Ile Lys
 1               5                  10

<210> SEQ ID NO 54
<211> LENGTH: 354
<212> TYPE: DNA
<213> ORGANISM: Mus musculus
<220> FEATURE:
<223> OTHER INFORMATION: mouse anti-PCSK9 monoclonal antibody LFU270
      heavy chain variable region

<400> SEQUENCE: 54
gaggttcagc tgcagcagtc tggggcagag cttatgaagc caggggcctc agtcaagttg      60
tcctgcacag cttctggctt caacatcaaa gacatgtata tgagctgggt gaggcagagg     120
cctgaacagg gcctgagtg gattggaagg atcgatcctg cgaatggtca tactaactat      180
gacccgaagt tccaggccaa ggccactata acaacagaca catcctccaa aacagcctac     240
ctgcatctca gcagcctgac atctgaggac actgccgtct attactgtgc tagaagttac     300
tattactatg ctatggacta ctgggggtcaa ggaacctcag tcaccgtctc ttca           354

<210> SEQ ID NO 55
<211> LENGTH: 318
<212> TYPE: DNA
<213> ORGANISM: Mus musculus
<220> FEATURE:
<223> OTHER INFORMATION: mouse anti-PCSK9 monoclonal antibody LFU270
      light chain variable region

<400> SEQUENCE: 55
caaattgttc tcacccagtc tccagcaatc atgtctgcat ctccagggga gaaggtcacc      60
atgacctgca gtgccagctc aagtgtaagt tacatgcact ggtaccagca gaagccagga     120
tcctccccca gactctggat ttatttaaca ttcaacttgg cttctggagt ccctgctcgc     180
ttcagtggca gtgggtctgg gacctcttac tctctctcaa tcagcagcat ggaggctgaa     240
gatgctgcca cttattactg tctacagtgg agtagtgacc cacccacgtt cggctcgggg     300
acaaagttgg aaataaaa                                                   318

<210> SEQ ID NO 56
<211> LENGTH: 5
<212> TYPE: PRT
<213> ORGANISM: Artificial Sequence
<220> FEATURE:
<223> OTHER INFORMATION: synthetic PCSK9 C-terminal mutant A685X
```

```
<400> SEQUENCE: 56

Arg Ser Arg His Leu
1               5

<210> SEQ ID NO 57
<211> LENGTH: 6
<212> TYPE: PRT
<213> ORGANISM: Artificial Sequence
<220> FEATURE:
<223> OTHER INFORMATION: synthetic C-terminal his6 tag, 6-His tag,
      HIS-tag

<400> SEQUENCE: 57

His His His His His His
1               5

<210> SEQ ID NO 58
<211> LENGTH: 19
<212> TYPE: DNA
<213> ORGANISM: Artificial Sequence
<220> FEATURE:
<223> OTHER INFORMATION: synthetic RT-PCR amplification primer V-H14 for
      heavy chain variable region

<400> SEQUENCE: 58
cttcctgatg gcagtggtt                                              19

<210> SEQ ID NO 59
<211> LENGTH: 39
<212> TYPE: DNA
<213> ORGANISM: Artificial Sequence
<220> FEATURE:
<223> OTHER INFORMATION: synthetic RT-PCR amplification primer
      HCconstant for heavy chain variable region

<400> SEQUENCE: 59
gcgtctagaa yctccacaca caggrrccag tggatagac                        39

<210> SEQ ID NO 60
<211> LENGTH: 21
<212> TYPE: DNA
<213> ORGANISM: Artificial Sequence
<220> FEATURE:
<223> OTHER INFORMATION: synthetic RT-PCR amplification primer Vkappa4/5
      for light chain variable region

<400> SEQUENCE: 60
tcagcttcyt gctaatcagt g                                           21

<210> SEQ ID NO 61
<211> LENGTH: 29
<212> TYPE: DNA
<213> ORGANISM: Artificial Sequence
<220> FEATURE:
<223> OTHER INFORMATION: synthetic RT-PCR amplification primer
      LCconstant for light chain variable region

<400> SEQUENCE: 61
gcgtctagaa ctggatggtg ggaagatgg                                   29

<210> SEQ ID NO 62
<211> LENGTH: 11
<212> TYPE: PRT
<213> ORGANISM: Artificial Sequence
<220> FEATURE:
<223> OTHER INFORMATION: synthetic C-terminal flexible linker and 6-His
      tag
```

```
<400> SEQUENCE: 62

Ala Ala Gly Ala Ser His His His His His
1               5                   10

<210> SEQ ID NO 63
<211> LENGTH: 17
<212> TYPE: PRT
<213> ORGANISM: Artificial Sequence
<220> FEATURE:
<223> OTHER INFORMATION: synthetic Avi tag for site-directed
      biotinylation

<400> SEQUENCE: 63

Gly Gly Gly Leu Asn Asp Ile Phe Glu Ala Gln Lys Ile Glu Trp His
1               5                   10                  15

Glu

<210> SEQ ID NO 64
<211> LENGTH: 5
<212> TYPE: PRT
<213> ORGANISM: Artificial Sequence
<220> FEATURE:
<223> OTHER INFORMATION: synthetic CDRH1 of SR066 (humaneered)

<400> SEQUENCE: 64

Thr Tyr Tyr Met Asn
1               5

<210> SEQ ID NO 65
<211> LENGTH: 5
<212> TYPE: PRT
<213> ORGANISM: Artificial Sequence
<220> FEATURE:
<223> OTHER INFORMATION: synthetic CDRH1 of SR038 (mouse)

<400> SEQUENCE: 65

Asp Met Tyr Met Ser
1               5

<210> SEQ ID NO 66
<211> LENGTH: 5
<212> TYPE: PRT
<213> ORGANISM: Artificial Sequence
<220> FEATURE:
<223> OTHER INFORMATION: synthetic CDRH1 of SR079 (humaneered)

<400> SEQUENCE: 66

Thr Met Tyr Met Ser
1               5

<210> SEQ ID NO 67
<211> LENGTH: 4
<212> TYPE: PRT
<213> ORGANISM: Artificial Sequence
<220> FEATURE:
<223> OTHER INFORMATION: synthetic 7472 light chain (LC) N-terminus

<400> SEQUENCE: 67

Glu Ile Val Met
1

<210> SEQ ID NO 68
<211> LENGTH: 12
<212> TYPE: PRT
<213> ORGANISM: Artificial Sequence
<220> FEATURE:
```

```
<223> OTHER INFORMATION: synthetic 7472 light chain (LC) CDR1

<400> SEQUENCE: 68

Arg Ala Ser Gln Ser Val Ser Ser His Val Ala
1               5                   10

<210> SEQ ID NO 69
<211> LENGTH: 4
<212> TYPE: PRT
<213> ORGANISM: Artificial Sequence
<220> FEATURE:
<223> OTHER INFORMATION: synthetic LFU720 and pJG10 light chain (LC)
      N-terminus

<400> SEQUENCE: 69

Gln Ile Val Leu
1

<210> SEQ ID NO 70
<211> LENGTH: 10
<212> TYPE: PRT
<213> ORGANISM: Artificial Sequence
<220> FEATURE:
<223> OTHER INFORMATION: synthetic LFU720 light chain (LC)
      complementarity determining region 1 (CDR1)

<400> SEQUENCE: 70

Ser Ala Ser Ser Ser Val Ser Tyr Met His
1               5                   10

<210> SEQ ID NO 71
<211> LENGTH: 10
<212> TYPE: PRT
<213> ORGANISM: Artificial Sequence
<220> FEATURE:
<223> OTHER INFORMATION: synthetic pJG10 light chain (LC)
      complementarity determining region 1 (CDR1)

<400> SEQUENCE: 71

Arg Ala Ser Gln Ser Val Ser Tyr Met His
1               5                   10

<210> SEQ ID NO 72
<211> LENGTH: 12
<212> TYPE: PRT
<213> ORGANISM: Artificial Sequence
<220> FEATURE:
<223> OTHER INFORMATION: synthetic 7472 and LFU720 heavy chain CDR3
      (CDRH3)

<400> SEQUENCE: 72

Cys Ala Arg Ser Tyr Tyr Tyr Tyr Ala Met Asp Tyr
1               5                   10

<210> SEQ ID NO 73
<211> LENGTH: 12
<212> TYPE: PRT
<213> ORGANISM: Artificial Sequence
<220> FEATURE:
<223> OTHER INFORMATION: synthetic pJG04 heavy chain CDR3 (CDRH3)

<400> SEQUENCE: 73

Cys Ala Arg Ser Tyr Tyr Tyr Tyr Asn Met Asp Tyr
1               5                   10

<210> SEQ ID NO 74
<211> LENGTH: 17
<212> TYPE: PRT
```

```
<213> ORGANISM: Artificial Sequence
<220> FEATURE:
<223> OTHER INFORMATION: synthetic anti-PCSK9 heavy chain CDR2

<400> SEQUENCE: 74

Arg Ile Asp Pro Ala Asn Glu His Thr Asn Tyr Ala Gln Lys Phe Gln
 1               5                  10                  15

Gly

<210> SEQ ID NO 75
<211> LENGTH: 9
<212> TYPE: PRT
<213> ORGANISM: Artificial Sequence
<220> FEATURE:
<223> OTHER INFORMATION: synthetic anti-PCSK9 heavy chain CDR3
<221> NAME/KEY: VARIANT
<222> LOCATION: (6)...(6)
<223> OTHER INFORMATION: Xaa = Ala or Asn

<400> SEQUENCE: 75

Ser Tyr Tyr Tyr Tyr Xaa Met Asp Tyr
 1               5

<210> SEQ ID NO 76
<211> LENGTH: 23
<212> TYPE: PRT
<213> ORGANISM: Artificial Sequence
<220> FEATURE:
<223> OTHER INFORMATION: synthetic anti-PCSK9 light chain FR1
<220> FEATURE:
<221> NAME/KEY: VARIANT
<222> LOCATION: (4)...(4)
<223> OTHER INFORMATION: Xaa = Met or Leu

<400> SEQUENCE: 76

Glx Ile Val Xaa Thr Gln Ser Pro Ala Thr Leu Ser Val Ser Pro Gly
 1               5                  10                  15

Glu Arg Ala Thr Leu Ser Cys
                20
```